United States Patent
Pandya et al.

(10) Patent No.: US 11,432,766 B2
(45) Date of Patent: Sep. 6, 2022

(54) WEARABLE ELECTRONIC DEVICE WITH ELECTRODES FOR SENSING BIOLOGICAL PARAMETERS

(71) Applicant: Apple Inc., Cupertino, CA (US)

(72) Inventors: Sameer Pandya, Sunnyvale, CA (US); Adam T. Clavelle, San Francisco, CA (US); Erik G. de Jong, San Francisco, CA (US); Michael B. Wittenberg, San Francisco, CA (US); Tobias J. Harrison-Noonan, San Francisco, CA (US); Martin Melcher, Mountain View, CA (US); Zhipeng Zhang, Santa Clara, CA (US); Steven C. Roach, San Francisco, CA (US); Steven P. Cardinali, Campbell, CA (US)

(73) Assignee: Apple Inc., Cupertino, CA (US)

( * ) Notice: Subject to any disclaimer, the term of this patent is extended or adjusted under 35 U.S.C. 154(b) by 962 days.

(21) Appl. No.: 16/118,282

(22) Filed: Aug. 30, 2018

(65) Prior Publication Data
US 2019/0072912 A1    Mar. 7, 2019

Related U.S. Application Data

(60) Provisional application No. 62/644,886, filed on Mar. 19, 2018, provisional application No. 62/554,196, filed on Sep. 5, 2017.

(51) Int. Cl.
*A61B 5/00*    (2006.01)
*G06F 1/16*    (2006.01)
(Continued)

(52) U.S. Cl.
CPC .......... *A61B 5/681* (2013.01); *A61B 5/02427* (2013.01); *A61B 5/02438* (2013.01);
(Continued)

(58) Field of Classification Search
CPC ......... A61B 5/681; A61B 5/282; A61B 5/332; A61B 5/339; A61B 5/02427;
(Continued)

(56) References Cited

U.S. PATENT DOCUMENTS

| | | |
|---|---|---|
| 4,015,595 A | 4/1977 | Benjamin, Jr. |
| 6,198,951 B1 | 3/2001 | Kosuda |

(Continued)

FOREIGN PATENT DOCUMENTS

| | | |
|---|---|---|
| CN | 1572252 | 2/2005 |
| CN | 1985762 | 6/2007 |

(Continued)

OTHER PUBLICATIONS

U.S. Appl. No. 16/118,254, filed Aug. 30, 2018, Harrison-Noonan et al.

(Continued)

*Primary Examiner* — Omar Casillashernandez
(74) *Attorney, Agent, or Firm* — Brownstein Hyatt Farber Schreck, LLP

(57) ABSTRACT

An electronic device, such as a watch, has a housing to which a carrier is attached. The carrier has a first surface interior to the electronic device, and a second surface exterior to the electronic device. A set of electrodes is deposited on the exterior surface of the carrier. An additional electrode is operable to be contacted by a finger of a user of the electronic device while the first electrode is positioned against skin of the user. The additional electrode may be positioned on a user-rotatable crown of the electronic device, on a button of the electronic device, or on another surface of the housing of the electronic device. A processor of the electronic device is operable to determine a biological parameter of the user based on voltages at the electrodes. The biological parameter may be an electrocardiogram.

20 Claims, 41 Drawing Sheets

(51) Int. Cl.
  *A61B 5/282* (2021.01)
  *A61B 5/332* (2021.01)
  *A61B 5/339* (2021.01)
  *A61B 5/024* (2006.01)
  *G04G 9/00* (2006.01)
  *G04G 21/02* (2010.01)
  *G04G 21/08* (2010.01)

(52) U.S. Cl.
  CPC .............. *A61B 5/282* (2021.01); *A61B 5/332* (2021.01); *A61B 5/339* (2021.01); *G04G 9/0005* (2013.01); *G04G 21/025* (2013.01); *G04G 21/08* (2013.01); *G06F 1/163* (2013.01)

(58) Field of Classification Search
  CPC .. A61B 5/02438; G06F 1/163; G04G 9/0005; G04G 21/025; G04G 21/08
  USPC ........................................................ 600/386
  See application file for complete search history.

(56) References Cited

U.S. PATENT DOCUMENTS

| | | | |
|---|---|---|---|
| 6,428,537 B1 | 8/2002 | Swanson et al. | |
| 6,529,754 B2 | 3/2003 | Kondo | |
| 6,608,562 B1 | 8/2003 | Kimura et al. | |
| 6,996,428 B2 | 2/2006 | Kislov et al. | |
| 7,187,961 B2 | 3/2007 | Yamashita | |
| 7,450,002 B2 | 11/2008 | Choi et al. | |
| 7,486,386 B1 | 2/2009 | Holcombe | |
| 7,598,878 B2 | 10/2009 | Goldreich | |
| 7,729,748 B2 | 6/2010 | Florian | |
| 7,822,469 B2 | 10/2010 | Lo | |
| 7,894,888 B2 | 2/2011 | Chan et al. | |
| 7,915,601 B2 | 3/2011 | Setlak et al. | |
| 7,957,762 B2 | 6/2011 | Herz et al. | |
| 8,670,819 B2 | 3/2014 | Iwamiya et al. | |
| 8,758,258 B2 | 6/2014 | Takahashi et al. | |
| 8,842,848 B2 | 9/2014 | Donaldson et al. | |
| 8,954,135 B2 | 2/2015 | Yuen et al. | |
| 8,988,372 B2 | 3/2015 | Messerschmidt et al. | |
| 9,042,971 B2 | 5/2015 | Brumback et al. | |
| 9,024,250 B2 | 6/2015 | Spraggs | |
| 9,100,579 B2 | 8/2015 | Schatvet et al. | |
| 9,348,322 B2 | 5/2016 | Fraser et al. | |
| 9,427,191 B2 | 8/2016 | LeBoeuf | |
| 9,442,570 B2 | 9/2016 | Slonneger | |
| 9,485,345 B2 | 11/2016 | Dantu | |
| 9,506,802 B2 | 11/2016 | Chu et al. | |
| 9,516,442 B1 | 12/2016 | Dusan | |
| 9,557,716 B1* | 1/2017 | Inamdar | G04G 17/06 |
| 9,620,312 B2 | 4/2017 | Ely et al. | |
| 9,627,163 B2 | 4/2017 | Ely et al. | |
| 9,664,556 B2 | 5/2017 | Chu et al. | |
| 9,687,165 B2* | 6/2017 | Katra | A61B 5/7203 |
| 9,723,997 B1 | 8/2017 | Lamego | |
| 9,737,221 B2 | 8/2017 | Sato | |
| 9,763,584 B2 | 9/2017 | Freschl et al. | |
| 9,772,605 B2 | 9/2017 | Shim et al. | |
| 9,775,548 B2 | 10/2017 | Sarantos | |
| 9,833,159 B2 | 12/2017 | Chu et al. | |
| 9,848,823 B2 | 12/2017 | Raghuram et al. | |
| 9,852,844 B2 | 12/2017 | Golko et al. | |
| 9,891,590 B2 | 2/2018 | Shim et al. | |
| 9,971,399 B2 | 5/2018 | Lee | |
| 10,058,773 B2 | 8/2018 | Huang | |
| 10,123,710 B2 | 11/2018 | Gassoway et al. | |
| 10,126,194 B2 | 11/2018 | Lee | |
| 10,271,800 B2 | 4/2019 | Lin et al. | |
| 10,488,936 B2 | 11/2019 | Baranski | |
| 10,524,720 B2 | 1/2020 | Newberry | |
| 10,551,929 B2 | 2/2020 | Kim | |
| 10,671,222 B2 | 6/2020 | Kuboyama et al. | |
| 2003/0045802 A1 | 3/2003 | Kato | |
| 2006/0069319 A1 | 3/2006 | Elhag et al. | |
| 2009/0265671 A1 | 10/2009 | Sachs et al. | |
| 2011/0015496 A1 | 1/2011 | Sherman et al. | |
| 2013/0310656 A1 | 11/2013 | Lim | |
| 2014/0073486 A1* | 3/2014 | Ahmed | A61B 5/02427 482/9 |
| 2014/0107493 A1* | 4/2014 | Yuen | A61B 5/6898 600/473 |
| 2014/0275832 A1 | 9/2014 | Muehlsteff et al. | |
| 2015/0002088 A1 | 1/2015 | D'Agostino | |
| 2015/0041289 A1* | 2/2015 | Ely | G06F 1/163 200/4 |
| 2016/0058309 A1 | 3/2016 | Han | |
| 2016/0058375 A1* | 3/2016 | Rothkopf | G06F 1/163 600/323 |
| 2016/0120472 A1 | 5/2016 | Kub et al. | |
| 2016/0198966 A1 | 7/2016 | Uernatsu et al. | |
| 2016/0242659 A1 | 8/2016 | Yamashita et al. | |
| 2016/0338598 A1* | 11/2016 | Kegasawa | A61B 5/681 |
| 2016/0338642 A1 | 11/2016 | Parara et al. | |
| 2016/0349803 A1 | 12/2016 | Dusan | |
| 2016/0370873 A1* | 12/2016 | Shipman | G06F 3/0202 |
| 2016/0378071 A1 | 12/2016 | Rothkopf | |
| 2017/0011210 A1 | 1/2017 | Cheong et al. | |
| 2017/0038877 A1* | 2/2017 | Kuboyama | G06F 3/045 |
| 2017/0049332 A1* | 2/2017 | Park | A61B 5/4866 |
| 2017/0090599 A1* | 3/2017 | Kuboyama | G06F 3/03547 |
| 2017/0181644 A1* | 6/2017 | Meer | A61B 5/02438 |
| 2017/0230754 A1 | 8/2017 | Dusan | |
| 2017/0296088 A1 | 10/2017 | Choi | |
| 2017/0354332 A1 | 12/2017 | Lamego | |
| 2018/0020937 A1* | 1/2018 | Chou | A61B 5/4806 600/301 |
| 2018/0220972 A1* | 8/2018 | Jeong | A61B 5/7445 |
| 2018/0235483 A1 | 8/2018 | Mouradian | |
| 2018/0235542 A1 | 8/2018 | Yun et al. | |
| 2019/0025438 A1* | 1/2019 | Venkatraman | G01C 21/20 |
| 2019/0090806 A1 | 3/2019 | Harrison-Noonan et al. | |
| 2019/0101870 A1 | 4/2019 | Pandya et al. | |
| 2019/0209031 A1* | 7/2019 | Ariyama | A61B 5/0082 |
| 2019/0220069 A1 | 7/2019 | Dusan | |
| 2020/0100684 A1 | 4/2020 | Lamego | |
| 2020/0229761 A1 | 7/2020 | Pandya et al. | |
| 2020/0233381 A1 | 7/2020 | Yang et al. | |
| 2020/0356146 A1 | 11/2020 | Dusan | |
| 2021/0014617 A1 | 1/2021 | Dusan | |
| 2021/0204876 A1 | 7/2021 | Pandya et al. | |

FOREIGN PATENT DOCUMENTS

| | | |
|---|---|---|
| CN | 102246125 | 11/2011 |
| CN | 102483608 | 5/2012 |
| CN | 102867190 | 1/2013 |
| CN | 203732900 | 7/2014 |
| CN | 104050444 | 9/2014 |
| CN | 204515353 | 7/2015 |
| CN | 105339871 | 2/2016 |
| CN | 205041396 | 2/2016 |
| CN | 205121417 | 3/2016 |
| CN | 105556433 | 5/2016 |
| CN | 105955519 | 9/2016 |
| CN | 106236051 | 12/2016 |
| CN | 106388809 | 2/2017 |
| CN | 106462665 | 2/2017 |
| CN | 206209589 | 5/2017 |
| CN | 206324777 | 7/2017 |
| JP | 2001145607 | 5/2001 |
| JP | 2009519737 | 5/2009 |
| JP | 2016148657 | 8/2016 |
| KR | 1020090099147 | 9/2009 |
| KR | 20110012784 | 2/2011 |
| KR | 1020160041553 | 4/2016 |
| KR | 1020160145284 | 12/2016 |
| TW | 201610621 | 3/2016 |
| TW | 201621491 | 6/2016 |
| TW | 201632136 | 9/2016 |
| WO | WO 15/030712 | 3/2015 |

(56) References Cited

FOREIGN PATENT DOCUMENTS

| WO | WO 16/036747 | 3/2016 |
|----|--------------|--------|
| WO | WO 16/040392 | 3/2016 |
| WO | WO 16/204443 | 12/2016 |

OTHER PUBLICATIONS

U.S. Appl. No. 16/193,836, filed Nov. 16, 2018, Pandya et al.
International Search Report and Written Opinion dated Nov. 20, 2018, PCT/US2018/048971, 12 pages.
Onizuka et al., Head Ballistocardiogram Based on Wireless Multi-Location Sensors, 2015 EEE, pp. 1275-1278.
Dozza et al., "A Portable Audio-biofeedback System to Improve Postural Control," Proceedings of the 26th Annual International Conference of the IEEE EMBS, San Francisco, CA, Sep. 1-5, 2004, pp. 4799-4802.
Chen et al., "Dynamics Analysis and Simulation of the Wearable Power Assistance Robot," Experiment Science and Technology, 2009, 5 pages.
Nirjon et al., MusicalHeart: A Hearty Way of Listening to Music, SenSys 2012, Nov. 6-9, 2012, Toronto, Ontario, Canada, pp. 1-14.
Ohgi et al., "Stroke phase discrimination in breaststroke swimming using a tri-axial acceleration sensor device," *Sports Engineering*, vol. 6, No. 2, Jun. 1, 2003, pp. 113-123.
Zijlstra et al., "Assessment of spatio-temporal gait parameters from trunk accelerations during human walking," *Gait & Posture*, vol. 18, No. 2, Oct. 1, 2003, pp. 1-10.

* cited by examiner

WEARABLE ELECTRONIC DEVICE WITH ELECTRODES FOR SENSING BIOLOGICAL PARAMETERS

CROSS-REFERENCE TO RELATED APPLICATIONS

This application claims the benefit under 35 U.S.C. § 119(e) of U.S. Provisional Patent Application No. 62/554,196, filed on Sep. 5, 2017, and entitled "Wearable Device with Electrodes for Sensing Biological Parameters," and U.S. Provisional Patent Application No. 62/644,886, filed on Mar. 19, 2018, and entitled "Wearable Device with Electrodes for Sensing Biological Parameters," the contents of which are incorporated herein by reference as if fully disclosed herein.

FIELD

The described embodiments relate generally to an electronic watch or other wearable electronic device. More particularly, the described embodiments relate to techniques for providing, on a watch or other wearable electronic device, electrodes for sensing biological parameters. The electrodes may be variously provided on a surface of an optical component, crown, button, or housing member of the watch or other wearable electronic device.

BACKGROUND

A wearable electronic device may include a set of sensors for determining a set of biological parameters of a user that wears the wearable electronic device. Circuitry associated with the set of sensors may generate, for example, electrical signals or measurements corresponding to voltages at, forces applied to, or amounts of light incident on, the sensors. The various signals or measurements may be correlated to, or used to derive, various biological parameters of the user, such as a heart rate of the user.

SUMMARY

Embodiments of the systems, devices, methods, and apparatuses described in the present disclosure are directed to an electronic watch or other wearable electronic device having a set of electrodes that may be used to sense or determine biological parameters of a user that wears the wearable electronic device. The biological parameters may include, for example, an electrocardiogram (ECG) of the user.

One embodiment takes the form of an electronic watch, comprising: a housing; a crown comprising: a crown body; and a shaft connected to the crown body and passing through the housing; a carrier connected to the housing; a transparent cover connected to the housing; a touch-sensitive display at least partially within the housing and viewable through the transparent cover; a first electrode on the carrier; a second electrode on the crown body; and a processor within the housing and operationally connected to the first electrode and the second electrode; wherein: the first electrode is configured to measure a first voltage; the second electrode is configured to measure a second voltage; the processor is configured to determine an electrocardiogram using the first voltage and the second voltage; and the touch-sensitive display is configured to display the electrocardiogram.

Another embodiment takes the form of an electronic watch, comprising: a housing; a carrier attached to the housing; a first electrode on the carrier; a crown extending through the housing and configured to translate and rotate, comprising a second electrode; and a processor operable to determine a biological parameter of a user based on voltages measured at the first electrode and the second electrode; wherein: the voltages are measured while the user is in contact with the first electrode and the second electrode.

Yet another embodiment takes the form of a method for determining and displaying an electrocardiogram by an electronic watch, comprising: measuring a first voltage at a first electrode on a crown of the electronic watch; measuring a second voltage at a second electrode on a carrier of the electronic watch; determining, by a processor of the electronic watch, the electrocardiogram using the first voltage and the second voltage; and displaying the electrocardiogram on a display of the electronic watch.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to techniques for distributing a set of electrodes over a set of surfaces of a wearable electronic device, such as an electronic watch, and to techniques for electrically isolating the electrodes from other components of the device and/or mitigating effects of environmental factors when sensing voltages or signals indicative of one or more biological parameters of a user who is in contact with the electrodes, and to techniques for routing the voltages or signals within the device.

Embodiments further may take the form of an electronic watch, or other portable and/or wearable device, configured to detect an electrocardiogram ("ECG") of a person wearing or otherwise interacting with the electronic device. As one non-limiting example, a person may wear an electronic watch that has two external electrodes configured to be touched by the user. A first electrode may be placed on a rear surface of the watch and be in contact with skin on the wrist of the person. A second electrode may be defined by or on a crown of the watch and may be configured to be touched by a finger (or other body part) of the person.

Figure 1A:
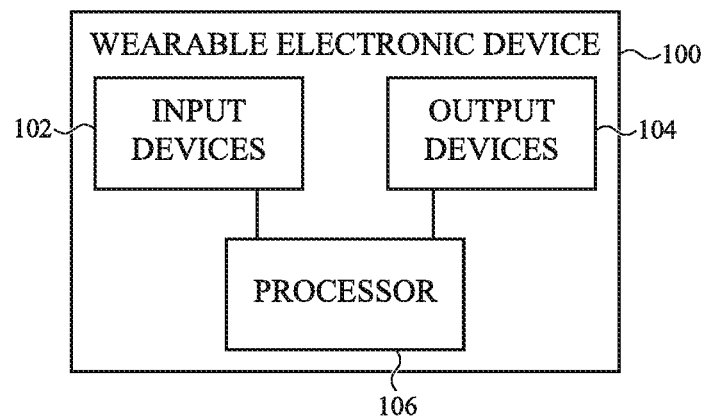
FIG. 1A shows a functional block diagram of a wearable electronic device.

FIG. 1A shows a functional block diagram of a wearable electronic device 100. In some examples, the device 100 may be an electronic watch or electronic health monitoring device. The wearable electronic device 100 may include one or more input devices 102, one or more output devices 104, and a processor 106. Broadly, the input devices 102 may detect various types of input, and the output devices 104 may provide various types of output. The processor 106 may receive input signals from the input devices 102, in response to inputs detected by the input devices. The processor 106 may interpret input signals received from one or more of the input devices 102 and transmit output signals to one or more of the output devices 104. The output signals may cause the output devices 104 to provide one or more outputs. Detected input at one or more of the input devices 102 may be used to control one or more functions of the device 100. In some cases, one or more of the output devices 104 may be configured to provide outputs that are dependent on, or manipulated in response to, the input detected by one or more of the input devices 102. The outputs provided by one or more of the output devices 104 may also be responsive to, or initiated by, a program or application executed by the processor 106 and/or an associated companion device.

In various embodiments, the input devices 102 may include any suitable components for detecting inputs. Examples of input devices 102 include audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 102 may be configured to detect one or more particular types of input and provide a signal (e.g., an input signal) corresponding to the detected input. The signal may be provided, for example, to the processor 106.

The output devices 104 may include any suitable components for providing outputs. Examples of output devices 104 include audio output devices (e.g., speakers), visual output devices (e.g., lights or displays), tactile output devices (e.g., haptic output devices), communication devices (e.g., wired or wireless communication devices), and so on, or some combination thereof. Each output device 104 may be configured to receive one or more signals (e.g., an output signal provided by the processor 106) and provide an output corresponding to the signal.

The processor 106 may be operably coupled to the input devices 102 and the output devices 104. The processor 106 may be adapted to exchange signals with the input devices 102 and the output devices 104. For example, the processor 106 may receive an input signal from an input device 102 that corresponds to an input detected by the input device 102. The processor 106 may interpret the received input signal to determine whether to provide and/or change one or more outputs in response to the input signal. The processor 106 may then send an output signal to one or more of the output devices 104, to provide and/or change outputs as appropriate. Examples of suitable processors are discussed in more detail below with respect to FIG. 25.

In some examples, the input devices 102 may include a set of electrodes. The electrodes may be disposed on one or more exterior surfaces of the device 100. The processor 106 may monitor for voltages or signals received on at least one of the electrodes. In some embodiments, one of the electrodes may be permanently or switchably coupled to a device ground. The electrodes may be used to provide an ECG function for the device 100. For example, a 2-lead ECG function may be provided when a user of the device 100 contacts first and second electrodes that receive signals from the user. As another example, a 3-lead ECG function may be provided when a user of the device 100 contacts first and second electrodes that receive signals from the user, and a third electrode that grounds the user to the device 100. In both the 2-lead and 3-lead ECG embodiments, the user may press the first electrode against a first part of their body and press the second electrode against a second part of their body. The third electrode may be pressed against the first or second body part, depending on where it is located on the device 100.

Figure 1B:
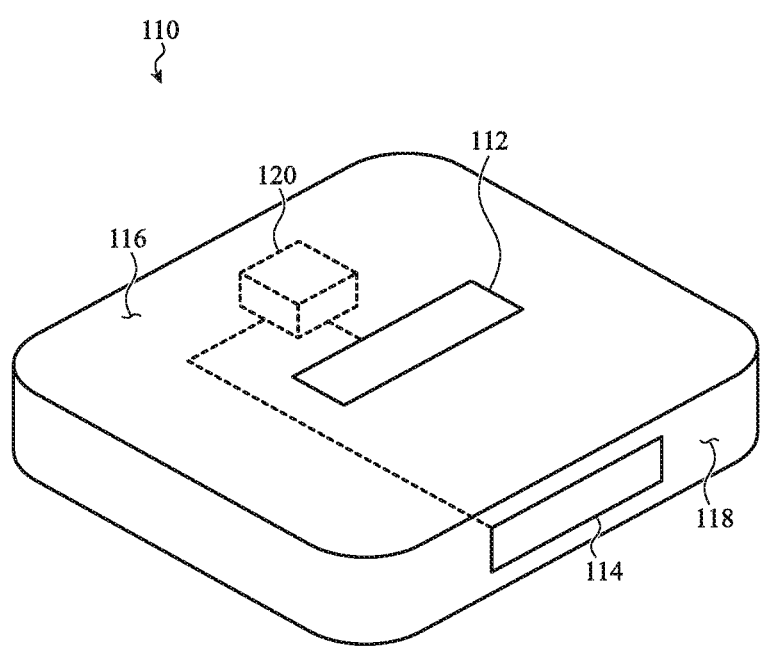
FIG. 1B shows an example of an electronic device having a set of electrodes disposed thereon.

FIG. 1B shows an example of an electronic device 110 (here, an electronic watch) having a set of electrodes 112, 114 disposed thereon. The device 110 may be an example of the wearable electronic device described with reference to FIG. 1A, or may be an example of an electronic device that is not wearable. In some embodiments, the set of electrodes 112, 114 may be provided on one surface of the device 110. In other embodiments (as shown), the set of electrodes 112, 114 may include electrodes provided on different surfaces of the device 100, such as a first electrode 112 provided on a first surface 116 of the device 110, and a second electrode 114 provided on a second surface 118 of the device 110. Providing electrodes on different surfaces of a device may make it easier for a user to place different body parts in contact with different electrodes. For example, a user may place one or more of the electrodes (e.g., the first electrode 112) in contact with their wrist, and may touch another one or more of the electrodes (e.g., the second electrode 114) with a finger of their opposite hand. Alternatively, the user may press the electrodes 112, 114 against different parts of their body. A processor 120 of the device 110, or a processor remote from the device 110, may determine, from the voltages or signals (e.g., from stored digital samples or values representing the voltages or signals), the biological parameter(s) of the user. The biological parameter(s) may include, for example, an electrocardiogram (ECG) of the user, an indication of whether the user is experiencing atrial fibrillation, an indication of whether the user is experiencing premature atrial contraction or premature ventricular contraction, an indication of whether the user is experiencing a sinus arrhythmia, and so on.

In some embodiments, one or two thin film electrodes may be PVD deposited on an exterior surface of a structure that forms part of a housing of an electronic device. The surface may be any transparent, semi-transparent, translucent, or opaque surface made out of an amorphous solid, glass, a crystal or crystalline material (such as sapphire or zirconia), plastic, or the like. In the case of a watch (i.e., a type of electronic device), an additional electrode may be positioned on a user-rotatable crown of a watch body, on a button of the watch body, or on another surface of a housing that defines the watch body.

When an electrode is formed on a carrier that forms part of a housing of an electronic device, the electrode may be connected to an electrical contact within the electronic device by depositing the electrode material such that it wraps around an edge or perimeter of the carrier, and onto an interior surface of the carrier. The electrical contact may be on the interior surface of the carrier. In other embodiments, the electrode may be formed on the exterior surface of the carrier, and a thru-carrier via that is filled or coated with a conductive material may connect the electrode to an electrical contact within the electronic device. The carrier may be any appropriate structure that supports the electrodes, on which the electrodes are formed, or to which the electrodes are attached. In certain embodiments described herein, the carrier is an optically transparent material having a dome shape. It should be appreciated that the carrier may have different shapes (flat, stepped, parallelepiped, and so on) and may be made from different materials, including opaque materials.

Generally, the term "attached" means that two elements, objects, structures, or objects are separate but affixed or retained to one another, whether removably, as with an electronic device attached to a user by a band, or fixedly, as with two elements that are affixed to one another with a mechanical fastener not meant to be decoupled (a screw, bolt, or the like), by an adhesive, by plating or depositing one material on another (as with an electrode deposited on the carrier), and so on. The term "connected" means that two elements may be attached to one another, or may be two parts of a unitary whole (as with a shaft and crown body formed from the same material as a single piece). Thus, while two elements that are attached to one another are necessarily connected to one another, the reverse is not necessarily true. For example, two elements may be formed as a single piece or part and thus connected to one another, although they are not attached to one another.

When an electrode is provided on a crown of an electronic device, the crown may be conductive or have a conductive surface, and the conductive portion of the crown may be coupled to a conductive rotatable shaft that extends through an opening in a device housing. An end of the shaft interior to the housing, or a conductive shaft retainer interior to the housing, may be in mechanical and electrical contact with a spring-biased conductor that carries electrical signals between the shaft or shaft retainer and a circuit, thereby providing electrical communication between the crown and the circuit.

A processor of an electronic device (e.g., the processor 120) may be operable to determine a biological parameter of a user based on voltages at various electrodes (e.g., at the set of electrodes 112, 114). In some cases, the biological parameter may be an ECG of a user of the electronic device. For example, when a watch has a first electrode on an exterior surface of a carrier and a second electrode on a crown, the user's fastening of the watch to their wrist may place the first electrode in contact with skin on the user's wrist. To acquire an ECG, the user may touch a conductive portion of the crown with a finger on their opposite hand. For example, the carrier or housing of the watch may touch a wrist adjacent one hand, and the crown may be touched with a finger of the opposite hand. In some cases, the watch may have a third electrode, also on the exterior surface of the carrier, which grounds the user to the watch. The third electrode may be used to reject noise from ECG signals. The electrodes may be positioned on different surfaces, or different portions of surfaces, in various embodiments.

The electrode(s) on the exterior surface of the carrier may be positioned at the periphery of the carrier, or otherwise positioned to enable an optical sensor subsystem to emit and receive light through the carrier. The light may be emitted into, and reflected from, a user's skin to determine other biological parameters of the user, such as a heart rate, blood pressure, pulse, blood oxygenation, glucose level, and so on.

These and other embodiments are discussed with reference to FIGS. 1-25. However, those skilled in the art will readily appreciate that the detailed description given herein with respect to these figures is for explanatory purposes only and should not be construed as limiting.

Figure 2A:
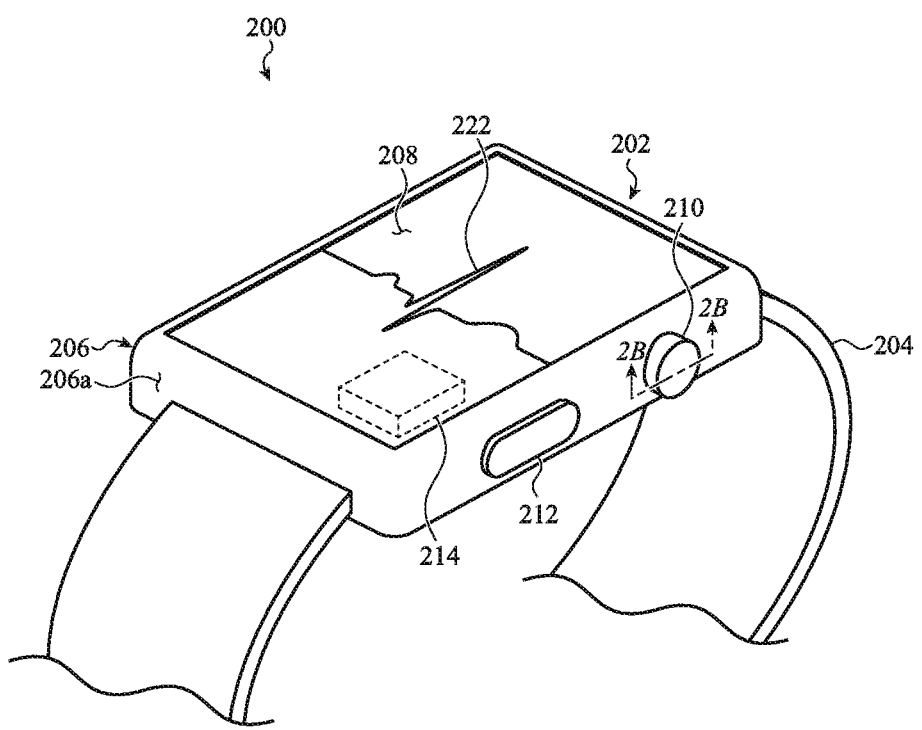
FIGS. 2A-2C show an example of an electronic watch that incorporates a set of electrodes.
Figure 2B:
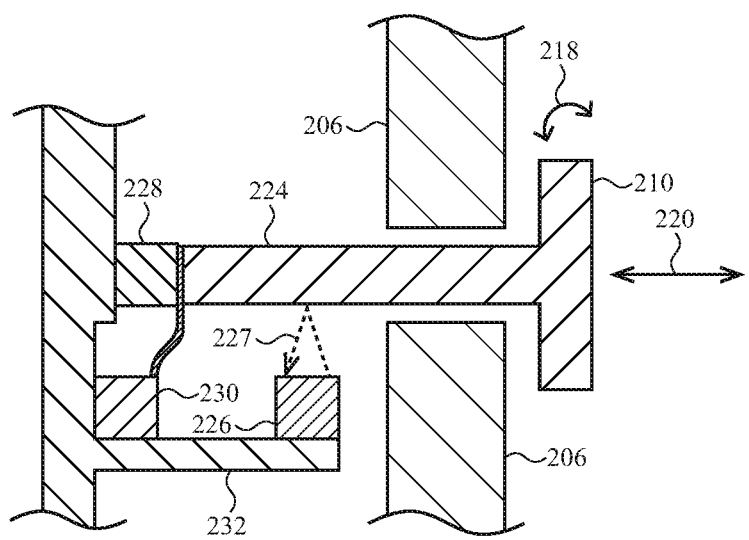
Figure 2C:
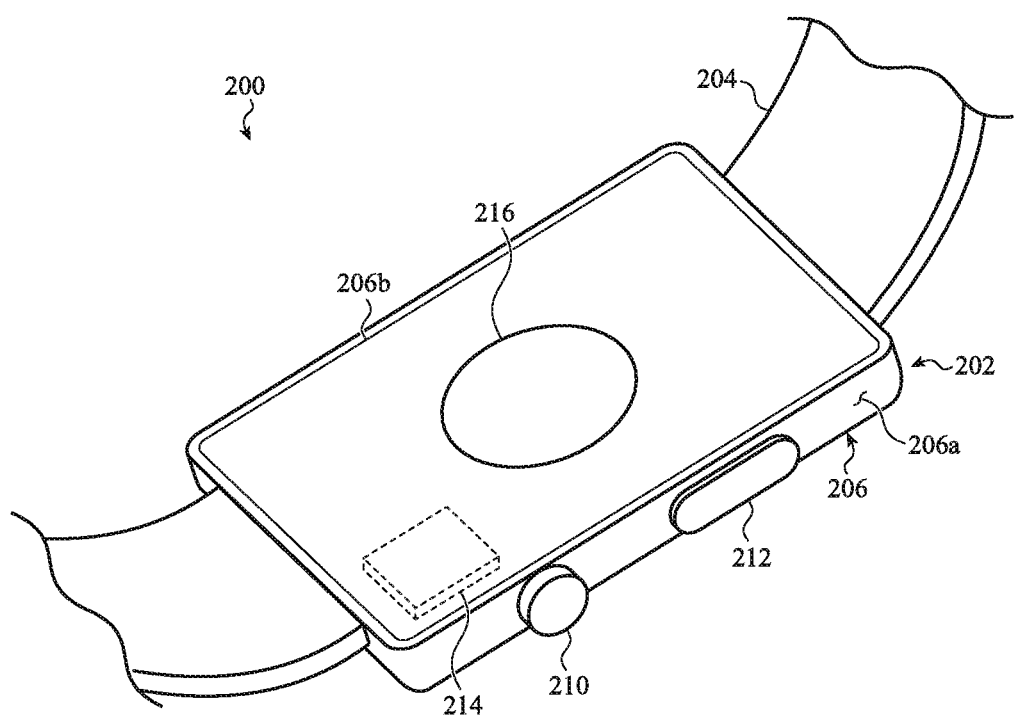

FIGS. 2A-2C show an example of an electronic watch 200 that incorporates a set of electrodes. The watch 200 may be an example of the wearable electronic device 100 or 110 described with reference to FIG. 1A or 1B. The watch 200 may include a watch body 202 and a watch band 204. The watch body 202 may include an input or selection device, such as a crown 210 or a button 212. FIG. 2A shows an isometric view of the watch body's front face. FIG. 2B shows an example cross-section of the crown 210. FIG. 2C shows an isometric view of the watch body's rear face. In FIGS. 2A & 2C, only a portion of the watch band 204 is shown (i.e., only the portions of the watch band 204 that attach to the watch body 202).

The watch body 202 may include a housing 206. The housing 206 may include a front side housing member 206a that faces away from a user's skin when the watch 200 is worn by a user (see FIG. 2A), and a back side housing member 206b (or rear cover) that faces toward the user's skin (see FIG. 2C). Alternatively, the housing 206 may include a singular housing member, or more than two housing members. The one or more housing members may be metallic, plastic, ceramic, crystal, or other types of housing members (or may include combinations of such materials).

As shown in FIG. 2A, a transparent cover 208 may be attached to a front side of the watch body 202 (i.e., facing away from a user's skin), over or within an opening in the housing 206, and may protect a display positioned at least partially within the housing 206. The display may be viewable by a user through the cover 208. In some embodiments, the display may depict an ECG waveform of a person who is wearing or otherwise using the watch 200. In some cases, the cover 208 may be part of a display stack, which display stack may include a touch sensing or force sensing capability. The display may be configured to depict a graphical output of the watch 200, and a user may interact with the graphical output (e.g., using a finger or stylus that touches or hovers over the cover 208, or using the crown 210 or button 212). As one example, the user may select (or otherwise interact with) a graphic, icon, indicator, message, or the like (collectively, "graphic") presented on the display by touching or pressing on the display at the location of the graphic. In some embodiments, the user may receive confirmation of their selection by means of haptic output provided by the watch body 202 through the display or cover 208. The exterior surface of the cover 208 may therefore function as a means for receiving input (i.e., function as an input device) and a means for providing output (i.e., function as an output device). The cover 208 may be attached to the housing 206 or part of the housing 206 (e.g., connected to the housing). In some embodiments, the cover 208 may be considered part of the housing 206 because it forms part of an outer shell that defines an interior volume (or houses internal components) of the watch body 202. In some examples, the cover 208 may be or include a crystal, such as a sapphire crystal. Alternatively, the cover 208 may be formed of glass, plastic, or other materials.

The watch body 202 may include at least one input device or selection device, such as a crown 210, scroll wheel, knob, dial, button 212, or the like, which input device may be operated by a user of the watch 200. In some embodiments, the crown 210, scroll wheel, knob, dial, button 212, or the like may be conductive, or have a conductive surface, and a signal route may be provided between the conductive portion of the crown 210, scroll wheel, knob, dial, button 212, or the like and a circuit (including a processor) within the watch body 202.

The operation of determining and/or displaying a user's ECG may be initiated by rotating the crown 210, translating the crown, tilting the crown, touching the crown, and so on. Likewise the operation of determining the ECG may be initiated by interacting with a touch-sensitive cover 208 or display of the electronic watch. As discussed above, the display may be partially or fully within the housing of the electronic watch.

Turning primarily to FIG. 2B, it is shown that the housing 206 may include an opening through which a shaft 224 extends. A crown 210 may be connected to the shaft 224, and may be accessible to a user exterior to the housing 206. The crown 210 may be manipulated by a user to rotate or translate the shaft, as indicated by arrows 218 and 220. Such manipulations are examples of crown inputs. The shaft may be mechanically, electrically, magnetically, and/or optically coupled to components within the housing 206. In some embodiments, the crown 210 may be part of a crown assembly, as described with reference to FIG. 11, 12A, 12B, 13, or 14.

A user's manipulation of the crown 210 (and thus the shaft 224) may be used to manipulate or select various textual or graphical elements displayed by the watch 200, to adjust a volume of a speaker, to turn the watch 200 on or off, and so on. In some embodiments, the crown 210 may be manipulated (e.g., rotated or pressed) to select or activate a health monitoring function of the watch 200 (e.g., an ECG or other heart monitoring function). For example, a user may rotate the crown to select an ECG application, and may press the crown to activate the ECG application (e.g., initiate determination and display of a wearer's ECG). Alternatively, a user's touch or press of the crown (or touch or press of the crown for a predetermined period of time) may activate the ECG application and cause a heart rhythm of the user to be displayed. As yet another example, the user may interact with the touch-sensitive display to select and/or activate the ECG application. By way of example, a user's activation of an ECG application is indicated by the watch's display of the ECG 222 in FIG. 2A. Alternatively, the user's selection of an ECG application may be indicated by another graphic or text displayed by the watch 200. Generally, the watch 200 (and specifically its display) may change from displaying some graphic or text to displaying the ECG 222 once the ECG (or its corresponding application, or function) is initiated, selected, or determined.

As shown in FIG. 2B, the crown 210 may be connected to the shaft 224 (and may be unitary with the shaft), and the shaft 224 may extend through an opening in the housing 206. In some embodiments, the shaft 224 may be separated from the housing 206 by a bushing or other component, or retained to the housing 206 by a retention mechanism. The shaft 224 may rotate or translate with respect to the housing 206, as indicated by arrows 218 and 220, thereby providing one or more crown inputs to a processor of the electronic device 200. A first sensor 226 within the housing 206 may sense aspects of shaft movement such as direction of rotation, speed of rotation, rotational acceleration, or angular position of the shaft 224. In some embodiments, the first sensor 226 may be an optical sensor positioned adjacent the shaft 224, such that light 227 is emitted onto, and reflected from, the shaft 224. Light 227 may be reflected from the shaft by a pattern of surface features (such as scallops, grooves, indentation, projections, or the like) or by byproducts of machining the shaft, such as bumps, scratches, irregularities, and so on. The pattern and speed of light 227 reflected onto the optical sensor 226 maybe used to determine a direction and/or speed of rotation of the shaft 224. In other embodiments, different sensors may be used to detection direction and/or speed of rotation of the shaft 224, including mechanical sensors, electrical sensors, capacitive sensors, brush contacts, magnetic sensors, and so on.

A second sensor 228 within the housing 206 may sense aspects of shaft movement such as translation or direction of translation. In some embodiments, the second sensor 228 may be a tactile switch, optical sensor, magnetic sensor, capacitive sensor or the like positioned at an end of the shaft 224.

A third sensor 230 within the housing 206 may sense when a user is touching the crown 210, or may sense signals (e.g., a heart rhythm) received by the crown 210 when a user touches the crown 210. In some embodiments, the third sensor 230 may be electrically coupled to the crown 210 or shaft 224. In some cases, the sensors 226, 228, 230 may be provide signals or information to the processor 214, or may be partly or wholly integrated with the processor 214 or other components of the watch 200. In some embodiments, two or more of the sensors 226, 228, 230 may be combined into a multipurpose sensor. In some embodiments, one or more of the sensors 226, 228, 230 may not be provided. In some embodiments, the functions of one of the sensors 226, 228, 230 may be distributed among multiple sensors, or additional crown sensors may be provided.

Any or all of the first sensor 226, second sensor 228, and third sensor 230 may be attached to or otherwise supported by one or more internal supports 232, as shown in FIG. 2B.

Turning primarily to FIG. 2C, the housing 206 may include structures for attaching the watch band 204 to the watch body 202. In some cases, the structures may include elongate recesses or openings through which ends of the watch band 204 may be inserted and attached to the watch body 202. In other cases (not shown), the structures may include indents (e.g., dimples or depressions) in the housing 206, which indents may receive ends of spring pins that are attached to or threaded through ends of a watch band to attach the watch band to the watch body 202.

The watch band 204 may be used to secure the watch 200 to a user, another device, a retaining mechanism, and so on.

As previously mentioned, the watch 200 may include a set of electrodes. The set of electrodes may be configured, in some cases, as described with reference to FIG. 1A or 1B. The set of electrodes may be used by a processor 214 that is internal to the watch body 202, to sense biological parameters (e.g., an ECG) of a person who wears the watch 200 and presses the electrodes against their skin. In some embodiments, the set of electrodes may include a rear-facing electrode 216 on the back of the watch body 202 (e.g., on the back side housing member 206b). The set of electrodes may also include an electrode on the crown 210 and/or an electrode on the button 212.

The rear-facing electrode 216 may be formed (e.g., printed, plated, or otherwise deposited) on the back side housing member 206b. If the back side housing member 206b is non-conductive, the rear-facing electrode 216 may be formed directly on the back side housing member 206b and connected to circuitry internal to the watch body 202 (e.g., the processor 214) by, for example, conductive vias formed through the back side housing member 206b. If the back side housing member 206b is conductive, the rear-facing electrode 216 may be separated from the back side housing member 206b by an insulator or insulating layer, and conductive vias formed through the back side housing member 206b may likewise be insulated from the back side housing member 206b. Alternatively, the back side housing member 206b may have an opening to which the rear-facing electrode 216 is mated. In some embodiments, the opening may define a ledge in the back side housing member 206b, and the rear-facing electrode 216 may rest on the ledge (and in some cases may be separated from the back side housing member 206b by an insulator (e.g., a seal) or an insulating layer).

The electrode(s) on the crown 210 or button 212 may be conductive surfaces of the crown 210 or button 212. In some cases, the crown 210 or button 212 may be conductive over its entire exterior surface. In other cases, the crown 210 or button 212 may have conductive portions (e.g., cores or inserts). When the front side housing member 206a is conductive, the crown 210 or button 212 (or the conductive components thereof) may be insulated from the front side housing member 206a by an insulator (e.g., a set of seals, non-conductive coatings, and so on).

In some embodiments, one of the crown 210 or button 212 may have an electrode thereon, and a user wearing the watch 200 on one of their wrists may touch the electrode on the crown 210 or button 212 with a finger of their opposite hand. The processor 214 may then use the electrodes to acquire an ECG for the user. In other embodiments, both the crown 210 and the button 212 may have an electrode thereon, and a user wearing the watch 200 on one of their wrists may touch the electrodes on the crown 210 and button 212 with a finger of their opposite hand. In still other embodiments, the entirety of the back side housing member 206b (or even the entirety of the housing 206) may be an electrode. In these latter embodiments, electrical isolation may be provided between the housing 206 and the crown 210 and/or between the housing 206 and the button 212.

In some examples, the watch 200 may lack the display, the crown 210, or the button 212. For example, the watch 200 may include an audio input or output interface, a touch input interface, a haptic (force) input or output interface, or other input or output interface that does not require the display, crown 210, or button 212. The watch 200 may also include the afore-mentioned input or output interfaces in addition to the display, crown 210, or button 212. When the watch 200 lacks the display, the front face of the watch 200 may be covered by the cover 208, or by a metallic or other type of housing member (e.g., the opening for the cover 208 may not exist, and the front side housing member 206a may extend over the area defined by the cover 208). In these embodiments, the electrode(s) on the crown 210 or button 212 may be replaced by (or supplemented with) an electrode on the front face of the watch body 202. A user may touch the front-facing electrode with a finger, similarly to how they would touch an electrode on the crown 210 and/or button 212. Alternatively, a user could place the front-facing electrode in contact with, for example, an opposite wrist, part of their leg, or their torso or forehead.

In some embodiments, the watch 200 may lack the rear-facing electrode 216, and each of the crown 210 and the button 212 may have a conductive surface that serves as an electrode. In these embodiments, the watch 200 may need to be removed from a user's wrist to enable the user to press different parts of their body against the crown and button electrodes. In some embodiments, the crown 210 or the button 212 may be moved to an opposite side of the watch body 202, thereby increasing the separation between the crown 210 and the button 212 and making it easier for a user to press different parts of their body against the crown and button electrodes.

Other electronic devices that may incorporate a set of electrodes include other wearable electronic devices, other timekeeping devices, other health monitoring or fitness devices, other portable computing devices, mobile phones (including smart phones), tablet computing devices, digital media players, or the like.

Because the voltages or signals provided at, propagated from, or monitored at the various electrodes of a set electrodes may be low voltage or have low amplitudes, the materials, positions, electrical connections to, and electrical routing paths for the set of electrodes can have a significant impact on a processor's ability to discern useful signals representing an ECG or other biological parameter of a person wearing the watch 200 or a similar device (e.g., one of the other watches or electronic devices described herein). The materials, positions, electrical connections to, and electrical routing paths for the set of electrodes can determine how well the electrodes receive voltages/signals from the person's skin (e.g., a signal-to-noise ratio (SNR) of a device-to-user interface through which the voltages/signals pass); how well voltages/signals are transferred between the electrodes and internal components of the watch 200 (e.g., a voltage/signal propagation SNR); and how well the electrodes operate in the face of environmental factors, such as temperature, humidity, moisture, electromagnetic radiation, dust, and so on. Techniques described in the present disclosure may improve the usability of a set of electrodes under some or all of these conditions.

Figure 3:
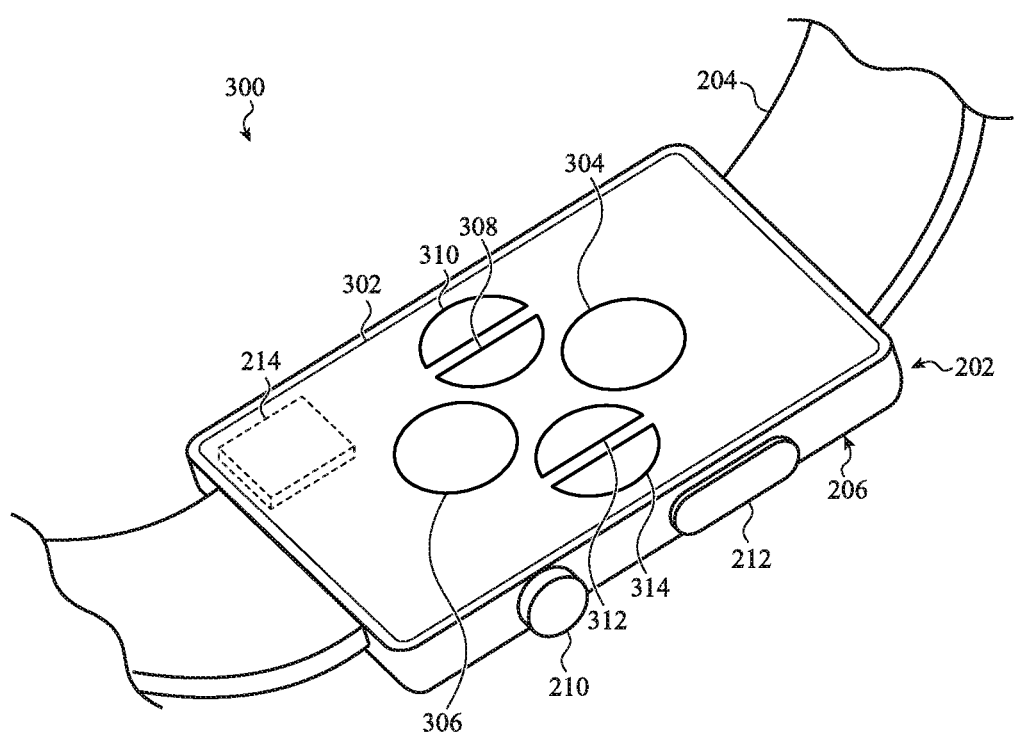
FIG. 3 shows another example of an electronic watch that incorporates a set of electrodes.

FIG. 3 shows another example of an electronic watch 300 that incorporates a set of electrodes. The watch 300 may be an example of the wearable electronic device 100 or 110 described with reference to FIG. 1 or 1B, and may include many of the components of the watch 200 described with reference to FIGS. 2A-2C. The watch 300 may include a watch body 202 and a watch band 204. FIG. 3 shows an isometric view of the watch body's rear face. Only a portion of the watch band 204 is shown (i.e., only the portions of the watch band 204 that attach to the watch body 202).

The watch 300 in FIG. 3 differs from the watch 200 of prior figures in that it has a different set of internal components, a different back side housing member 302, and a different set of elements that are provided or exposed on the back side housing member 302. For example, the watch 300 may include a sensor subsystem that includes both electrical and optical components. The electrical components may include one or more electrodes 304, 306 formed on the back side housing member 302. In some cases, each of the electrodes 304, 306 may have a circular shape and may be PVD deposited on the back side housing member 302. Alternatively, only one, or more than two electrodes may be formed on the back side housing member 302, or the electrodes 304, 306 may be positioned over (or inset into) openings in the back side housing member 302.

The optical components of the sensor system may include a set of one or more windows 308, 310, 312, 314 in the back side housing member 302. Each of the windows 308, 310, 312, 314 may pass at least one wavelength of light. In some cases, each of the windows 308, 310, 312, 314 may have a semicircular shape. The windows may alternatively have other shapes. The windows may be formed of crystal, glass, plastic or another material that passes at least one wavelength of light emitted or received by the sensor subsystem.

In some embodiments, the back side housing member 302 may be or include a transparent cover (e.g., a cover including a crystal, such as a sapphire crystal, or glass, or plastic, or the like), and may be substantially flat or planar (as shown) or may be curved or otherwise non-planar. A mask (e.g., an ink mask and/or dark mask) may be applied to the transparent cover to define the windows 308, 310, 312, 314. The electrodes 304, 306 may be formed on top of the mask or over openings in the mask.

In some embodiments, the back side housing member 302 may be an opaque substrate, such as a metal or plastic substrate, and one or more transparent windows 308, 310, 312, 314 may be fitted to openings in the substrate. The transparent windows may be fitted to the openings internally to (or externally from) the watch body 202. The electrodes 304, 306 may be fitted to additional openings that enable the electrodes 304, 306 to protrude outward from the external surface of the back side housing member 302, or the electrodes 304, 306 may be formed on the surface of the back side housing member 302 and the electrically connected to components internal to the watch body 202 by conductive vias or other elements formed through the surface of the back side housing member 302.

By way of example, FIG. 3 shows the electrodes 304, 306 aligned along a first axis that divides the back side housing member 302 into two halves, and shows the windows 308, 310, 312, 314 aligned along a second axis, perpendicular to the first axis, that divides the back side housing member 302 into a different two halves. In this manner, the electrodes 304, 306 and windows 308, 310, 312, 314 may form four circular areas on the exterior surface of the back side housing member 302, with the circular areas that contain the windows 308, 310, 312, 314 appearing bifurcated.

In use, each pair of windows 308/310, 312/314 forming a circular area may include a first window under which one or more light emitters are positioned, and a second window under which one or more light receivers are positioned, with an optional set of one or more light blocking walls positioned between the one or more light emitters and the one or more light receivers (or around the light emitter(s), or around the light receiver(s)).

Figure 4A:
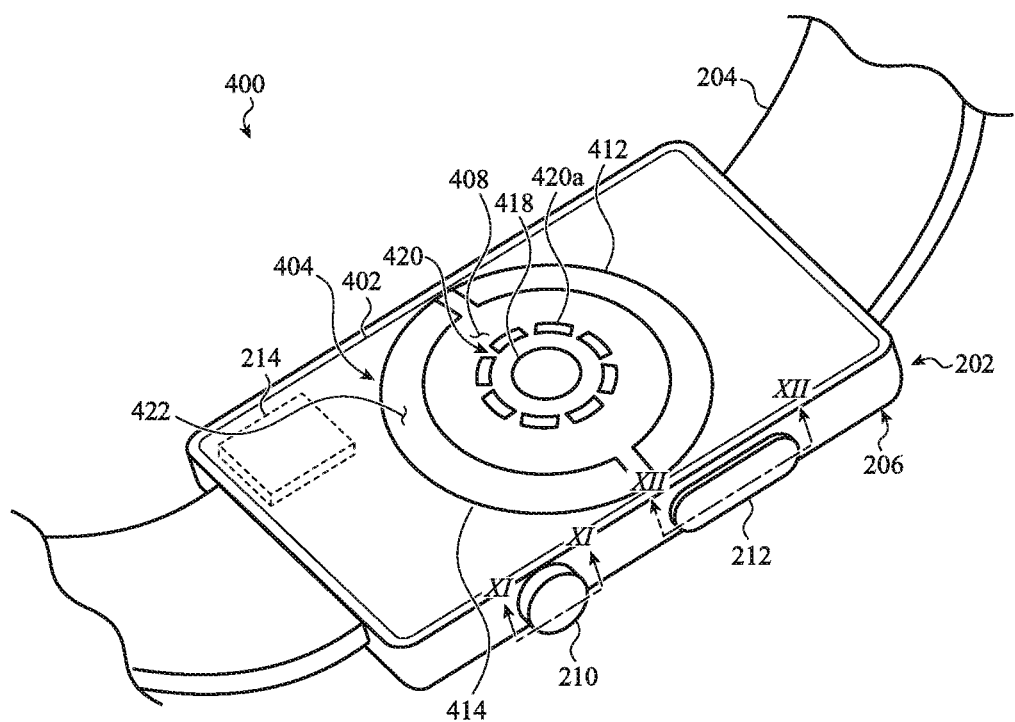
FIGS. 4A-4D show an additional example of an electronic watch that incorporates a set of electrodes on a carrier.

FIGS. 4A-4D show an additional example of an electronic watch 400 that incorporates a set of electrodes. The watch 400 may be an example of the wearable electronic device 100 or 110 described with reference to FIG. 1A or 1B, and may include many of the components of the watch 200 described with reference to FIGS. 2A-2C. The watch 400 may include a watch body 202 and a watch band 204. FIG. 4A shows an isometric view of the watch body's rear face. Only a portion of the watch band 204 is shown (i.e., only the portions of the watch band 204 that attach to the watch body 202).

Similarly to the watch 300 described with reference to FIG. 3, the watch 400 may include a sensor subsystem that includes both electrical and optical components. However, the electrical and optical components of the watch 400 may be arranged differently than the electrical and optical components of the watch 300.

Figure 4B:
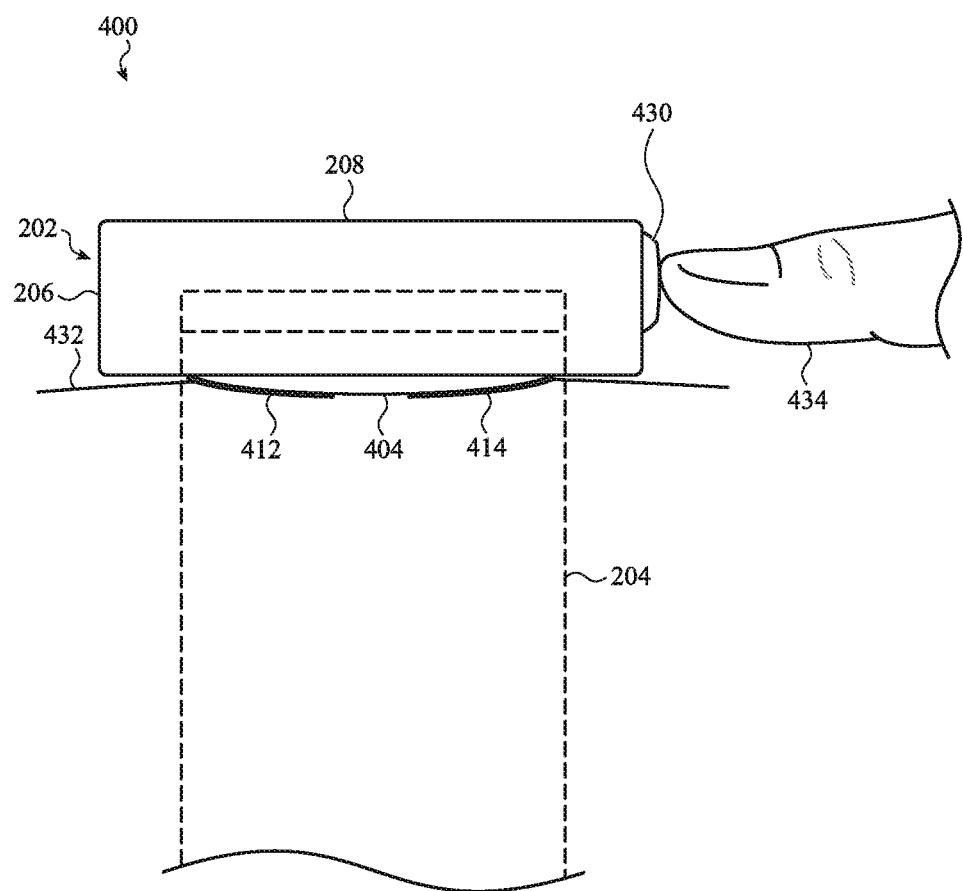
Figure 4C:
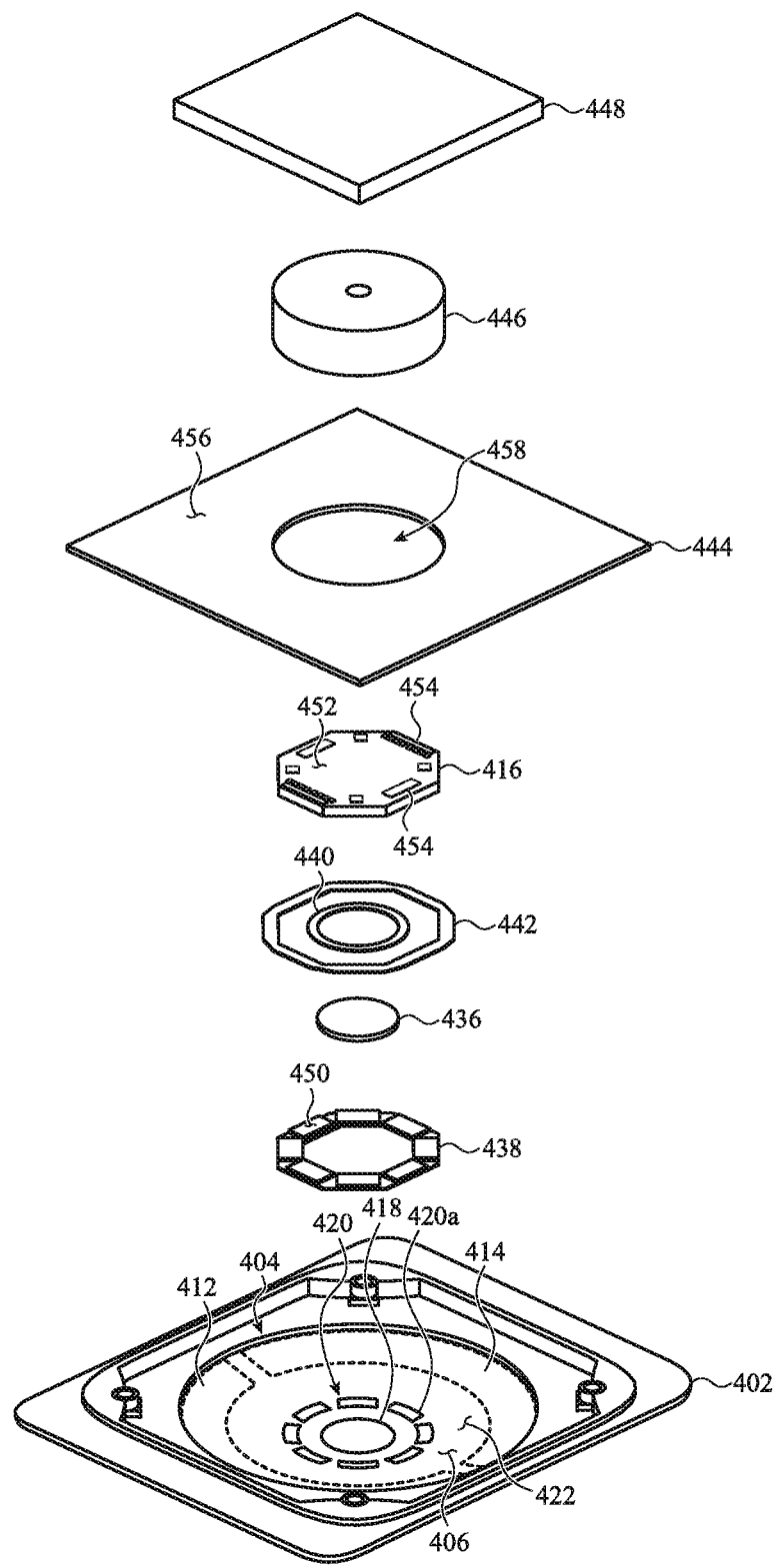

Referring primarily to FIG. 4A, a light-transmissive element such as a carrier 404 (e.g., a rear-facing or skin-facing carrier) may be coupled to or otherwise attached to a back side housing member 402 of the watch 400, and in some cases may be considered to form a part of the housing 206 of the watch body 202. The carrier 404 may have a first surface 406 that is interior to the watch body 202 (see FIG. 4C) and a second surface 408 that is exterior to the watch body 202 (see FIG. 4A). The carrier 404 may be dome-shaped or otherwise non-planar, as shown in FIGS. 4A-4C, such that the second surface 408 protrudes or extends away from a back member 402 of the watch 400. This is best illustrated in FIGS. 4B and 4C.

By way of example, the carrier 404 is shown as having a round perimeter and fitted to a round opening in the back side housing member 402. In other examples, the carrier 404 may have a perimeter that is square, oval, or some other shape. Similarly, the opening in the back side housing member 402 may be square, oval, or some other shape. The perimeter of the carrier 204 and the perimeter of the opening need not have the same size or shape (e.g., the perimeter of the opening in the back side housing member 402 may be smaller or differently shaped than the perimeter of the carrier 404). In some examples, the carrier 404 may be a sapphire crystal. Alternatively, the carrier 404 may be formed from (or replaced by) a light-transmissive element formed of glass, plastic, or another material. The carrier 404 may be transparent to all wavelengths of light or just some wavelengths (and even one wavelength) of light.

The exterior surface 408 of the carrier 404 may have a set of electrodes (e.g., first and second (or rear-facing) electrodes 412, 414) thereon, although in some embodiments a single electrode or more than two electrodes may be used. In some embodiments, the electrodes 412, 414 may be PVD deposited on the carrier 404. Example constructions of the electrodes 412, 414 and masks 422 are described with reference to FIGS. 5A-5E, 6-8, 9A-9C, & 10A-10D. In some embodiments, the electrodes 412, 414 may be opaque. In other examples, the electrodes 412, 414 may be formed of a transparent material, as described with reference to FIG. 6, and the optical sensor subsystem 416 may transmit/receive light through the electrodes 412, 414. The optical sensor subsystem 416 may be, for example, an optical heart rate sensor.

In some cases, the first and second electrodes 412, 414 may be arc-shaped (e.g., semi-circle-shaped), and may be positioned around a central opening 418 and concentric ring of openings 420 formed in the masks 422. The first and second electrodes 412, 414 may extend to the edge of the carrier 404, and in some cases may wrap around the perimeter of the carrier 404 to the interior surface 406 of the carrier 404, or be connected to conductive vias formed in the carrier 404, or otherwise be electrically connected to elements within the watch body 202 that receive a signal sensed by one or both of the first and second electrodes 412, 414. In some cases, the first and second electrodes 412, 414 may be electrically insulated from the back side housing member 402 (e.g., by a non-conductive gasket or adhesive), or the back side housing member 402 may be non-conductive. In some cases, the first and second electrodes 412, 414 may be formed of, or include, stainless steel (SUS) or diamond like carbon (DLC).

The electrodes 412, 414 may be positioned (e.g., at the periphery of the carrier 404 or in other locations) so as not to interfere with optical communication between an optical sensor subsystem 416 interior to the watch body 202 (see FIG. 4C) and a medium (e.g., skin) exterior to the watch body 202. The optical communication may occur through the carrier 404, and in some cases may occur through a number of openings 418, 420 formed in one or more masks 422 applied to the carrier 404. The optical sensing subsystem is discussed in more detail, below.

FIG. 4B shows an elevation of the watch body 202 shown in FIG. 4A. The exterior of the watch body 202 is defined primarily by the housing 206, the transparent cover 208, and the carrier 404. The carrier 404 supports the rear-facing electrodes 412, 414 (e.g., as described with reference to FIGS. 4A, 4C, 5C, 5D, 5E, 6-8, 9A-9C, & 10A-10D). The element 430 may represent the crown 210 or button 212. For ease of explanation, it is noted that the positions of the electrodes 412, 414 on the carrier 404 have been rotated 90 degrees with respect to their positions in FIGS. 4A & 4C.

The watch body 202 may be abutted to a user's wrist 432 or other body part, and may be adhered to the user by the watch band 204 or another element. When abutted to a user's wrist 432, the electrodes 412, 414 on the carrier 404 may contact the user's skin. The user may touch a conductive portion of the element 430 with a finger 434. The user may touch the element 430 in various ways, depending on where the element 430 is conductive, and depending on the user's preference. In some cases, the user may touch the element 430 while also touching their wrist 432. However, high skin-to-skin impedance tends to reduce the likelihood that signals will travel from the electrodes 412, 414, through their wrist 432 to their finger 434, and subsequently to the element 430 (or vice versa). In some cases, the user may touch the element 430 while also touching the housing 206, which may be okay if the housing 206 is not conductive.

FIG. 4C shows an exploded view of components that may be attached to the interior surface 406 of the carrier 404 shown in FIGS. 4A & 4B. When the watch body 202 shown in FIGS. 4A & 4B is assembled, the components shown in FIG. 4C may reside within the housing 206. By way of example, FIG. 4C shows the components in relation to the back side housing member 402 (i.e., in relation to a skin-facing housing member).

In some cases, the interior components shown in FIG. 4C may be attached to (and in some cases directly on) the interior surface 406 of the carrier 404. The interior surface 406 may sometimes be referred to as a first surface of the carrier 404. The components attached to the carrier 404 may include a lens 436, a light filter 438, one or more adhesives 440, 442, the optical sensor subsystem 416, circuitry or a processing subsystem 444, a magnet 446, or a magnetic shield 448.

The lens 436 may abut, be attached to (and optionally, directly on), or be formed on the first or interior surface 406 of the carrier 404. By way of example, the lens 436 is aligned with the center of the carrier 404. In some cases, the interior or exterior surface 406, 408 of the carrier 404 may have a mask 422 thereon (e.g., an ink mask or dark mask, and in some cases a plurality of masks). The mask 422 may define an opening 418 (e.g., a first opening or central opening) that allows light of at least one wavelength to pass through the carrier 404, and the lens 436 may be aligned with the opening 418. In some cases, the lens 436 may be or include a Fresnel lens, a spherical lens, a diffuser film, or the like.

In some cases, the light filter 438 may include one or more segments 450, and each segment 450 may be attached to (e.g., laminated to) the interior surface 406 of the carrier 404 and positioned on the interior surface (e.g., adjacent or around the lens 436) to prevent a set of one or more light receivers of the optical sensor subsystem 416 from receiving a portion of the light that is emitted by a set of one or more light emitters of the optical sensor subsystem 416. The set of light emitters and set of light receivers are not shown in FIG. 4C, and may be attached to an underside of the optical sensor subsystem 416. When the carrier 404 includes the mask 422, the mask 422 may further define a second opening 420a, or a set of openings 420 including the second opening 420a. The second opening 420a or set of openings 420 may be positioned adjacent or around the first opening 418. In these embodiments, the segments 450 of the light filter 438 (or a light filter ring or other light filter configuration) may be aligned with (e.g., may cover) each of the openings in the set of openings 420.

As an example, FIG. 4C shows a mask 422 that defines a set of eight radial openings 420 around a central opening 418. Each segment 450 of the light filter 438 may block (e.g., absorb) a portion of light emitted by a set of light emitters that is attached to the optical sensor subsystem 416, which portion of light reflects from a surface too close to (or within) the carrier 404 (e.g., the exterior surface 408 of the carrier 404, imperfections within the carrier 404, or a medium too close to the carrier 404), such that the reflected light is not useful in a sensing operation for which the optical sensor subsystem 416 is designed. For example, when the optical sensor subsystem 416 is configured to determine a biological parameter of a user, light reflected from the carrier 404, or from the outer layer of skin of the user, may not have any relation to the biological parameter determined and may not be useful. Accordingly, the filter may be configured to filter out light frequencies associated with light reflected from the carrier and/or a skin surface, allowing light reflected from deeper skin layers, blood vessels, and the like to be received by the receiver(s). In some examples, the light filter 438 or segments 450 thereof may include at least one of a light control film, a light polarizer, an anti-reflective film, a reflective film, or a light absorber. Accordingly and as one non-limiting example, the optical sensor subsystem 416 may act as an optical heart rate detector.

In some embodiments, the mask 422 may represent multiple masks, and different masks may allow different wavelengths of light to pass through the carrier 404, as described for example with reference to FIGS. 5A-5E & 6.

The optical sensor subsystem 416 may include a substrate 452 on which the set of one or more light emitters (e.g., LEDs) and the set of one or more light receivers (e.g., photodetectors, such as photodiodes) are attached. The light emitter(s) and light receiver(s) may be attached or positioned on the substrate 452 to emit and receive light through the carrier 404. The sensor subsystem 416 may be attached to the carrier 404 by one or more adhesives 440/442, such as pressure sensitive adhesives (PSAs) or heat-activated films (HAFs). In some cases, the set of light emitters may be centrally attached on the substrate 452, and a first wall may be attached to (e.g., formed on or bonded to) an underside of the substrate 452 surrounding the set of light emitters. The first wall may be attached to the interior surface 406 of the carrier 404 using a first adhesive 440. The set of light receivers may be attached on the substrate 452 around the set of light emitters, between the first wall and a second wall attached to (e.g., formed on or bonded to) the underside of the substrate 452. The second wall may be attached to the interior surface 406 of the carrier 404 using a second ring of adhesive 442.

The substrate 452 of the optical sensor subsystem 416 may include various contacts, pads, traces, or other conductive structures 454 that enable the processing subsystem 444 to be electrically coupled to the set of light emitters and set of light receivers of the optical sensor subsystem 416. The processing subsystem 444 may include a substrate 456 (e.g., a printed circuit board (PCB)) that is attached to the optical sensor subsystem 416, and thereby to the carrier 404, via the conductive structures 454 and/or additional adhesive between the substrates 452, 456 of the optical sensor subsystem 416 and the processing subsystem 444. The substrates 452, 456 may also or alternatively be connected using mechanical fasteners (e.g., screws). The processing subsystem 444 may activate the light emitters and light receivers to perform a sensor function (e.g., to determine a heart rate). In some cases, the processing subsystem 444 may be attached to another structure within the watch body, and may be electrically connected to the conductive structures 454 of the optical sensor subsystem 416 by a flex circuit or other conductors.

In some embodiments, the substrate 456 of the processing subsystem 444 may have a hole 458 therein, and the magnet 446 may be aligned with the hole 458 and abutted to (or attached to) the substrate 452. In some cases, the magnet 446 may be adhesively bonded to the substrate 452 of the optical sensor subsystem 416. The magnet 446 may inductively couple to a battery charger used for charging a battery included within the watch body, which battery may power components of the watch including the components of the optical sensor subsystem 416 and the processing subsystem 444.

The magnetic shield 448 may abut (or be attached to) the magnet 446. In some cases, the magnetic shield 448 may be adhesively bonded to the magnet 446. The magnetic shield 448 may direct magnetic flux associated with the magnet 446 toward and out the carrier 404 to improve inductive battery charging performance for a battery included within the watch body 202.

Direct or indirect connection of the components shown in FIG. 4C to the interior surface 406 of the carrier 404 can reduce the height of the components when stacked.

Figure 4D:
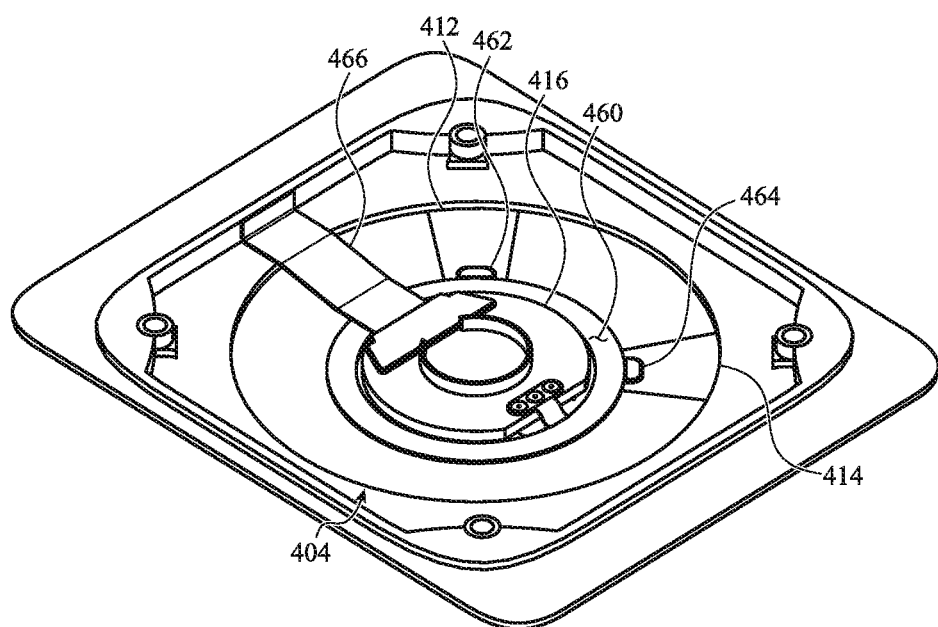

FIG. 4D shows the sensor subsystem 416 attached to the carrier 404 shown in FIGS. 4A-4C. FIG. 4B also shows a flex circuit 460, surrounding the sensor subsystem 416, which may provide electrical connections between the electrodes 412, 414 and the sensor subsystem 416 while also providing a ground that operates as an electrical noise mitigation barrier (or E-shield) between the sensor subsystem 416 and the electrodes 412, 414. The electrodes 412, 414 may be connected to the electrical contacts 462, 464, which electrical contacts 462, 464 are on the interior surface of the carrier 404 and connected to both traces in the flex circuit 460 and the electrodes 412, 414. Traces in the flex circuit 460 may be connected to the electrical contacts 462, 464 via a conductive epoxy, and may connect the electrical contacts 462, 464 to the sensor subsystem 416. A processor may be part of the sensor subsystem 416, and the processor may be connected to another processor or other circuitry via a flex circuit 466.

Figure 5A:
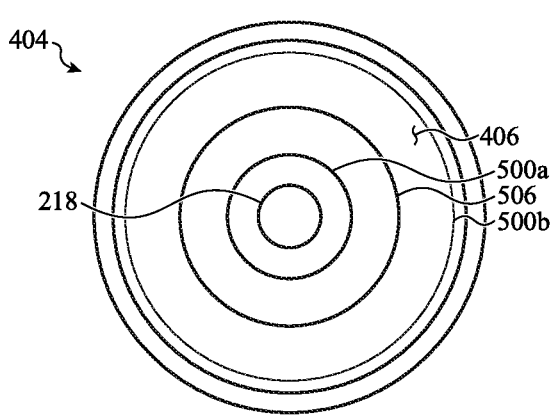
FIGS. 5A-5E illustrate an example of coatings that may be deposited on the interior and exterior surfaces of the carrier shown in FIGS. 4A-4C.

FIGS. 5A-5E illustrate an example of coatings that may be deposited on the interior and exterior surfaces of the carrier 404 shown in FIGS. 4A-4C. As shown in FIG. 5A, a first mask 500 (e.g., a first ink mask) that is opaque to infrared (IR) and visible light may be deposited (e.g., PVD deposited) on the interior surface 406 of the carrier 404. In some examples, the first mask 500 may include an inner ring 500a and an outer ring 500b that define a central first opening 418 and a concentric second opening 506 (i.e., a second opening 506 that is concentric with the first opening 418). The central first opening 418 may be positioned over light emitters of the optical sensor subsystem 416 described with reference to FIG. 4C (and over the optional lens 436), and the concentric second opening 506 may be positioned above light receivers of the sensor subsystem 416. The inner ring 500a of the first mask may prevent the light receivers from receiving light that is unlikely to have passed through a user's skin after passing through the central first opening 418. The outer ring 500b of the first mask 500 may in some cases be provided for cosmetic reasons, and in some cases may not be provided.

Figure 5B:
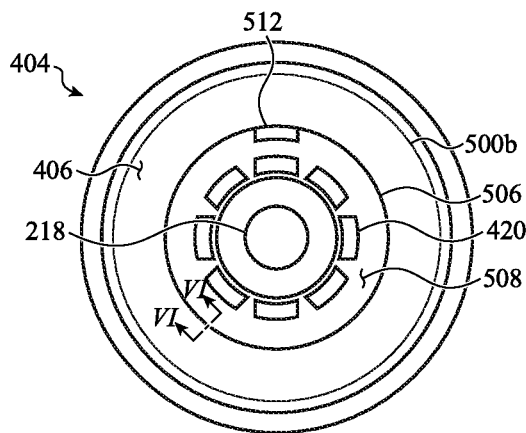
Figure 6:
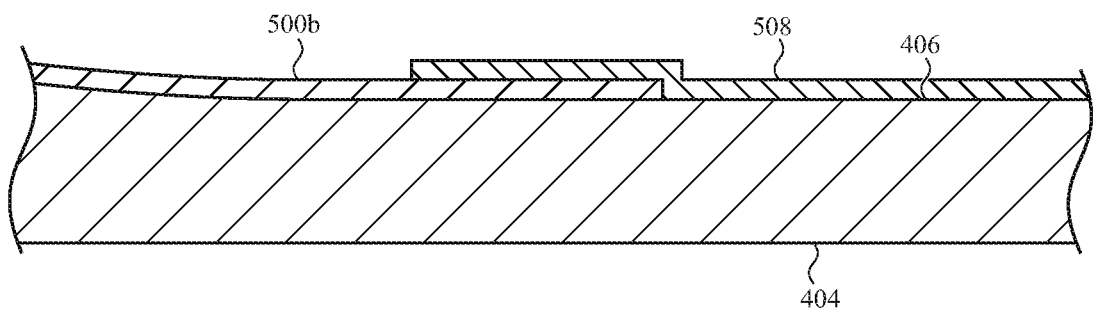
FIG. 6 shows a cross-section of the carrier shown in FIG. 5B.

FIG. 5B shows a second mask 508 (e.g., a second ink mask) that is opaque to visible light but transparent to IR light. The second mask 508 may be deposited (e.g., PVD deposited) on the interior surface 406 of the carrier 404. The second mask 508 may be deposited on the carrier 404 over the concentric second opening 506 in the first mask 500, and may overlap the inner and outer rings 500a, 500b of the first mask, as shown in FIG. 6. The second mask 508 may define a plurality of visible light openings 420 above respective light receivers of the optical sensor subsystem 416, while allowing IR light to pass through the entirety of the concentric second opening 506. This may increase the amount of IR light received by the light receivers. The second mask 508 may also define an optional opening above a condensation detector 512. In some cases, the second mask 508 may look visually similar to the first mask 500 (e.g., both masks may be dark masks, such that it may be impossible or difficult for a user to visually distinguish the first and second masks 500, 508).

Figure 5C:
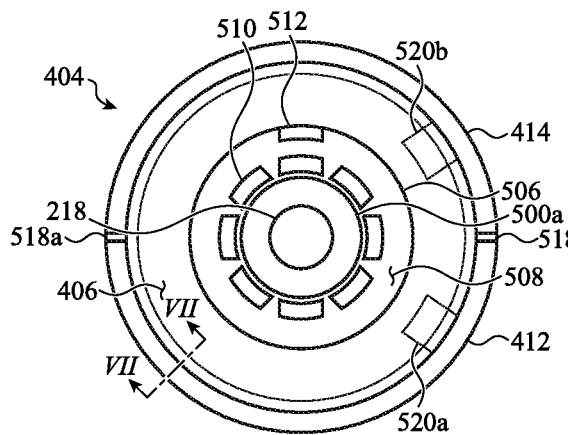
Figure 5D:
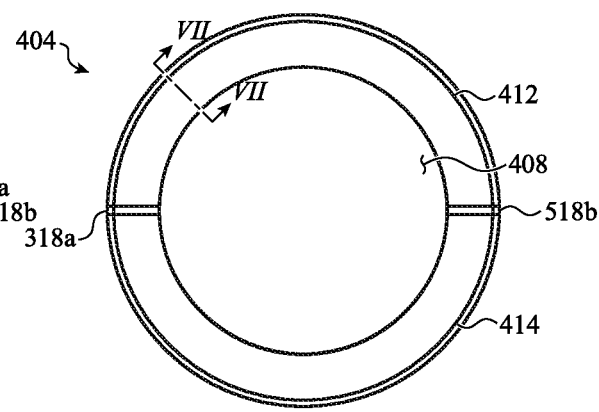

FIGS. 5C and 5D show an example of PVD deposited first and second electrodes 514a, 514b on the interior and exterior surfaces 406, 408 of the carrier 404. The first and second electrodes 412, 414 may be arc-shaped and positioned at the periphery of the carrier 404. The first and second electrodes 412, 414 may be sized based on factors such as: providing a sufficient area to provide good electrical contact between the electrodes 412, 414 and skin (which may improve electrical sensor efficiency); providing electrodes 412, 414 of a size that do not substantially interfere with an antenna or other electrical structures of a device (which may improve wireless communication efficiency); or providing electrodes 412, 414 positioned to allow optical communication through the carrier 404 (which may improve optical communication efficiency). The first and second electrodes 412, 414 may be separated from one another by a pair of gaps 518a, 518b.

The first and second electrodes 412, 414 may be deposited on both the interior and exterior surfaces 406, 408 of the carrier 404 and may wrap around the edge (or perimeter) of the carrier 404. The material used to form the first and second electrodes 412, 414 may be patterned to form electrical contacts 520a, 520b (e.g., tabs) on the interior surface 406 of the carrier 404. The first and second electrodes 412, 414 may overlap the first mask 500 (or outer ring 500b of the first mask) on the interior surface 406 of the carrier 404, such that the first mask 500 is positioned between the first and second electrodes 412, 414 and the interior surface 406 of the carrier 404. Thus, the material used to form the electrodes 412, 414 may need to have properties that enable the material to adhere to a carrier surface (e.g., a sapphire surface) and a mask (e.g., an ink mask). The material or materials used to form the electrodes 412, 414 may also have properties, singularly or in combination, such as: a low impedance and good conductivity (e.g., a low DC resistance); a low electrode-to-skin impedance; a high hardness to reduce scratching of the electrodes 412, 414; a higher elastic modulus than the carrier 404 (e.g., to mitigate the likelihood that a crack in an electrode 412, 414 propagates through the carrier 404); compatibility with a HAF or other adhesive; and good biocompatibility (e.g., not likely to cause an adverse reaction to a user of a device). In some embodiments, the electrodes 412, 414 may include aluminum titanium nitride (AlTiN) or chromium silicon carbonitride (CrSiCN). AlTiN and CrSiCN hold up well to abrasion and corrosion and tend not to place undue stresses on a sapphire carrier.

Figure 5E:
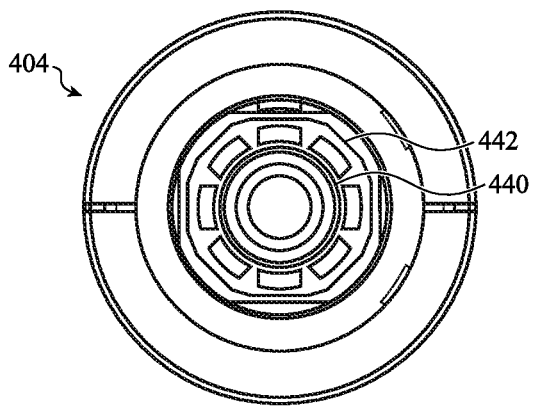

FIG. 5E shows an example deposition of adhesive on the interior surface 406 of the carrier 404. The adhesive may be deposited in inner and outer rings 440, 442, as described with reference to FIG. 4C. The inner ring 440 of adhesive may be positioned on the inner ring 500a of the first mask. The outer ring 442 of adhesive may be positioned on the second mask 508, outward from the plurality of openings 420 in the second mask 508. In some cases, the adhesive may include a PSA or HAF.

FIG. 6 shows a cross-section of the carrier 404 shown in FIG. 5B, and illustrates an overlap between the first and second masks 500, 508. The second mask 508 may overlap the first mask (e.g., outer ring 500b) on the interior surface 406 of the carrier 404 such that the first mask 500 is positioned between the second mask 508 and the interior surface 406 of the carrier 404.

Figure 7:
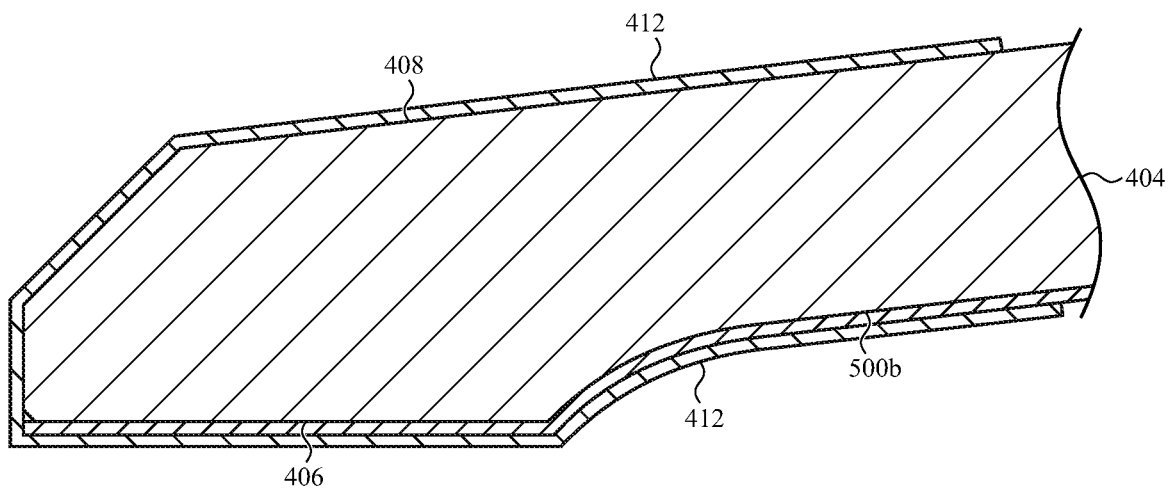
FIG. 7 shows a cross-section of the carrier shown in FIGS. 5C and 5D.

FIG. 7 shows a cross-section of the carrier 404 shown in FIG. 5C or 5D, and illustrates an overlap between the first electrode 412 (or second electrode) and the first mask 500 (e.g., outer ring 500b of the first mask). The first electrode 412 may overlap the first mask 500 (or outer ring 500b of the first mask) on the interior surface 406 of the carrier 404, such that the first mask 500 is positioned between the first electrode 412 and the interior surface 406 of the carrier 404.

Figure 8:
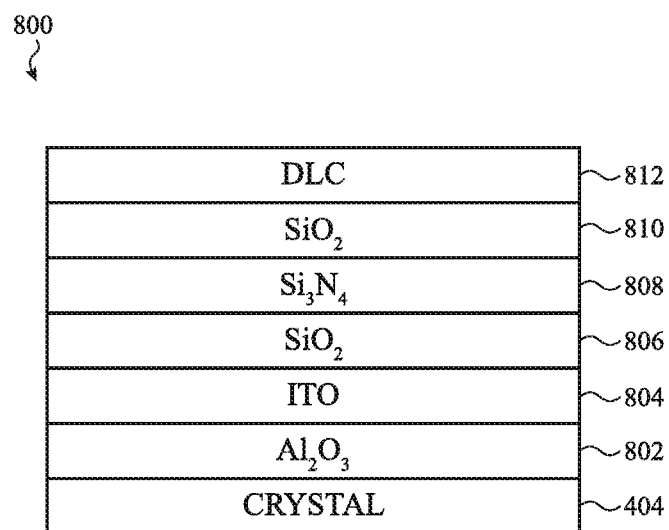
FIG. 8 shows an example layer construction of an ITO-based electrode.

In some embodiments, the electrodes 412, 414 shown in FIGS. 5C, 5D, and 7 may be formed using indium titanium oxide (ITO) or another transparent material. In these embodiments, the electrodes 412, 414 may be transparent to light emitted by a sensor subsystem positioned below the carrier 404, and thus the electrodes 412, 414 may extend over a greater portion (or all) of the exterior surface 408 of the carrier 404. FIG. 8 shows an example layer construction of an ITO-based electrode. As shown, the stack 800 may include a layer 802 of aluminum oxide ($Al_2O_3$) on the carrier, a layer 804 of ITO on the layer 802 of aluminum oxide, a first layer 806 of silicon dioxide ($SiO_2$) on the layer 804 of aluminum oxide, a layer 808 of silicon nitride ($Si_3N_4$) on the first layer 806 of silicon dioxide, a second layer 810 of silicon dioxide on the layer 808 of silicon nitride, and a layer 812 of diamond like carbon, or another hard coating, on the second layer 810 of silicon dioxide. Alternatively, the layer 808 of silicon nitride and second layer 810 of silicon dioxide may not be deposited, or only the layer 804 of ITO may be deposited, or just the layer 804 of ITO layer and first layer 806 of silicon dioxide may be deposited. Other variations in the number or types of layers may also be used to form the stack 800. Each of the layers may be transparent to IR or visible light.

Figure 9A:
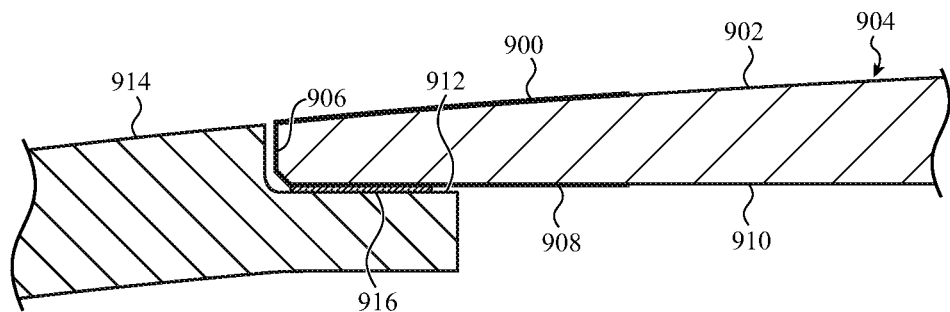
FIGS. 9A-9C show alternative electrical connections between an electrode on an exterior surface of a carrier that forms part of a housing of an electronic device and an electrical contact interior to the electronic device.
Figure 9B:
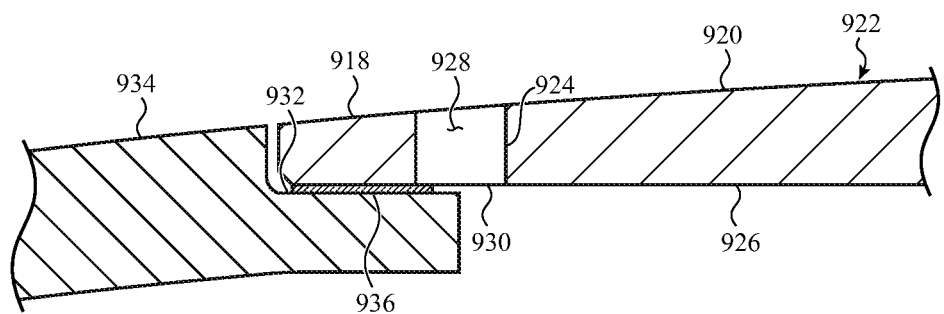
Figure 9C:
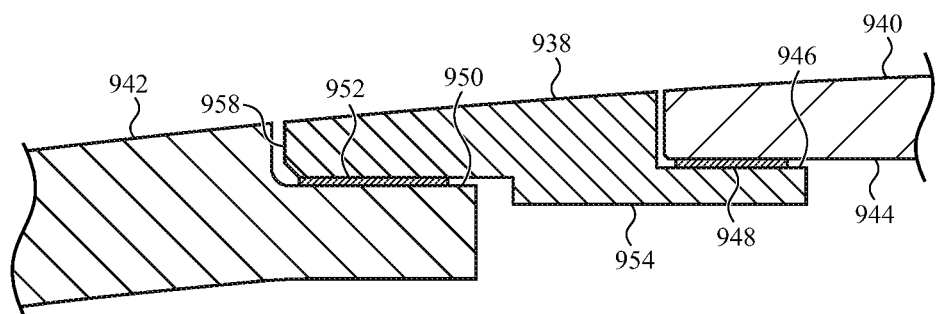

FIGS. 9A-9C show alternative electrical connections between an electrode (e.g., an electrode on an exterior surface of a carrier that forms part of a housing of an electronic device) and an electrical contact interior to the electronic device. In some examples, the carriers shown in cross-section in FIGS. 9A-9C may have circular perimeters. In other examples, the carriers may have perimeters that are oval-shaped, square-shaped, rectangular-shaped, and so on. The techniques described with reference to FIGS. 9A-9C can be applied to carriers having various perimeter shapes, to carriers having different compositions, and so on. In some embodiments, the features shown in FIGS. 9-9C may be replicated to electrically connect more than one electrode on an exterior surface of an electronic device to components interior to the electronic device.

In FIG. 9A, the electrode 900 may be a thin film electrode that is PVD deposited on a surface 902 of a carrier 904. The surface 902 on which the electrode 900 is deposited may be a surface of the carrier 904 that is exterior to an electronic device (i.e., the electrode 900 may be deposited on an exterior surface 902 of the carrier 904). As shown, a conductive material used to form the electrode 900 may be deposited on the carrier 904 such that the material wraps around an edge 906 or perimeter of the carrier 904 to form an electrical contact 908 on a surface 910 of the carrier 904 that is interior to the electronic device (i.e., on an interior surface 910 of the carrier 904). In some cases, the electrical contact 908 may be a tab that traces a much smaller arc about the periphery of the carrier 904 than the electrode 900 (as shown, for example, in FIGS. 5C, 5D, and 5E). In other cases, the electrical contact 908 may be arc-shaped and trace an arc that is similar in size to an arc traced by the electrode 900 on the exterior surface 902 of the carrier 904.

In some cases, the conductive material(s) used to form the electrode 900 and electrical contact 908 may be deposited on the exterior surface 902, edge 906, and interior surface 910 of the carrier 904 in a single operation (or single set of operations in which the material(s) are deposited on the exterior surface 902, edge 906, and interior surface 910 of the carrier 904). In other cases, the material(s) used to form the electrode 900 may be deposited on the edge 906 or interior surface 910 of the carrier 904 in operations that are performed separately from one or more operations in which the electrode 900 is deposited on the exterior surface 902 of the carrier 904. In these latter examples, the material(s) may be deposited such that the materials overlap. In some cases, a set of one or more materials used to form the electrode 900 may differ from a set of one or more materials deposited on the edge 906 or interior surface 910 of the carrier 904.

In some embodiments, the conductive material(s) deposited on the exterior surface 902, edge 906, and interior surface 910 of the carrier 904 may include a layer of SUS or a layer of DLC. In other embodiments, only the electrode 900 or edge 906 of the carrier 904 may be coated with a layer of stainless steel or DLC. In some examples, the conductive material(s) may include a PVD deposited layer of AlTiN or CrSiCN.

In some embodiments, one or more masks (e.g., one or more ink masks) may be applied to the interior surface of the carrier (e.g., as described with reference to FIGS. 5A-5E, 6, & 7). In these embodiments, one or more of the conductive materials used to form the electrode 900 and electrical contact 908 may be applied over the mask(s). The conductive material(s), and the manner in which the conductive material(s) are deposited on the carrier 904, may therefore be selected to ensure adhesion of the conductive material(s) to the carrier 904 and to the ink or other material used to form the mask(s).

As shown in FIG. 9A, a peripheral band of the interior surface 910 of the carrier 904 may be attached to a recessed ledge 912 in another housing member 914 of the electronic device (e.g., with the carrier 904 overlapping the housing member 914). In such an embodiment, the carrier 904 may be attached to the housing member 914 using an adhesive 916, such as a heat-activated film (HAF). The adhesive 916 or conductive material(s), and the manner in which the carrier 904 is attached to the housing member 914, may therefore be selected to ensure adhesion of the carrier 904 to the housing member 914.

The electrical contact 908 may have a great enough width (e.g., a great enough width along a radius of the carrier 904) that the electrical contact 908 extends past the recessed ledge 912 in the housing member 914 when the carrier 904 is attached to the housing member 914, making the electrical contact 908 accessible interior to the electronic device. In some cases, a flex circuit, other flexible conductor, or other conductive element may be soldered or otherwise electrically connected to the electrical contact 908, to enable a signal to be received from or applied to the electrode 900.

In FIG. 9B, the electrode 918 may be a thin film electrode that is PVD deposited on a surface 920 of a carrier 922. The surface 920 on which the electrode 918 is deposited may be a surface of the carrier 922 that is exterior to an electronic device (i.e., the electrode 918 may be deposited on an exterior surface 920 of the carrier 922). Prior to or after depositing the electrode 918 on the carrier 922, a thru-carrier via 924 may be drilled or otherwise cut into the carrier 922. The thru-carrier via 924 may extend from the exterior surface 920 of the carrier 922 (or electrode 918) to the interior surface 926 of the carrier 922. The via 924 may be coated or filled with a conductive material 928 such as stainless steel (SUS), and the conductive material 928 may be covered by, overlap, or otherwise electrically connect to the electrode 918. In some cases, the conductive material 928 in the via 924 may be molded or glued in the via 924. The conductive material 928 may provide an electrical contact 930 on a surface 926 of the carrier 922 that is interior to an electronic device (i.e., on an interior surface of the carrier). In some cases, the conductive material 928 in the via 924 may overlap a portion of the interior surface 926 of the carrier 922, or may be connected to another conductive element deposited on the interior surface 926 of the carrier 922.

The conductive material(s) used to form the electrode 918 and deposited in the via 924 may be the same or different. In some embodiments, the conductive material(s) used to form the electrode 918 may include a layer of stainless steel (SUS) or a layer of diamond like carbon (DLC). In some examples, the conductive material(s) may include a PVD deposited layer of Aluminum Titanium Nitride (AlTiN) or Chromium Silicon Carbon Nitride (CrSiCN).

As shown in FIG. 9B, a peripheral band of the interior surface 926 of the carrier 922 may be attached to a recessed ledge 932 in another housing member 934 of the electronic device (e.g., with the carrier 922 overlapping the housing member 934). In such an embodiment, the carrier 922 may be attached to the housing member 934 using an adhesive 936, such as a HAF. The adhesive 936, and the manner in which the carrier 922 is attached to the housing member 934, may therefore be selected to ensure adhesion of the carrier 922 to the housing member 934.

When the carrier 922 is attached to the housing member 934, the via 924 may be positioned such that it overlaps the recessed ledge 932 or is interior to the recessed ledge 932, making the electrical contact 930 accessible interior to the electronic device. In some cases, a flex circuit, other flexible conductor, or other conductive element may be soldered or otherwise electrically connected to the electrical contact 930, to enable a signal to be received from or applied to the electrode 918.

In FIG. 9C, the electrode 938 may be a metallic arc-shaped element positioned between a carrier 940 and another housing member 942 of an electronic device. In some embodiments, the electrode 938 may be a singular metallic ring-shaped electrode (e.g., one electrode). In these embodiments, a peripheral band of a surface of the carrier 940 that is interior to the electronic device (e.g., an interior surface 944 of the carrier 940) may be attached to a recessed ledge 946 in the electrode 938 (e.g., with the carrier 940 overlapping the electrode 938), and the electrode 938 may be attached to a recessed ledge 950 in the housing member 942 (e.g., with the electrode 938 overlapping the housing member 942). In other embodiments, the electrode 938 may be arc-shaped and may be one of two or more arc-shaped electrodes between the carrier 940 and the housing member 942. In these embodiments, a peripheral band of the interior surface of the carrier 940 may be attached to recessed ledges 946 in multiple arc-shaped electrodes 938 (e.g., with the carrier 940 overlapping the electrodes 938), and each of the arc-shaped electrodes 938 may be attached to the recessed ledge 950 in the housing member 942 (e.g., with the electrodes 938 overlapping the housing member 942). In some cases, the multiple arc-shaped electrodes 938 may be electrically isolated from each other by flexible seals or gaskets, or by rigid separators (e.g., rigid extensions of the housing member 942, which rigid extensions may include extensions of the recessed ledge 950 to which the electrodes 938 are attached. In some cases, the electrode 938 may be attached to the housing member 942 before the carrier 940 is attached to the electrode 938.

The electrode 938 may be formed of a conductive material including a layer of stainless steel (SUS) or DLC. In some examples, the conductive material may include a PVD deposited layer of Aluminum Titanium Nitride (AlTiN) or Chromium Silicon Carbon Nitride (CrSiCN). A surface 954 of the electrode 938 interior to the electronic device may provide an electrical contact for connecting components interior to the electronic device to the electrode 938.

In some cases, an edge 956 or perimeter of the carrier 940 may be abutted directly to the electrode 938, and an edge 958 of the electrode 938 may be abutted directly to the housing member 942. In other cases, an adhesive, seal, gasket, or filler may fill a gap between the carrier 940 and the electrode 938 or a gap between the electrode 938 and the housing member 942.

As shown in FIG. 9C, a peripheral band of the interior surface 944 of the carrier 940 may be attached to a recessed ledge 946 in the electrode 938, and a peripheral band of an interior surface 954 of the electrode 938 may be attached to the housing member 942. In such an embodiment, the carrier 940 may be attached to the electrode 938 or the electrode 938 may be attached to the housing member 942 using an adhesive 948 or 952, such as a HAF. The adhesive 948 or 952, and manner in which the respective elements are attached, may therefore be selected to ensure adhesion of the carrier 940 to the electrode 938 (or adhesion of the electrode 938 to the housing member 942).

When the electrode 938 is attached to the housing member 942, the electrode 938 may be positioned such that it overlaps the recessed ledge 950 or is interior to the recessed ledge 950, making the electrode 938 accessible interior to the electronic device. In some cases, a flex circuit, other flexible conductor, or other conductive element may be soldered or otherwise electrically connected to the electrode 938, to enable a signal to be received from or applied to the electrode 938.

FIGS. 10A-10D show alternative carrier profiles, and alternative attachments (e.g., structural attachments) of carriers to other housing members of an electronic device. In some examples, the carriers may have circular perimeters. In other examples, the carriers may have perimeters that are oval-shaped, square-shaped, rectangular-shaped, and so on. The techniques described with reference to FIGS. 10A-10D can be applied to carriers having various perimeter shapes, to carriers having different compositions, and so on. Each of FIGS. 10A-10D shows an exterior surface (e.g., a back surface) of an electronic device, such as an electronic watch, and a cross-section of the exterior surface of the electronic device.

Figure 10A:
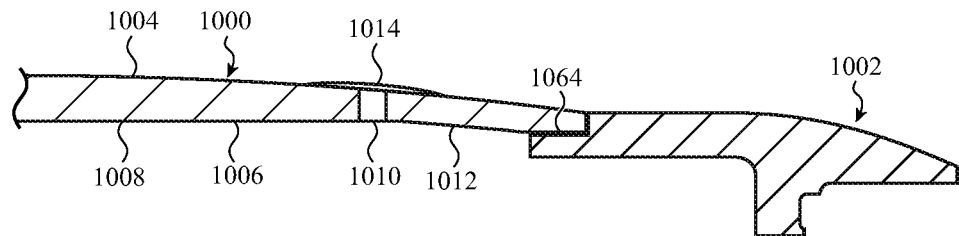
FIGS. 10A-10D show alternative carrier configurations, and alternative attachments or connections of carriers to other housing members of an electronic device.

In FIG. 10A, a carrier 1000 is attached to another housing member 1002 of an electronic device. The carrier 1000 includes an exterior surface 1004 that forms a part of the exterior surface of the electronic device, and an interior surface 1006 that faces components interior to the electronic device.

A peripheral band of the interior surface 1006 of the carrier 1000 may be attached to a recessed ledge 1064 in the housing member 1002 (e.g., with the carrier 1000 overlapping the housing member 1002). In such an embodiment, the carrier 1000 may be attached to the housing member 1002 using an adhesive, such as a HAF. The adhesive, and the manner in which the carrier 1000 is attached to the housing member 1002, may be selected to ensure adhesion of the carrier 1000 to the housing member 1002.

The carrier 1000 may be variously configured, but in FIG. 10A, an inner portion 1008 of the interior surface 1006 of the carrier 1000, such as a portion of the carrier interior to a number of thru-carrier vias 1010, is flat. An outer portion 1012 of the interior surface 1006, such as a portion outside the number of thru-carrier vias 1010, is concave or inwardly-sloped (downwardly-sloped in the figure) with respect to the inner portion 1008 of the interior surface 1006. In contrast, the exterior surface 1004 of the carrier 1000 may be convex. Thus, the thickness of the carrier 1000 may vary to some degree from its center axis to its perimeter.

In some embodiments, one or more arc-shaped electrodes 1014 (e.g., two electrodes) may be positioned around the exterior surface 1004 of the carrier 1000, inward from the perimeter of the carrier 1000. In other embodiments, the electrodes 1014 may have other shapes or may extend to or around the perimeter. The electrodes 1014 may be PVD deposited thin film electrodes. In some cases, the electrodes 1014 may be connected to interior components of the electronic device by the thru-carrier vias 1010, which in some cases may be drilled or formed through the flat inner portion 1008 of the interior surface 1006 of the carrier 1000. In other cases, the electrodes 1014 may be connected to interior components of the electronic device by conductive material that wraps around the edge or perimeter of the carrier 1000, or in any of the ways shown in FIGS. 9A-9C.

In some cases, components such as a sensor subsystem may be attached to the inner, flat portion of the interior surface 1006 of the carrier 1000.

Figure 10B:
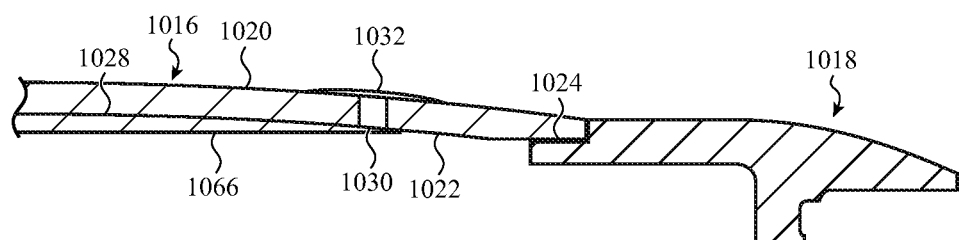

In FIG. 10B, a carrier 1016 is attached to another housing member 1018 of an electronic device. The carrier 1016 includes an exterior surface 1020 that forms a part of the exterior surface of the electronic device, and an interior surface 1022 that faces components interior to the electronic device.

A peripheral band of the interior surface 1022 of the carrier 1016 may be attached to a recessed ledge 1024 in the housing member 1018 (e.g., with the carrier 1016 overlapping the housing member 1018). In such an embodiment, the carrier 1016 may be attached to the housing member 1018 using an adhesive, such as a HAF. The adhesive, and the manner in which the carrier 1016 is attached to the housing member 1018, may be selected to ensure adhesion of the carrier 1016 to the housing member 1018.

The carrier 1016 may be variously configured, but in FIG. 10B, the carrier 1016 has a uniform thickness. The interior surface 1022 of the carrier 1016 may be concave, and the exterior surface 1020 of the carrier 1016 may be convex. To provide a flat surface for connecting components (e.g., a sensor subsystem) to the carrier 1016, a secondary carrier 1026 having a convex exterior surface 1028 and a flat interior surface 1066 may be attached to an inner portion of the interior surface 1022 of the carrier 1016. The secondary (or interior) carrier 1026 may be attached to the primary (or exterior) carrier 1016 using a transparent adhesive. In some cases, the secondary carrier 1026 may be attached to the primary carrier 1016 interior to a number of thru-carrier vias 1030.

In some embodiments, one or more arc-shaped electrodes 1032 (e.g., two electrodes) may be positioned around the exterior surface of the carrier 1016, inward from the perimeter of the carrier 1016. In other embodiments, the electrodes 1032 may have other shapes or may extend to or around the perimeter. The electrodes 1032 may be PVD deposited thin film electrodes. In some cases, the electrodes 1032 may be connected to interior components of the electronic device by the thru-carrier vias 1030. In other cases, the electrodes 1032 may be connected to interior components of the electronic device by conductive material that wraps around the edge or perimeter of the carrier 1016, or in any of the ways shown in FIGS. 9A-9C.

Figure 10C:
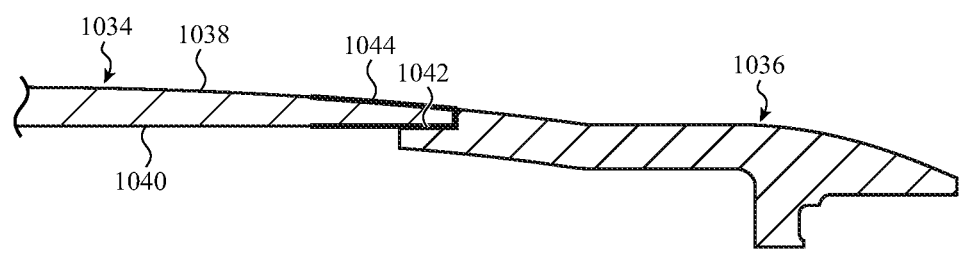
Figure 10D:
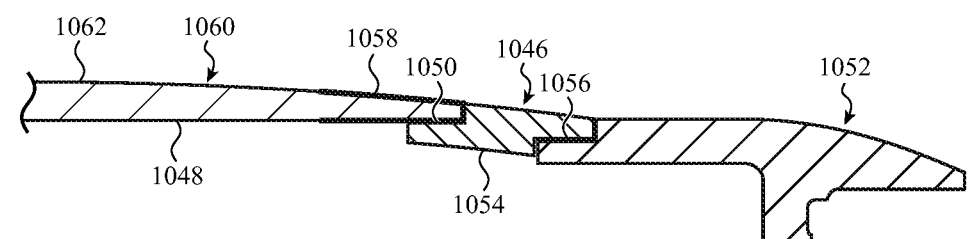

FIGS. 10C & 10D each show a carrier attached to another housing member of an electronic device. The carrier includes an exterior surface that forms a part of the exterior surface of the electronic device, and an interior surface that faces components interior to the electronic device. In each of FIGS. 10C & 10D, the carrier has a flat interior surface and a convex exterior surface. The carriers shown in FIGS. 10C & 10D may be easier to manufacture than the carriers shown in FIGS. 10A & 10B.

In FIG. 10C, a carrier 1034 is attached to another housing member 1036 of an electronic device. The carrier 1034 includes an exterior surface 1038 that forms a part of the exterior surface of the electronic device, and an interior surface 1040 that faces components interior to the electronic device.

A peripheral band of the interior surface 1040 of the carrier 1034 may be attached to a recessed ledge 1042 in the housing member (e.g., with the carrier 1034 overlapping the housing member 1036). In such an embodiment, the carrier 1034 may be attached to the housing member 1036 using an adhesive, such as a HAF. The adhesive, and the manner in which the carrier 1034 is attached to the housing member 1036, may be selected to ensure adhesion of the carrier 1034 to the housing member 1036.

In some embodiments, one or more arc-shaped electrodes 1044 (e.g., two electrodes) may be positioned around the perimeter of the exterior surface 1038 of the carrier 1034. In other embodiments, the electrodes 1044 may have other shapes or other positions on the exterior surface 1038 of the carrier 1034. The electrodes 1044 may be PVD deposited thin film electrodes. In some cases, the electrodes 1044 may be connected to interior components of the electronic device by conductive material that wraps around the edge or perimeter of the carrier 1034, or in any of the ways shown in FIGS. 9A-9C.

In some cases, components such as a sensor subsystem may be attached to the interior surface 1040 of the carrier 1034.

In FIG. 10D, a carrier 1060 is attached to another housing member 1046 of an electronic device (e.g., an electronic watch), similarly to how the carrier 1034 is attached to another housing member 1036 in FIG. 10C. For example, a peripheral band of the interior surface 1048 of the carrier 1060 may be attached to a recessed ledge 1050 in the housing member 1046 (e.g., with the carrier 1060 overlapping the housing member 1046). The carrier 1060 may be attached to the housing member 1046 using an adhesive, such as a HAF. The adhesive, and the manner in which the carrier 1060 is attached to the housing member 1046, may be selected to ensure adhesion of the carrier 1060 to the housing member 1046.

The housing member 1046 to which the carrier 1060 is attached may be attached to yet another housing member (e.g., a second housing member 1052). A peripheral band of the interior surface 1054 of the first housing member 1046 may be attached to a recessed ledge 1056 in the second housing member 1052 (e.g., with the first housing member 1046 overlapping the second housing member 1052). The first housing member 1046 may be attached to the second housing member 1052 using an adhesive, such as a HAF. The adhesive, and the manner in which the first housing member 1046 is attached to the second housing member 1052, may be selected to ensure adhesion of the first housing member 1046 to the second housing member 1052. In some cases, the first housing member 1046 may electrically insulate the electrodes 1058 on the carrier 1060 from the second housing member 1052, or may provide a transition between incompatible materials, or may provide a support for the carrier 1060, or may facilitate assembly of the housing of the electronic device.

In some embodiments, one or more arc-shaped electrodes 1058 (e.g., two electrodes) may be positioned around the perimeter of the exterior surface of the carrier 1060. In other embodiments, the electrodes 1058 may have other shapes or other positions on the exterior surface 1062 of the carrier 1060. The electrodes 1058 may be PVD deposited thin film electrodes. In some cases, the electrodes 1058 may be connected to interior components of the electronic device by conductive material that wraps around the edge or perimeter of the carrier, or in any of the ways shown in FIGS. 9A-9C.

In some cases, components such as a sensor subsystem may be attached to the interior surface 1048 of the carrier 1060.

Figure 11A:
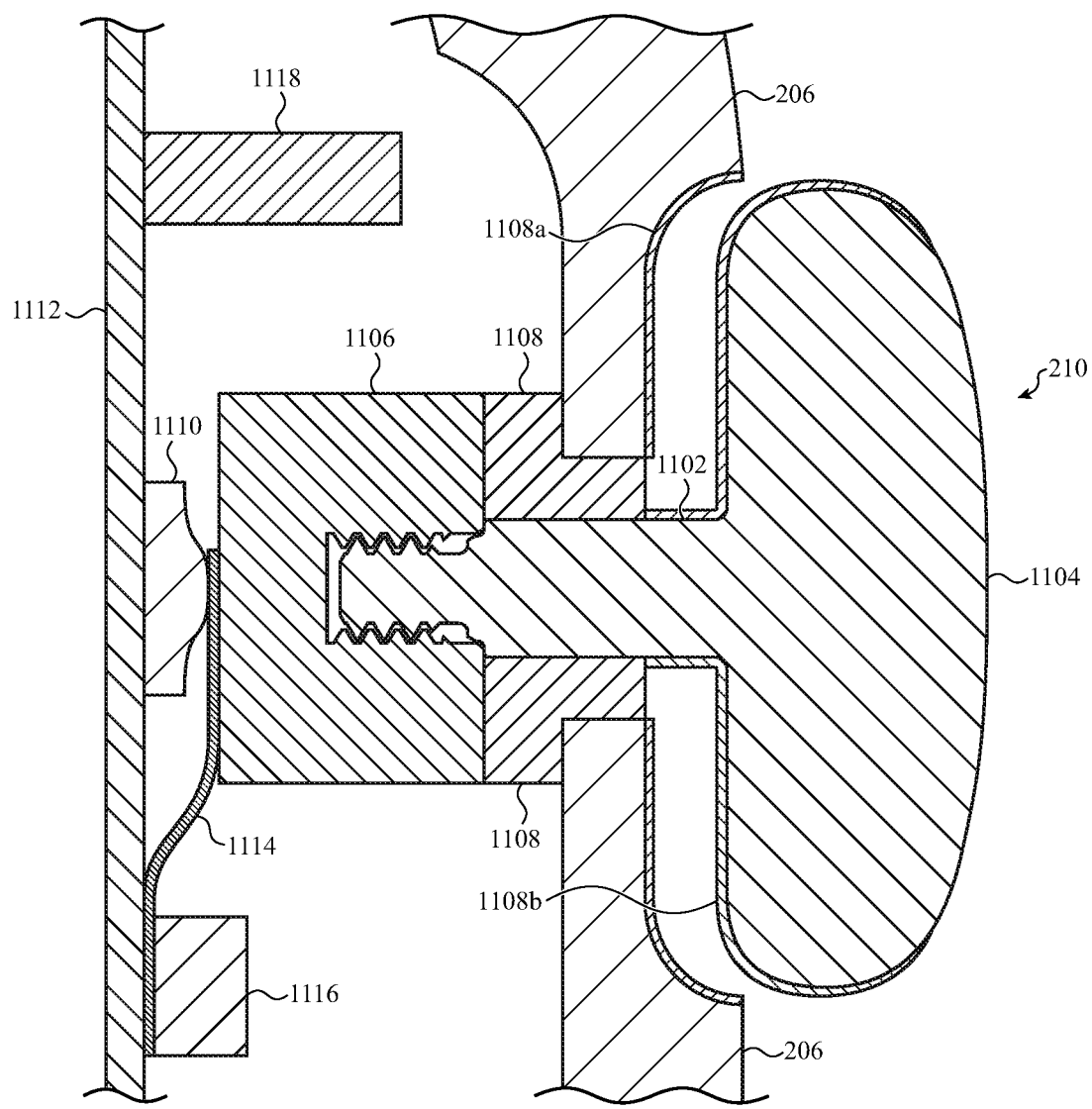
FIG. 11A is a cross-section of an example crown assembly.

Turning now to the implementation of an electrode on a crown, FIG. 11A shows an example elevation of a crown assembly 1100. The crown assembly 1100 may be an example of a crown assembly included in any of the electronic devices described with reference to FIG. 1A, 1B, 2A-2C, 3, 4A, or 4B. The crown assembly 1100 may include a crown 210.

The crown 210 may be mechanically and electrically connected to a shaft 1102 that extends through an opening in a housing. By way of example, the housing is shown to be the housing 206 of the watch body 202 described with reference to FIGS. 2A-2C, 3, 4A, & 4B. The crown 210 may be integrally formed from a single piece of material that includes the shaft 1102 (that is, they may be connected to one another), or the shaft 1102 may be semi-permanently attached to a crown body 1104 using a fastening means such as solder, threads, or an adhesive. The crown 210 (or at least the crown body 1104) may be external to the housing 206, and may be rotated and/or translated by a user of the electronic device incorporating the crown assembly 1100. Further, although the crown body 1104 and shaft 1102 are shown as integrally formed in FIGS. 11A and 11B, it should be appreciated that they may be separate pieces that are joined together.

The crown assembly 1100 may further include a shaft retainer 1106 receiving an end of the shaft 1102. The shaft retainer 1106 may be mechanically and/or electrically connected to the shaft 1102 (e.g., using solder, threads, or an adhesive), interior to the housing 206. The shaft retainer 1106 may retain the crown 210 in position in relation to the housing 206.

One or more insulators 1108 (e.g., electrical insulators) may electrically insulate the crown 210 and/or shaft 1102 from the housing 206. The term "insulator" encompasses both a single insulator and multiple insulators taken as a set. The insulator 1108 is generally shown in FIG. 11 as an annular seal having an L-shaped profile, functioning as a collar for the shaft. The shaft 1102 and crown body 1104 may translate, moving toward and away from the housing 206 while the insulator 1108 and shaft retainer 1106 move with the shaft 1102. In some embodiments, the insulator 1108 may be stationary relative to the housing 206 while the shaft 1102, crown body 1104 and shaft retainer 1106 move.

The insulator 1108 or seal electrically insulates the shaft 1102 from the housing 206, and may also electrically insulate the housing 206 from the shaft retainer 1106. In some embodiments, the insulator 1108 may alternatively include more than one element and/or be positioned elsewhere within the crown assembly 1100. For example, the insulator 1108 may include an element, layer, or coating 1108a applied to a surface of the housing 206 that faces an underside of the crown 210, or to other elements that face the underside of the crown 210.

A tactile switch 1110 may be axially aligned with the shaft 1102 and positioned at an end of the shaft 1102 opposite the crown body 1104. By way of example, the tactile switch 1110 may be attached on a substrate 1112. The tactile switch 1110 may be actuated (e.g., switched between two or more states) as the shaft 1102 translates along an axis of the shaft 1102 to provide a crown input. A spring-biased conductor 1114 may be mechanically and electrically connected to at least one of the shaft 1102 or the shaft retainer 1106, and in FIG. 11 is shown to be connected to the shaft retainer 1106. The spring-biased conductor 1114 may be biased to electrically contact the shaft 1102 and/or shaft retainer 1106 during all phases of rotation and translation of the crown 210, and may electrically connect the shaft 1102 and/or shaft retainer 1106 to a circuit 1116 (e.g., a processor). When the crown is translated by a user, the spring-biased conductor 1114 may deform to maintain electrical contact with the shaft 1102 and/or shaft retainer 1106.

The crown assembly 1100 may further include an optical encoder 1118. The optical encoder 1118 may be used to detect rotation and/or translation of the shaft 1102 or shaft retainer 1106. In some embodiments, the circuit 1116 and optical encoder 1118 may be attached to the same substrate as the tactile switch 1110.

In some embodiments, the entirety of the crown 210 or crown body 1104 may be conductive and function as an electrode. The conductive crown body 1104 may be electrically connected to the circuit 1116 via the shaft 1102, shaft retainer 1106, and spring-biased conductor 1114. In other embodiments, only a portion of the crown 210 or crown body 1104 may be conductive and function as an electrode, and the conductive portion of the crown body 1104 may be electrically connected to the circuit 1116 via the shaft 1102, shaft retainer 1106, and spring-biased conductor 1114.

Because the signals received by or propagated from the crown 210 may be low voltage or low amplitude signals, the materials, positions, electrical connections to, and electrical routing paths for an electrode formed on or by the crown 210 can have a significant impact on the ability of the circuit 1116 to discern useful signals representing an ECG or other biological parameter of a person wearing an electronic device including the crown assembly 1100. The materials, positions, electrical connections to, and electrical routing paths for the crown assembly 1100 can also determine how well the crown assembly 1100 receives voltages/signals from a person's skin (e.g., a SNR of a device-to-user interface through which the voltages/signals pass); how well voltages/signals are transferred between the crown 210 and internal components of an electronic device (e.g., a voltage/signal propagation SNR); and how well the crown assembly 1100 operates in the face of environmental factors, such as temperature, humidity, moisture, electromagnetic radiation, dust, and so on. In some cases, the insulator 1108 may be positioned to prevent moisture from electrically shorting the crown 210 to the housing 206, or the housing 206 may be grounded to provide electrical shielding for some or all of the signals propagated through the crown assembly 1100, or the interfaces between the shaft 1102 and the shaft retainer 1106, or between the shaft retainer 1106 and the spring-biased conductor 1114, may be configured to increase SNR and reduce signal attenuation.

In some embodiments, the crown 210 may include a coating, layer, or the like 1120 ("coating 1120") that electrically isolates the crown 210. The coating may thus function as, have similar properties to, and/or be made from the same or similar materials as, the insulator 1108. Generally, the coating 1120 prevents electrical connection between the crown 210 and the housing 206, for example when water is present in the space between the crown and housing.

In the absence of the coating 1120, water, sweat, or another conductor may electrically bridge or short the crown 210 to the housing 206, presuming both the crown and housing are made from (or incorporate) an electrical conductor such as metal. In the event the crown 210 or some portion thereof serves as an electrode for measuring an electrocardiogram, shorting the crown 210 to the housing 206 (and thus to the skin of a wearer) may render the crown inoperable or the electrocardiogram unreliable.

The coating 1120 serves as a barrier against shorting the crown 210 to the housing 206 or other electrically conductive material or body, thereby ensuring the electrical functionality of the crown 210. In some embodiments the coating 1120 coats only those surfaces of the crown that oppose or face the housing; in other embodiments and as shown in FIG. 11A, the coating 1108a may extend across one or more sides of the crown 210. Further, the coating 1120 may extend onto a top or outer surface of the crown 210 (e.g., the surface of the crown that does not oppose or face the housing 206), although typically at least a portion of the outer surface is not covered by the coating in order to define an area of the crown that can electrically couple to a wearer's finger.

Figure 11B:
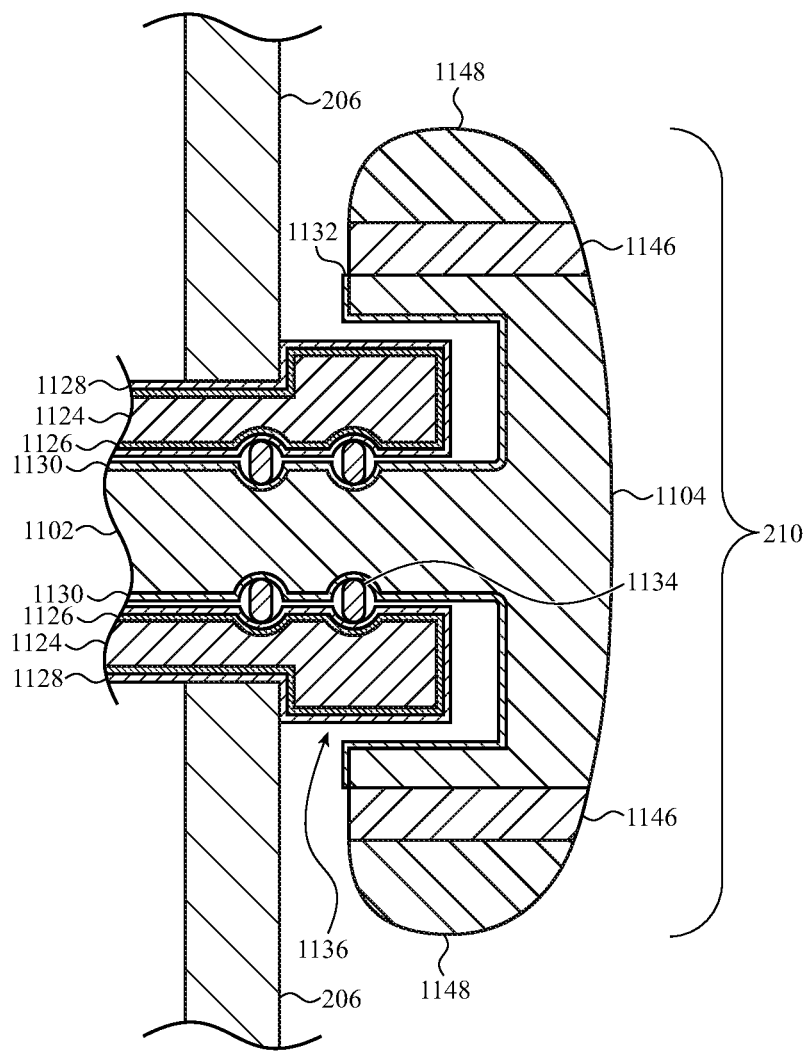
FIG. 11B is a cross-section of another example crown assembly.

The coating 1120 also may extend at least partly down a shaft of the crown 210, as discussed in more detail with respect to FIG. 11B.

In some embodiments, a second coating 1122 may be applied to the housing 206 instead of, or in addition to, the coating 1120 on the crown 210. This housing coating 1122 serves the same function as the crown coating 1120, namely electrically insulating the housing 206 from the crown 210 when water or other electrical conductors are in the gap between the housing and crown. The housing coating 1122 may extend across the insulator 1108 (or a non-insulating collar), in some embodiments. Likewise, the housing coating 1122 may extend between the housing 206 and insulator 1108 in some embodiments, or may be an extension of the insulator.

In some embodiments, the coatings 1120, 1122 may improve wear or provide a cosmetic function (e.g., provide an accent or visually conceal a surface of the shaft, crown, and/or housing) for the crown assembly 1100. Alternatively, the housing 206, or that portion of the housing 206 that faces the crown 210, may be formed from a material that operates as an electrical insulator (e.g., plastic, ceramic, or the like). In some embodiments, one or more of the insulators 1108 (including element, layer, or coating 1108a or 1120) may by overmolded liquid crystal polymer (LCP) elements or coatings, which can provide very good separation resistance (high separation resistance) between moving or other parts. LCP layers may also be used in place of polyimide layers in flex circuits and other elements, and may not require the use of temperature or moisture-sensitive adhesives. LCP elements, layers, and coatings absorb less moisture than polyimides in high temperature and high humidity environments, which can be useful in maintaining high separation resistance between components when sensing low voltage signals (e.g., biometric signals of a person) under varying conditions (e.g., under non-controlled conditions outside a doctor's office or hospital). LCP elements, layers, and coatings also maintain good separation resistance high temperatures. Other elements, layers, or coatings that may be used to provide electrical isolation include silicone or acrylic elements, layers, or coatings, or other elements having a high surface resistance. Other examples of insulators or insulator positions are described with reference to FIGS. 11B, 12A, 12B, 13, & 14.

FIG. 11B shows another example crown 210 extending through a housing 206 of an electronic watch. As with other embodiments described herein, the crown 210 may be used to provide multiple types of input. For example, the crown may rotate about an axis of rotation (typically extending along a center length of the shaft 1102, from an exterior of the housing 206 to an interior of the housing) to provide a first type of crown input, translate along the axis of rotation (e.g., move towards and/or away from the housing 206) to provide a second type of crown input, and be touch-sensitive to provide a third type of crown input. The first and second types of input may control graphical output on the electronic watch's display, as described below in more detail with respect to FIGS. 26A-28B. The third type of input may be a measurement of an electrical signal (such as voltage, capacitance, current, or the like), or facilitating measurements of a differential in an electrical signal, to provide an ECG of a user. That is and as discussed in greater detail herein, the third type of input may be the crown 210 functioning as one of two electrodes in an electrical circuit configured to measure a user's ECG. Typically, although not necessarily, the second electrode is positioned a back of the electronic watch. This second electrode and its functionality is discussed in more detail elsewhere in this document.

The crown 210 may be formed from multiple elements attached together, as discussed in more detail below, or may be a single piece and connected to one another. The crown 210 generally includes a crown body 1104 coupled to (or formed with) a shaft 1102. The shaft 1102 of the crown may extend through the housing 206 and is typically received in, or passes through, a collar 1124. The collar 1124 may restrict tilting of the shaft 1102 and crown body 1104. Further, the collar 1124 may permit translation of the shaft 1102 and crown body 1104 toward and away from the housing and rotation of the shaft and crown body 1104 about the axis of rotation. The collar 1124 may be the same as, or similar to, the shaft retainer 1106 and/or insulator 1108 of FIG. 11A.

One or more O-rings 1134 are fitted about the shaft 1102 and within the collar 1124. The O-rings 1134 may be received within grooves, depressions, or the like within one or both of the shaft 1102 and collar 1124. The O-rings form a watertight seal and likewise reduce or eliminate contaminants passing into an interior of the housing 206 through the gap 1136 between the crown 210 and housing 206. The O-rings 1134 may also permit the shat to rotate and/or translate while restricting (or helping to restrict) how far the shaft 1102 translates.

As with the embodiment shown in FIG. 11A, the crown 210 may short to the housing 206 if water or another conductor is present in the gap 1136 between the crown and housing and the two are not electrically insulated from one another. Shorting the crown 210 to the housing 206 results in the electronic watch unreliably measuring and displaying an ECG of a user or not functioning at all.

Accordingly and similar to the embodiment of FIG. 11A, an underside of the crown 210 may be coated with an electrically insulating coating 1132. The coating 1132 may prevent water or another contaminant from acting as a short or ground path between the crown 210 and housing 206. As discussed with respect to FIG. 11A and shown in that figure, such a coating may be applied to the housing 206 in addition to, or instead of, the crown 210.

The crown 210 shown in FIG. 11B is not formed from a single piece of material but instead is formed from multiple elements. The crown body 1104 and shaft 1102 may be formed from or as a single piece of material, for example metal or another suitable conductor, and provide an electrical path between an object touching the crown body 1104 and a sensor within the housing 206, such as the third sensor 230 discussed above. An insulating split 1146 may separate the crown body from a trim 1148; the trim 1148 may be annular, square, or any other suitable shape. The trim and split 1146 may provide various aesthetic looks as well as functional properties, such as different wear resistance, environmental resistance, and the like as compared to the crown body 1104. Accordingly, the trim 1148 may be made from the same material or a different material as the crown body 1104 and the shaft 1102.

Insofar as the split 1146 is an electrical insulator, the coating 1132 need not extend across the split or onto any portion of the trim 1148 (although it can in some embodiments). Thus, the coating 1132 may stop at an edge of the crown body 1104 abutting the split 1146. This may reduce manufacturing and assembly complexity of embodiments, as well as provide cost savings.

In addition to, or instead of, providing a coating 1132 on the crown 210 or housing 206, the collar 1124 may be coated. For example, an electrically insulating coating 1126 may be deposited on the collar 1124 and serve to electrically insulate the collar from the housing 206 and/or crown 210. This may be useful when the collar is made from an electrically conductive material and the crown 210 may be shorted to the collar 1124, in addition to or instead of to the housing 206.

As one non-limiting example, capillary action may retain water (or another liquid) in a portion of the gap between the collar 1124 and crown 210 while the part of the gap 1136 between the crown and housing 206 is sized to permit water to drain out. Thus, in such an embodiment the crown 210 may be at risk of electrically shorting to the collar 1124 but not the housing 206. It should be appreciated that in some embodiments the housing 206 and/or crown 210 may be coated as well as the collar 1124. It should likewise be appreciated that any or all of the electrically insulating coatings described herein may attenuate noise with respect to a signal conducted from the crown body 1104 through the shaft 1102 to a sensor, thereby providing more accurate and/or faster readings of a biological parameter such as an ECG.

Although the coating 1126 (and coating 1132) has been discussed as an electrical insulator, it should be appreciated that the coating(s) may provide other properties in addition to, or instead of, electrical insulation. For example, the coating 1126 may reduce friction between the collar 1124 and shaft 1102 as the shaft 1102 rotates and/or translates. The coating 1126 may reduce wear on either or both of the collar 1124 and shaft 1102 as another example.

Further, in some embodiments the gap 1136 between the crown 210 and housing 206 may be large enough that the collar 1124 may be visible. In order to obscure the first collar coating and/or the collar, a second collar coating 1128 may be applied over the first, insulating collar coating 1126. The second collar coating 1128 may be darker or otherwise visually conceal the first collar coating 1128 and collar 1124 from the naked eye.

As yet another option, the second coating 1128 may also provide environmental resistance and/or resist wear, tear, and/or friction between the collar 1124 and shaft 1102, as described above. Thus, the first collar coating 1126 may be an electrical insulator while the second collar coating 1128 may be chosen for its other material properties and/or resistances. Similarly, the first collar coating may be chosen for its material properties and/or resistances (including functioning as an electrical insulator) and the second collar coating may be used to obscure the first collar coating.

Any or all of the coatings described herein may be deposited in a number of ways, including electrophoretic deposition or other manners that are suitable and known in the art. Likewise, any or all of the coatings may incorporate materials such as titanium dioxide, Teflon, or the like to provide or enhance properties such as resistance to wear, lowering of friction between adjacent elements, and the like. In some embodiments the first collar coating 1126 (or any other coating) may be approximately 10-30 microns thick or even 5-50 microns. The second collar coating 1128 (or any other coating) may be thinner on the order of 3-5 microns or even 2-10 microns.

More detailed examples of the crown assembly 1100 described with reference to FIG. 11A are shown in FIGS. 12A, 12B, 13, & 14.

Figure 12A:
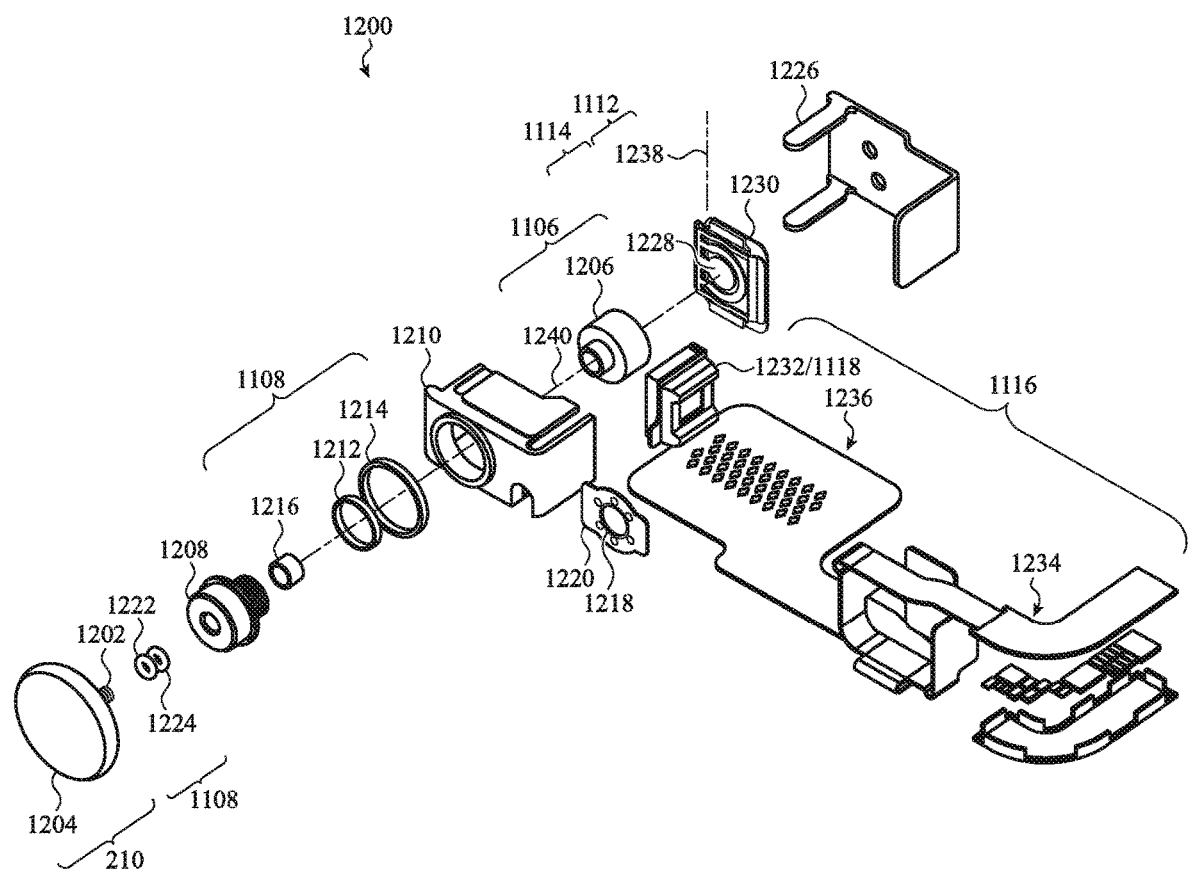
FIGS. 12A & 12B show another example of a crown assembly.
Figure 12B:
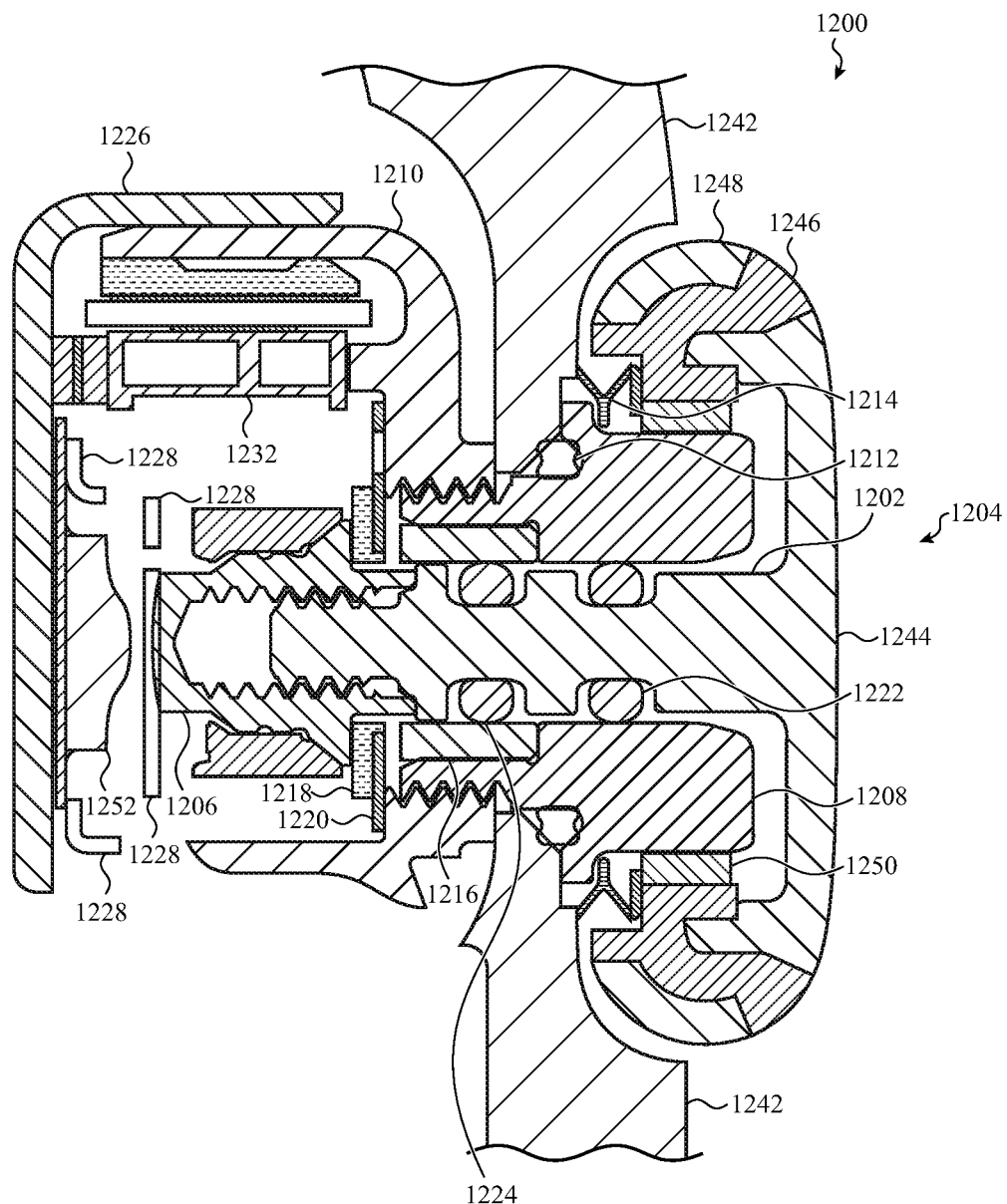

Turning now to FIGS. 12A & 12B, there is shown an example of a crown assembly 1200, as may be included in any of the electronic devices described with reference to FIGS. 1A, 1B, 2A-2C, 3, 4A, or 4B. FIG. 12A shows an exploded view of the crown assembly 1200, and FIG. 12B shows an assembled cross-section of the crown assembly 1200, as viewed from the front or rear face of an electronic device such as the watch body 202 described with reference to FIGS. 2A-2C, 3, 4A, & 4B.

The crown assembly 1200 is an example of the crown assembly 1100 shown in FIG. 11, and includes components corresponding to the crown 210, shaft retainer 1106, insulator 1108, tactile switch 1110, substrate 1112, spring-biased conductor 1114, circuit 1116, and optical encoder 1118.

The crown assembly 1200 may include a conductive rotatable shaft 1202 configured to extend through an opening in a housing 1242 (see FIG. 12B), such as the housing described with reference to FIG. 2A, 2C, 3, 4A, 4B, or 11. A user-rotatable crown 1204 may be mechanically attached to the shaft 1202 exterior to the housing 1242. The crown 1204 may be rotated by a user of an electronic watch, to in turn rotate the shaft 1202. In some cases, the crown 1204 may also be pulled or pushed by the user to translate the shaft 1202 along its axis. The crown 1204 may be electrically connected to a circuit within the housing 1242, but electrically isolated from the housing 1242.

The crown 1204 may be electrically connected to the shaft 1202. In some cases, at least part of the crown 1204 and at least part of the shaft 1202 may be molded, machined, or otherwise formed together (e.g., from a same material, such as a conductive ceramic or stainless steel).

In some embodiments, the crown 1204 may be formed of a conductive ceramic or stainless steel (or have a conductive ceramic or stainless steel core). The core may be coated in a PVD deposited layer of SUS or DLC, or an electrodeposited (ED) layer of AlTiN or CrSiCN, and may function as an electrode. In some embodiments, the crown 1204 may have a conductive crown body 1244 surrounded by a ring 1246 of non-conductive material (or other insulator). See, FIG. 12B. The non-conductive ring 1246 may help prevent shorting of the crown 1204 to the housing 1242. The ring 1246 of non-conductive material may in some cases be surrounded by another ring 1248 of conductive material. In the configuration shown, the ring 1248 may optionally contact and electrically short to a grounded housing 1242 when the crown is pressed, thereby helping to electrically shield the conductive crown body 1244 of the crown 1204 from some sources of interference. In some embodiments, the crown 1204 may have a conductive surface covered by a thin non-conductive coating. The non-conductive coating may provide a dielectric for capacitive coupling between the conductive surface and skin of a user of the crown 1204 (or an electronic watch or other device that includes the crown assembly 1200). In the same or different embodiments, the crown 1204 may have a non-conductive coating on a surface of the crown 1204 facing the housing 1242.

A shaft retainer 1206 may be mechanically connected to the shaft 1202, interior to the housing 1242 (e.g., interior to a watch body housing), after the shaft is inserted through the opening in the housing 1242 with the crown 1204 positioned exterior to the housing 1242. In some cases, the shaft retainer 1206 may include a nut, and the shaft 1202 may have a threaded male portion that engages a threaded female portion of the nut. In some cases, the shaft retainer 1206 may be conductive, or have a conductive coating thereon, and mechanical connection of the shaft retainer 1206 to the shaft 1202 may form an electrical connection between the shaft retainer 1206 and the shaft 1202. In an alternative embodiment (not shown), the shaft retainer 1206 may be integrally formed with the shaft 1202, and the shaft 1202 may be inserted through the opening in the housing 1242 from inside the housing 1242 and then attached to the crown 1204 (e.g., the crown 1204 may screw onto the shaft 1202).

In some embodiments, a collar 1208 may be aligned with the opening in the housing 1242, and a collar retainer 1210 may be coupled to the collar 1208 to retain the collar 1208 to the housing 1242 from a side of the housing 1242 opposite a side of the housing 1242 in which the collar 1208 is inserted. In some embodiments, the collar retainer 1210 may be coupled to the collar 1208 via threads on a male portion of the collar 1208 and corresponding threads on a female portion of the collar retainer 1210. Optionally, a gasket 1212 (e.g., an I-ring) made of a synthetic rubber and fluoropolymer elastomer (e.g., Viton), silicone, or another compressible material may be placed over the collar 1208 prior to insertion of the collar 1208 through the opening, and attachment of the collar retainer 1210 to the collar 1208 may compress the gasket 1212. The compressed gasket 1212 may provide stability to the collar 1208 and collar retainer 1210, or provide a moisture barrier between the collar 1208 and the housing 1242. The collar 1208 and collar retainer 1210 may be attached to one another, and thereby to the housing 1242, prior to insertion of the shaft 1202 through the collar 1208. Another gasket 1214 (e.g., a Y-ring) made of Viton, silicone, or another compressible material may be placed over the collar 1208, before or after insertion of the collar 1208 through the opening, but before the shaft 1202 is inserted through the collar 1208. The second gasket 1214 may provide a moisture barrier between the crown 1204 and the housing 1242 or the crown 1204 and the collar 1208.

Also prior to inserting the shaft 1202 through the collar 1208, and in some cases prior to inserting the collar 1208 into the opening in the housing 1242, an insulator 1216 may be inserted into or deposited on the interior of the collar 1208, or placed around or deposited on the shaft 1202. The insulator 1216 may also be inserted, placed, or deposited as the shaft 1202 is inserted into the collar 1208. In some cases, the insulator 1216 may include a non-conductive sleeve or bushing (e.g., a plastic sleeve) inserted (e.g., press-fit) into the collar 1208 (e.g., into a portion of the collar 1208 positioned interior to the housing 1242). The insulator 1216 may also or alternatively include a non-conductive sleeve overmolded on the collar (e.g., molded within the opening in the collar 1208 and over a surface of the collar 1208 facing the crown 1204). In some cases, the insulator 1216 may be an overmolded liquid crystal polymer (LCP) insulator 1216. The insulator 1216 may also or alternatively include a non-conductive coating on the collar 1208 (e.g., on an inner surface of the collar 1208), or a non-conductive coating on the shaft 1202, or a set of one or more non-conductive gaskets surrounding the shaft 1202. When the shaft 1202 is inserted into the collar 1208, the insulator 1216 may be positioned between the shaft 1202 and the collar 1208 and help to insulate a conductive portion of the shaft 1202 (or the entire shaft 1202) from the collar 1208.

Another insulator 1218 may be positioned between the shaft retainer 1206 and the collar retainer 1210. For example, a non-conductive (e.g., plastic) washer, plate, or shim may be attached to the interior of the collar retainer 1210, between the shaft retainer 1206 and the collar retainer 1210. In some cases, the non-conductive washer may be carried by a plate 1220, such as a plate formed of stainless steel (e.g., the insulator 1218 may be an overmolded LCP insulator 1218). In these cases, the non-conductive washer may be attached to the interior of the collar retainer 1210 by welding (e.g., laser welding) the plate 1220 to the collar retainer 1210. The non-conductive washer or other element may provide a bearing surface for the shaft retainer 1206.

As shown in FIGS. 12A & 12B, one or more O-rings 1222, 1224 or other gaskets may be placed over the shaft 1202 before the shaft 1202 is inserted into the collar 1208. The O-rings 1222, 1224 may be formed of a synthetic rubber, fluoropolymer elastomer, silicone, or another compressible material. The O-rings 1222, 1224 may maintain the shaft 1202 in a position that is centered within the collar 1208. In some cases, the O-rings 1222, 1224 may provide a seal between the shaft 1202 and the collar 1208. The O-rings 1222, 1224 may also function as an insulator between the shaft 1202 and the collar 1208. In some embodiments, the O-rings 1222, 1224 may be fitted to recesses in the shaft 1202. Additionally, a low-friction ring 1306 or filler may be placed around the top of the collar 1208, between the crown 1204 and the collar 1208. Alternatively, the low-friction ring 1250 or filler may be attached to the crown 1204, between the crown 1204 and the collar 1208. In some embodiments, the shaft 1202 may be smooth (not shown) and rotate within a thicker or closer fitting insulator 1216 without use of the O-rings 1222, 1224.

In some embodiments, a bracket 1226 may be attached (e.g., laser welded) to the collar retainer 1210 or another element within the housing 1242. The bracket 1226 may support a spring-biased conductor 1228 and maintain the spring-biased conductor 1228 in mechanical and electrical contact with the shaft retainer 1206 (or in some cases with an end of the shaft 1202, such as when the shaft extends through the shaft retainer (not shown)). As shown, the spring-biased conductor 1228 may include a shear plate that is spring-biased about an axis 1238, which axis 1238 is perpendicular to and radially outward from a second axis 1240 of the shaft 1202. By way of example, the shear plate is shown to be circular, although the shear plate could also have other shapes. In some embodiments, the surface of the shear plate that abuts the shaft retainer 1206 or shaft end may be hardened (e.g., with a PVD deposited coating of cobalt chromium (CoCr or hard chromium)) to mitigate the likelihood of the shaft retainer 1206 or shaft end wearing through the shear plate after multiple rotations or translations of the shaft 1202. The shear plate (and in some cases the entirety of the spring-biased conductor 1228) may be plated with gold or another material to improve electrical conductivity (e.g., prior to coating the shear plate with a hardener). In some cases, the spring-biased conductor 1228 may be formed (e.g., stamped or bent) from a piece of metal (e.g., stainless steel). In other cases, the spring-biased conductor 1228 may be formed in other ways. The length and thickness of the shear plate, perpendicular to the axis of the shaft 1202, can be optimized to provide a balance between a high enough spring constant to ensure good electrical contact between the shear plate and the shaft retainer 1206 or shaft end (even during rotation of the shaft 1202), on one hand, and a low enough spring constant to mitigate the likelihood that the shaft retainer 1206 or shaft end will wear through the shear plate (or through a coating thereon). A flat or relatively flat shear plate can reduce the dimension of the crown assembly 1200 along the axis 1240 of the shaft 1202.

In some embodiments, a majority or entirety of the shaft 1202, shaft retainer 1206, or crown 1204 may be coated with a non-conductive coating, but for an external conductive surface of the crown 1204 and a portion of the shaft 1202 or shaft retainer 1206 that contacts the spring-biased conductor 1228.

When the shaft 1202 is translatable, translation of the shaft 1202 into the housing 1242 (e.g., into the housing of a watch body) may cause the spring-biased conductor 1228 (or the shear plate thereof) to deform. However, the spring bias of the spring-biased conductor 1228 may cause the spring-biased conductor 1228 (or the shear plate thereof) to maintain electrical contact with the shaft retainer or shaft end, regardless of whether the shaft 1202 is in a first position or a second position with reference to translation of the shaft 1202. The spring-biased conductor 1228 may be electrically connected to a circuit, such as a circuit formed on or in a substrate 1230 such as a flex circuit or printed circuit board (PCB). In some cases, the spring-biased conductor 1228 may be surface-attached to the circuit substrate 1230 (such as soldered or otherwise mechanically connected, for example by using a surface-mount technology process), which circuit substrate 1230 may be supported by the rigid support member (or sub-housing frame member) 1226. A conductive grease may be deposited between the shaft retainer 1206 or shaft 1202 and the shear plate or other member of the spring-biased conductor 1228. The circuit may be in electrical communication with the crown 1204 via the spring-biased conductor 1228, the shaft retainer 1206, and the shaft 1202 (or when an end of the shaft 1202 protrudes through the shaft retainer 1206, the circuit may be in electrical communication with the crown 1204 via the spring-biased conductor 1228 and the shaft 1202).

A tactile (tac) switch 1252, such as a dome switch, may be electrically connected to the circuit and mechanically connected to the circuit substrate 1230. In some cases, the tac switch 1252 may be surface-attached to the circuit substrate 1230 (such as soldered or otherwise mechanically connected). The shear plate of the spring-biased conductor 1228 may be positioned between the shaft retainer 1206 and the tac switch 1252. The tac switch 1252 may be actuated or change state in response to translation of the shaft 1202. Thus, when a user presses on the crown 1204, the shaft 1202 may translate into the housing 1242 (e.g., into the housing of a watch body) and actuate the tac switch 1252, placing the tac switch 1252 in one of a number of states. When the user releases pressure on the crown 1204 or pulls the crown 1204 outward from the housing 1242, the tac switch 1252 may retain the state in which it was placed when pressed, or advance to another state, or toggle between two states, depending on the type or configuration of the tac switch 1252.

The circuit to which the tac switch 1252 and spring-biased conductor 1228 are electrically connected may be part of, or electrically connected to, one or more circuits that carry portions of an optical encoder 1232 and other circuit elements, such as an interface 1234 to the electrodes described with reference to FIGS. 5C, 5D, 5E, 6-8, 9A-9C, & 10A-10D, or a processor that receives and processes signals received from or provided to the crown 1204 or other electrodes. By way of example, FIG. 12A shows a circuit 1236 (e.g., a flex circuit or PCB) to which a set of one or more light emitters and light detectors of an optical encoder 1232 is connected. The light emitter(s) may illuminate an encoder pattern or other rotating portion of the optical encoder 1232, which encoder pattern or other rotating portion of the optical encoder 1232 may be carried on (e.g., formed on, printed on, etc.) the shaft retainer 1206. The light detector(s) may receive reflections of the light emitted by the light emitter(s), and a processor may determine a direction of rotation, speed of rotation, angular position, translation, or other state(s) of the crown 1204 and shaft 1202.

The spring-biased conductor 1228 may be connected to a processor. The processor may be attached or coupled to one or more of the circuits shown in FIG. 12A. The processor may determine whether a user is touching the crown 1204, or determine a biological parameter of the user based on a signal received from or provided to the user via the crown 1204, or determine other parameters based on signals received from or provided to the crown 1204. In some cases, the processor may operate the crown and electrodes described in FIGS. 5C, 5D, 5E, 6-8, 9A-9C, 10A-10D, 11, 12A, & 12B as an electrocardiogram and provide an ECG to a user of a watch including the crown and electrodes.

In an alternate embodiment of the crown assembly 1200 shown in FIGS. 12A & 12B, the spring-biased conductor 1228 may include a conductive brush that is biased to contact a side of the shaft 1202 or a side of the shaft retainer 1206. The conductive brush may maintain electrical contact with the shaft 1202 or shaft retainer 1206 through rotation or translation of the shaft 1202, and may be electrically connected to a circuit such as the circuit that supports the tac switch 1352.

Figure 13:
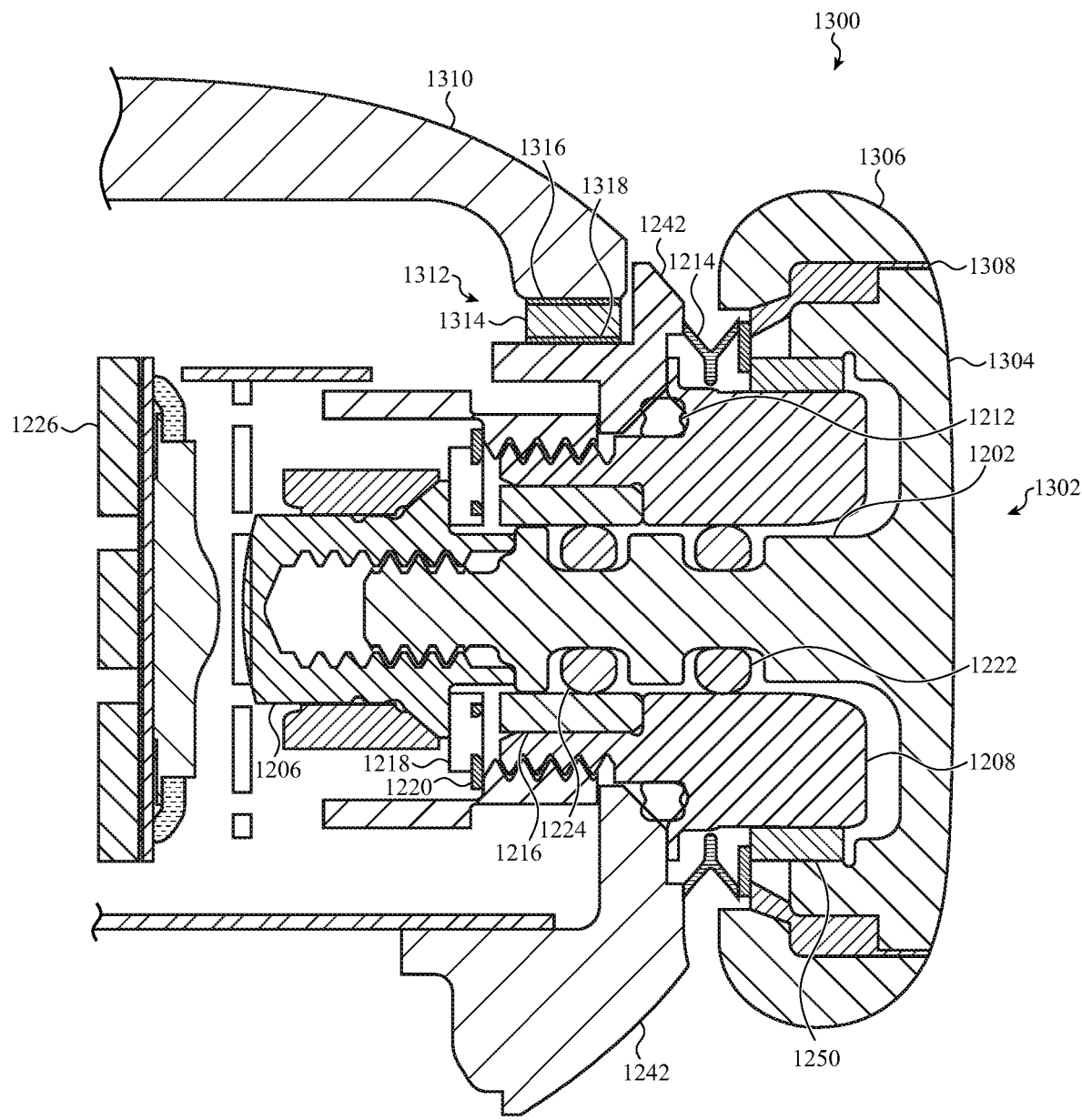
FIGS. 13 & 14 show cross-sections of additional examples of crown assemblies.

FIG. 13 shows a cross-section of a crown assembly 1300 as viewed from an edge of a watch body (e.g., an edge to which a watch band might be attached). The crown assembly 1300 differs from the crown assembly 1200 shown in FIGS. 12A & 12B in that the crown 1302 has a somewhat different configuration. For example, the crown 1302 has a conductive crown body 1304 surrounded by a non-conductive ring 1306. The non-conductive ring 1306 may be attached to the conductive crown body 1304 by an adhesive 1308. Alternatively, the ring 1306 may be conductive, and may be insulated from the conductive crown body 1304 by the adhesive 1308 (e.g., when the adhesive 1308 is non-conductive) or electrically connected to the conductive crown body 1304 (e.g., when the adhesive 1308 is conductive).

As shown in FIG. 13, the crown assembly 1300 may be positioned adjacent a transparent cover 1310 (e.g., a carrier) under which a display may be attached, such that the display is at least partially or fully within the housing. In some cases, the display may be a touch-sensitive display. In some embodiments, the display may also be a force-sensitive display. FIG. 13 shows one example of a force sensor 1312 for a force-sensitive display, in which a compressible gasket 1314 is bounded by first and second capacitive plates 1316, 1318 and positioned between the carrier 1310 and the housing 1242.

Figure 14:
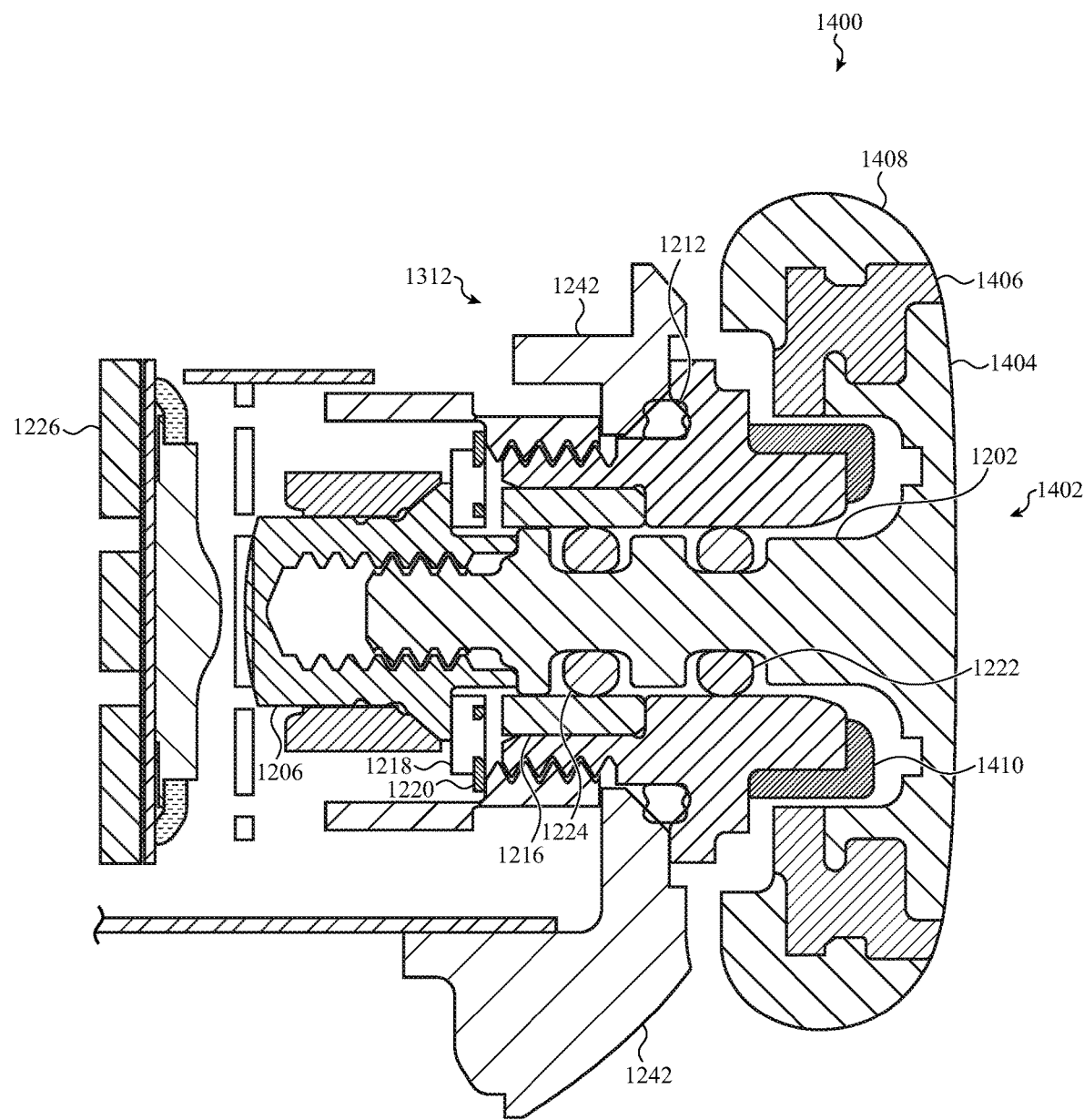

FIG. 14 shows a cross-section of a crown assembly 1400, as may be included in any of the electronic devices described with reference to FIG. 1A, 1B, 2A-2C, 3, 4A, or 4B. Similarly to the crown assemblies 1200 and 1300 shown in FIGS. 12A, 12B, & 13, the crown assembly 1400 is an example of the crown assembly 1100 shown in FIG. 11.

The crown assembly 1400 is similar to the crown assembly 1200 in that its crown 1402 has a conductive crown body 1404 surrounded by an inner ring 1406 of non-conductive material and an outer ring 1408 of conductive material. The conductive crown body 1404 may be formed of a conductive ceramic or stainless steel, and may be coated in a PVD deposited layer of SUS or DLC, or an ED layer of AlTiN or CrSiCN, and may function as an electrode. The non-conductive inner ring 1406 may help prevent shorting of the crown 1402 to the housing 1242, and may be formed of a plastic or elastomer, for example. The conductive outer ring 1408 may be formed of the same or different material(s) as the conductive crown body 1404.

The non-conductive inner ring 1406 may extend from an outer surface of the crown 1402 to under a portion of the conductive crown body 1404. In this manner, the non-conductive inner ring 1406 may prevent the conductive crown body 1404 from contacting the collar 1208 when the crown 1402 is translated toward the housing 1242.

The conductive outer ring 1408 may extend from an outer surface of the crown 1402 to under a portion of the non-conductive inner ring 1406. In this manner, if the housing 1242 is grounded and the conductive outer ring 1408 contacts the housing 1242, the conductive outer ring 1408 may be grounded to the housing 1242.

In contrast to the crown assemblies 1200 and 1300, the crown assembly 1400 has an insulator 1410 (e.g., a non-conductive element, layer, or coating) applied to at least one surface of the collar 1208 (e.g., to at least a portion of the surface or surfaces that face an underside of the conductive crown body 1404). The insulator 1410 may further prevent the conductive crown body 1404 from contacting the collar 1208 when the crown 1402 is translated toward the housing 1242 and may provide increased separation resistance between the collar 1208 and the crown 210. In some embodiments, the insulator 1410 may include a layer of plastic that is overmolded (e.g., LCP overmolded) on at least a portion (or all) of the collar 1208 that faces the crown 210 (or a plastic element that is placed over or adhered to at least a portion (or all) of the collar 1208, or a coating that is applied to at least a portion of the collar 1208). In some embodiments, the plastic may extend to adjacent surfaces of the housing 206, or into the central opening in the collar 1208. In some embodiments, the insulator 1410 may include a coating (e.g., an electro-deposited (ED) acrylic-based polymer coating). Alternatively or additionally, an insulator (e.g., an element, layer, or coating) may be applied to the underside of the conductive crown body 1404, or to surfaces of the shaft 1202 that face the collar 1208 and/or housing 206. Alternatively, the collar 1208 may be formed from plastic or another material that is non-conductive or otherwise electrically isolates the conductive crown body 1404 of the crown 1402, or the shaft 1202, from other conductive components of the crown assembly 1500.

In any of the crown assemblies 1200, 1300, 1400 described in the present disclosure, the crown 1204, 1302, or 1402 may alternately be a monolithic structure and not include additional conductive or non-conductive rings, or may include a single non-conductive (e.g., plastic) ring surrounding a conductive central portion.

Figure 15:
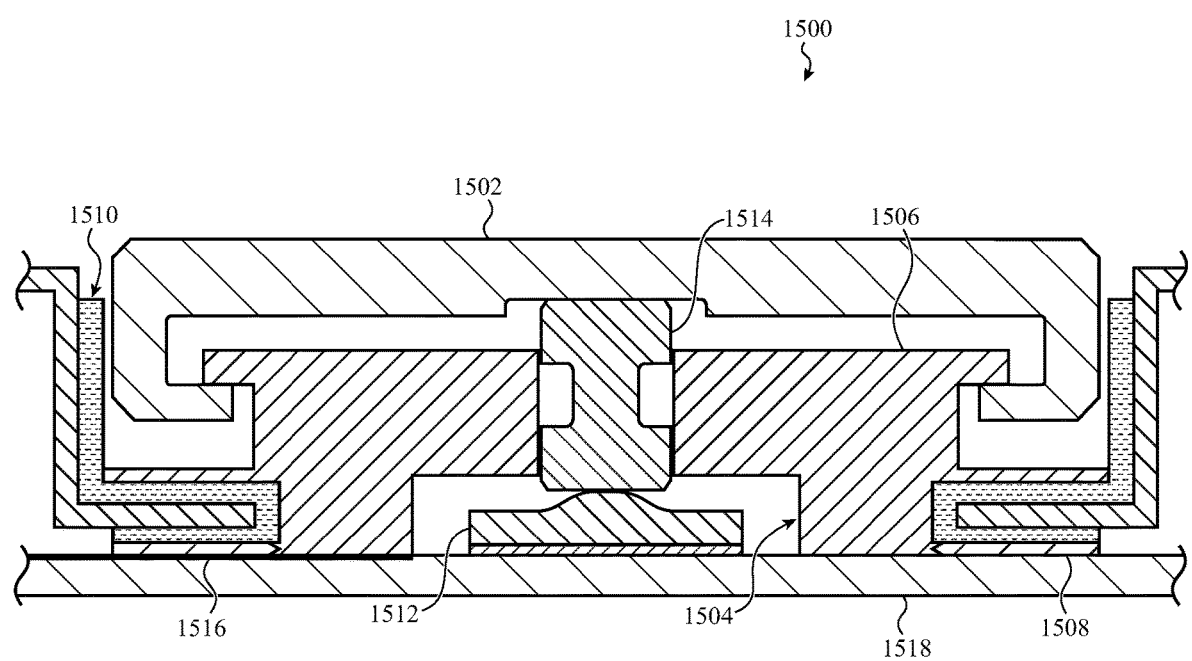
FIGS. 15-22 show various examples of button assemblies.

Turning now to the implementation of an electrode on a button, FIG. 15 shows an example cross-section of a button assembly 1500. The button assembly 1500 may be an example of a button assembly included in any of the electronic devices described with reference to FIG. 1A, 1B, 2A-2C, 3, 4A, or 4B.

The button assembly 1500 may include a conductive button cap 1502. The conductive button cap 1502 may be retained within an opening in a housing by a button cap retention assembly 1504. The button cap retention assembly 1504, or parts thereof, may be conductive. By way of example, the housing is shown to be the housing 206 of the watch body 202 described with reference to FIGS. 2A-2C, 3, 4A, & 4B. The button cap retention assembly 1504 may be attached to the housing 206 and extend through the opening in the housing 206. In some embodiments, the button cap retention assembly 1504 may include a first component 1506 that is inserted through the opening from one side of the housing 206, and a second component 1508 that fastens to the first component 1506 on the other side of the housing 206 (e.g., by threads, screws, solder, or an adhesive).

A set of one or more insulators 1510 (e.g., electrical insulators) may electrically insulate the button cap retention assembly 1504 from the housing 206. The insulator 1510 may also electrically insulate the conductive button cap 1502 from the housing 206. Although the insulator 1510 is generally shown in FIG. 15 as a singular annular seal around the perimeter of the button assembly 1500, the insulator 1510 may alternatively include more than one element or be positioned elsewhere within the button assembly 1500, as described with reference to FIGS. 16A, 16B, 17A, 17B, 18A, & 18C.

The conductive button cap 1502 may translate toward and away from the housing 206, and may be in electrical contact with the button cap retention assembly 1504 during all phases of translation. When the conductive button cap 1502 is pressed by a user and translates toward the housing 206, a tactile switch 1512 may be actuated (e.g., switched between two or more states). A shaft 1514 may extend from an interior surface of, or be formed integrally with, the conductive button cap 1502 and a depressible surface of the tactile switch 1512. The tactile switch 1512 and shaft 1514, or other elements not shown in FIG. 15 (e.g., springs), may bias the conductive button cap 1502 in an outwardly translated position.

The conductive button cap 1502 may function as an electrode, and an electrical signal may be routed between the conductive button cap 1502 and a circuit 1516, at least in part, via the button cap retention assembly 1504. In some embodiments, the button cap retention assembly 1504, tactile switch 1512, and circuit 1516 may be attached to a common substrate 1518.

Because the signals received by or propagated from the conductive button cap 1502 may be low voltage or low amplitude signals, the materials, positions, electrical connections to, and electrical routing paths for an electrode formed on or by the conductive button cap 1502 can have a significant impact on the ability of the circuit 1516 to discern useful signals representing an ECG or other biological parameter of a person wearing an electronic device including the button assembly 1500. The materials, positions, electrical connections to, and electrical routing paths for the button assembly 1500 can also determine how well the button assembly 1500 receives voltages/signals from a person's skin (e.g., a SNR of a device-to-user interface through which the voltages/signals pass); how well voltages/signals are transferred between the conductive button cap 1502 and internal components of an electronic device (e.g., a voltage/signal propagation SNR); and how well the button assembly 1500 operates in the face of environmental factors, such as temperature, humidity, moisture, electromagnetic radiation, dust, and so on. In some cases, the insulator 1510 may be positioned to prevent moisture from electrically shorting the conductive button cap 1502 to the housing 206, or the housing 206 may be grounded to provide electrical shielding for some or all of the signals propagated through the button assembly 1500.

More detailed examples of the button assembly 1500 described with reference to FIG. 15 are shown in FIGS. 16A, 16B, 17A, 17B, 18A, & 18B.

Figure 16A:
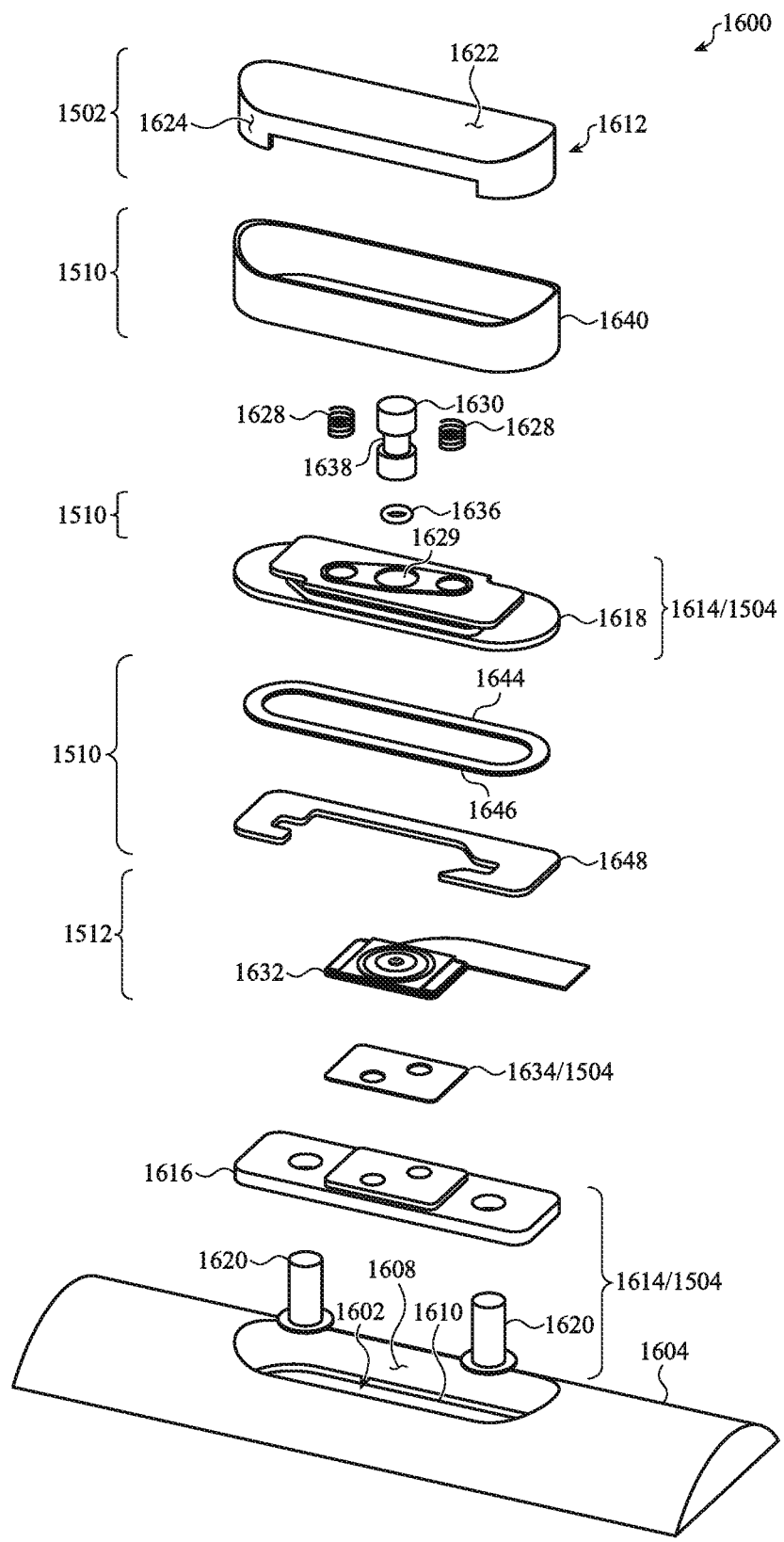
Figure 16B:
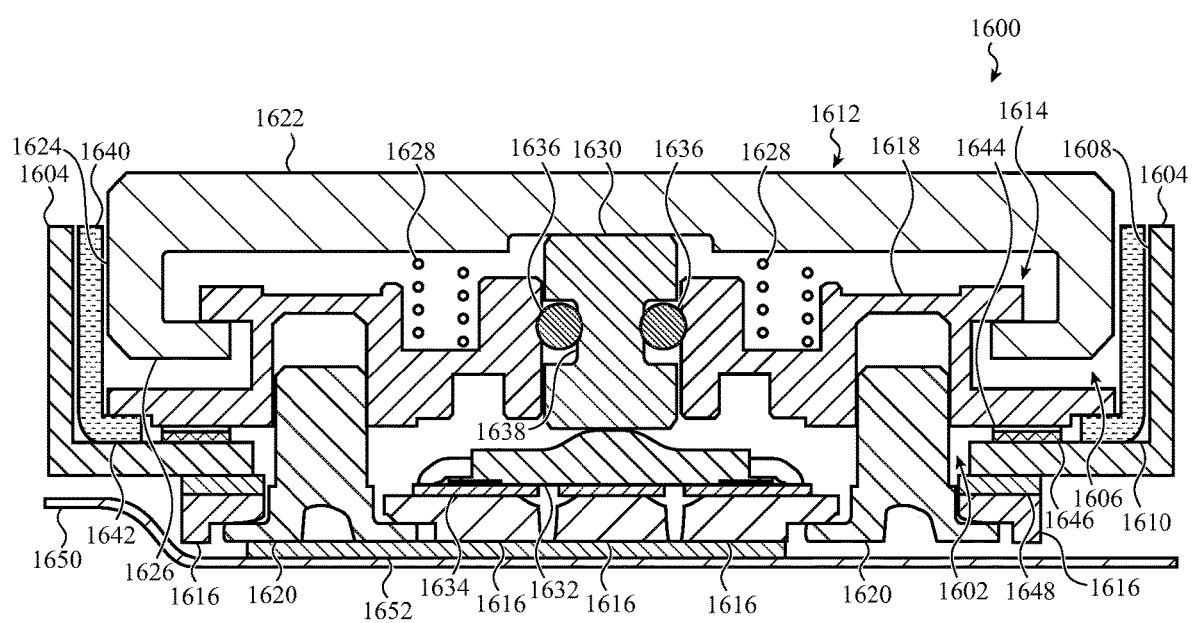

Turning now to FIGS. 16A & 16B, there is shown an example of a button assembly 1600 that may be included in any of the electronic devices described with reference to FIG. 1A, 1B, 2A-2C, 3, 4A, or 4B. FIG. 16A shows an exploded view of the button assembly 1600, and FIG. 16B shows an assembled cross-section of the button assembly 1600, as viewed from the front or rear face of an electronic device such as the watch body 202 described with reference to FIGS. 2A-2C, 3, 4A, and 4B.

The button assembly 1600 is an example of the button assembly 1500 shown in FIG. 15, and includes components corresponding to the conductive button cap 1502, button cap retention assembly 1504, insulator 1510, and tactile switch 1512.

The button assembly 1600 may be at least partially within an opening 1602 in a housing 1604 (e.g., an opening in the housing described with reference to FIG. 2A, 2C, 3, 4A, or 4B), and attached to the housing or an internal structure. In some cases, and as shown, the housing 1604 may include a cavity 1606 (FIG. 16B) defined by a sidewall 1608 and a ledge 1610. The ledge 1610 may surround the opening 1602, and the sidewall 1608 may surround the ledge 1610.

The button assembly 1600 may include a conductive button cap 1612. The conductive button cap 1612 may be retained by a button cap retention assembly 1614, and may be translatable toward and away from the housing 1604. The button cap retention assembly 1614 may extend through the opening 1602 and be attached to the housing 1604. In some examples, the button cap retention assembly 1614 may include a bracket 1616 that overlaps the ledge 1610 interior to the housing 1604, and a retainer 1618 that overlaps the ledge 1610 exterior to the housing 1604. The retainer 1618 may be mechanically attached to the bracket 1616 by a set of screws 1620 or other mechanical fastener. The screws 1620 may be inserted into through-holes in the bracket 1616 and screwed into threaded holes in the retainer 1618, clamping the ledge 1610 between the bracket 1616 and the retainer 1618.

The conductive button cap 1612 may have an exterior surface 1622, a sidewall or set of sidewalls 1624 parallel to the sidewall 1608 of the cavity 1606, and an inward facing lip or set of lips 1626 (FIG. 16B) that extends between the retainer 1618 and the ledge 1610 and toward a center axis of the conductive button cap 1612. A set of one or more coil springs 1628 or other spring-biased members may be positioned between an outer surface of the retainer 1618 and an underside of the conductive button cap 1612, and may bias the conductive button cap 1612 in an outward state of translation.

The button cap retention assembly 1614, and in particular the retainer 1618, may have a through-hole 1629 defined therein, with an axis of the through-hole 1629 extending perpendicular to the opening 1602 in the housing 1604. A shaft 1630 may be positioned within the through-hole 1629, and may translate toward and away from the housing 1604. The shaft 1630 may be mechanically connected to the conductive button cap 1612, or may be biased to contact the conductive button cap 1612. By way of example, the shaft 1630 may be non-conductive. In a state of rest, the shaft 1630 and conductive button cap 1612 may be biased in an outward state of translation (i.e., away from the opening 1602) by the coil springs 1628 and/or a spring-biased tactile switch 1632. When a user presses the conductive button cap 1612 toward the housing 1604, the press may overcome the bias provided by the coil springs 1628 and/or tactile switch 1632, and pressure on the conductive button cap 1612 may be transferred to the shaft 1630, which translates toward the housing 1604 and presses on the tactile switch 1632 to change the state of the tactile switch 1632 (e.g., from ON to OFF or vice versa, from one functional state to another, etc.). The tactile switch 1632 may be aligned with an axis of the shaft 1630 and attached to the bracket 1616 using an adhesive 1634 (e.g., a conductive PSA).

In some embodiments, a gasket 1636 (e.g., an O-ring) may be positioned between the shaft 1630 and the through-hole. The shaft 1630 may have a circumferential groove 1638 in which a portion of the gasket 1636 is seated so that the gasket 1636 moves in a predictable way in response to movement of the shaft 1630. In some examples, the gasket 1636 may be non-conductive.

The button assembly 1600 may further include a set of electrical insulators (i.e., one or more electrical insulators), which set of electrical insulators may electrically insulate the button cap retention assembly 1614 from the housing 1604, and electrically insulate the conductive button cap 1612 from the housing 1604. For example, the button assembly 1600 may include a first electrical insulator, such as a sleeve 1640 (or set of shims), positioned between the conductive button cap 1612 and the sidewall 1608 (or set of sidewalls) of the cavity 1606 in the housing 1604. In some cases, the sleeve 1640 may include a closed-shape sidewall and an inward facing lip 1642 (FIG. 16B). In other cases, the sleeve 1640 may not include the inward facing lip 1642 or have a sidewall that does not define a closed shape. In other cases, the first electrical insulator may be a planar perimeter gasket (e.g., an insulator including the lip 1642 but not the sidewall). A second electrical insulator may include an adhesive 1644 (e.g., an adhesive ring) applied to a surface of the retainer 1618 facing the housing 1604, or to the outer surface of the ledge 1610 within the cavity 1606. In some cases, the adhesive 1644 may include a PSA. A gasket or seal 1646, external to the housing 1604, may be bonded to the adhesive 1644. The adhesive 1644 and seal 1646 may be compressed when the screws 1620 are tightened to clamp the housing 1604 between the bracket 1616 and retainer 1618 of the button cap retention assembly 1614. A third electrical insulator may include a spacer 1648, internal to the housing 1604, positioned between the bracket 1616 and the housing 1604. The third electrical insulator, in conjunction with the first and/or second electrical insulator, may electrically insulate the conductive button cap retention assembly 1614 (e.g., the bracket 1616 and the retainer 1618) from the housing 1604. The first electrical insulator may electrically insulate the conductive button cap 1612 from the housing 1604. In some embodiments, additional or different electrical insulators may electrically insulate the conductive button cap 1612 or button cap retention assembly 1614 from the housing 1604.

In use, a signal may be applied to, or received from, the button cap retention assembly 1614 (e.g., to/from the bracket 1616) via a circuit (e.g., a flex circuit or other circuit element 1650) that is electrically connected to the bracket 1616 (e.g., via a conductive adhesive 1652). A signal may travel through the conductive button cap 1612, coil springs 1628, retainer 1618, screws 1620, and bracket 1616 via a first electrical path, or through the conductive button cap 1612, retainer 1618, screws 1620, and bracket 1616 via a second electrical path. Although the second electrical path may be broken when the conductive button cap 1612 is pressed by a user, the conductive button cap 1612 may remain in electrical contact with the button cap retention assembly 1614 during all states of translation (e.g., via the first electrical path).

Figure 17A:
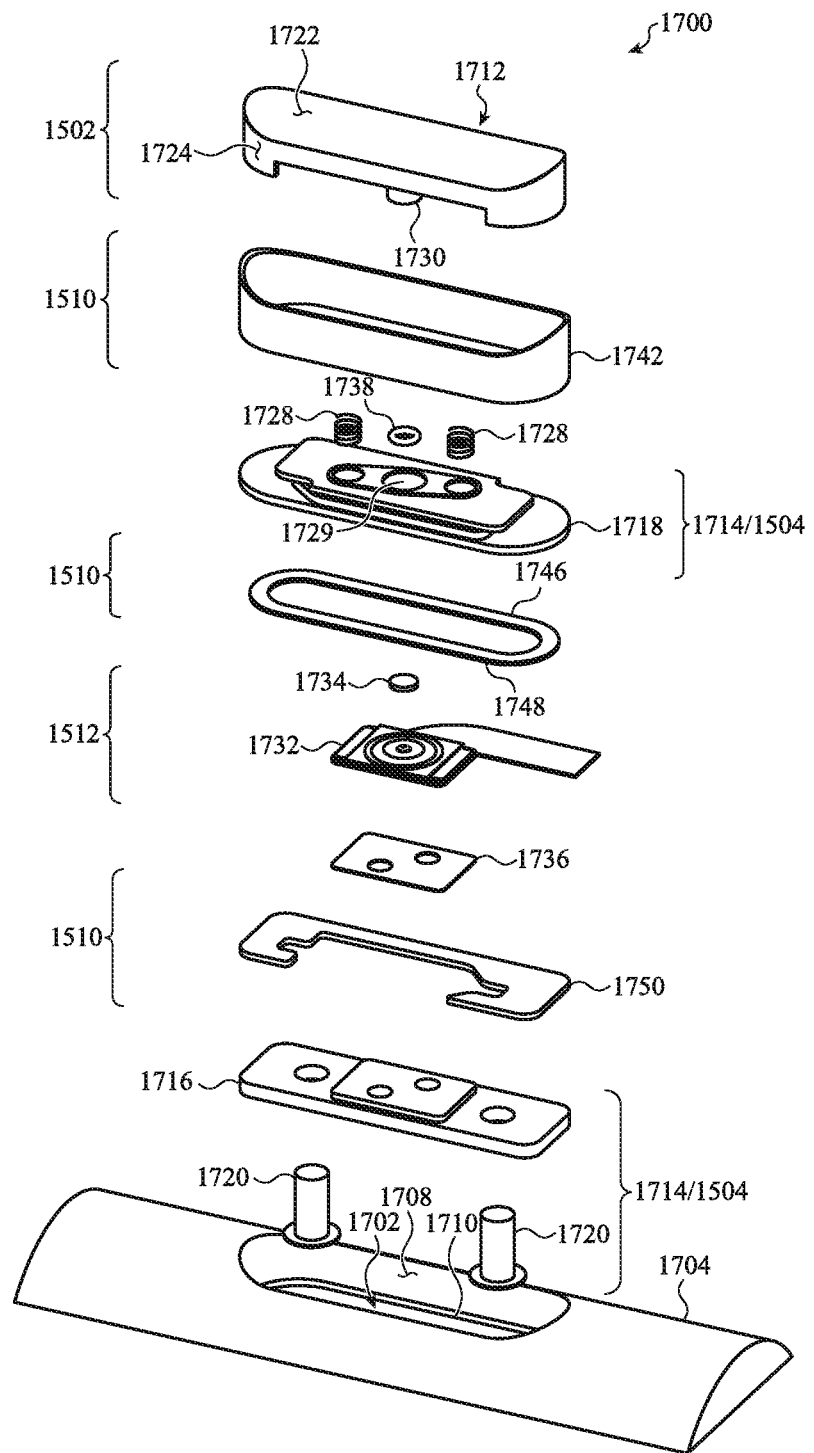
Figure 17B:
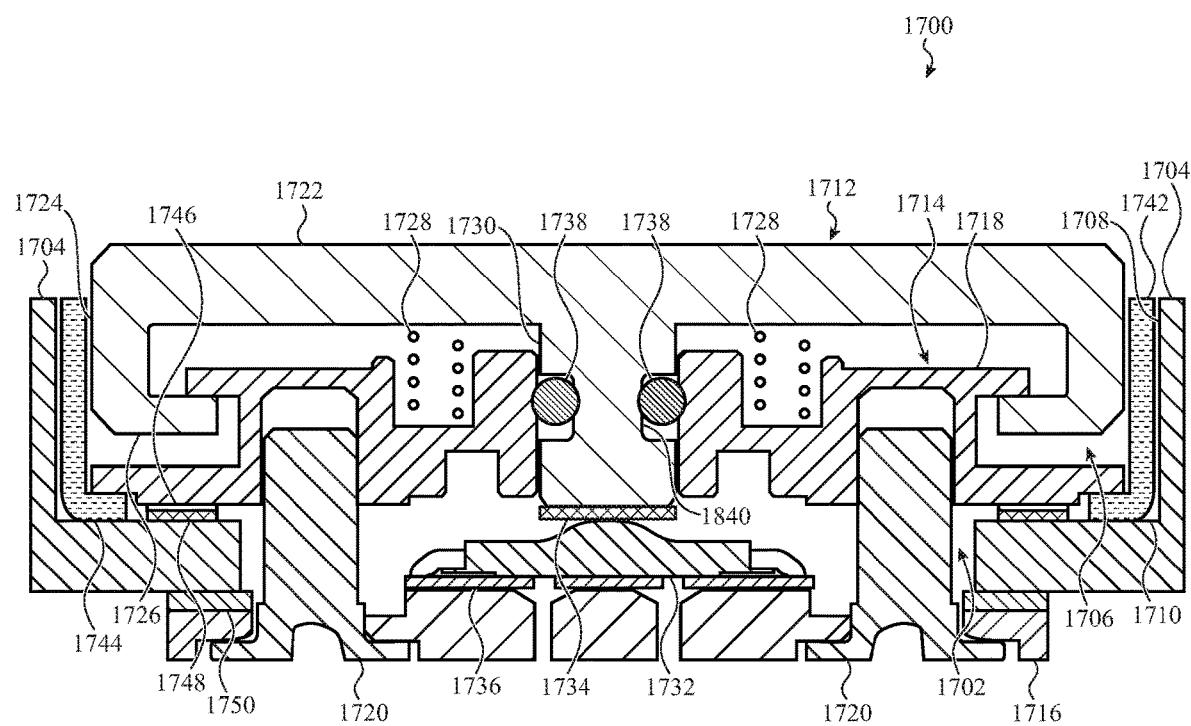

With reference to FIGS. 17A & 17B, there is shown another example of a button assembly 1700 that may be included in any of the electronic devices described with reference to FIG. 1A, 1B, 2A-2C, 3, 4A, or 4B. FIG. 17A shows an exploded view of the button assembly 1700, and FIG. 17B shows an assembled cross-section of the button assembly 1700, as viewed from the front or rear face of an electronic device such as the watch body 202 described with reference to FIGS. 2A-2C, 3, 4A, & 4B.

The button assembly 1700 is an example of the button assembly 1500 shown in FIG. 15, and includes components corresponding to the conductive button cap 1502, button cap retention assembly 1504, insulator 1510, and tactile switch 1512.

The button assembly 1700 may be at least partially within an opening 1702 in a housing 1704 (e.g., an opening in the housing described with reference to FIG. 2A, 2C, 3, 4A, or 4B), and may be attached to any the housing or an internal structure. In some cases, and as shown, the housing 1704 may include a cavity 1706 (FIG. 17B) defined by at least one sidewall (e.g., a single sidewall 1708 or set of sidewalls) and a ledge 1710. The ledge 1710 may define the opening 1702, and the sidewall 1708 may surround the ledge 1710.

The button assembly 1700 may include a conductive button cap 1712 (or button cap having a conductive portion). The conductive button cap 1712 may be retained by a button cap retention assembly 1714 (or button retainer), and may be translatable toward and away from the housing 1704. The button cap retention assembly 1714 may extend through the opening 1702 and be connected or otherwise attached to the housing 1704. In some examples, the button cap retention assembly 1714 may include a bracket 1716 that overlaps the ledge 1710 interior to the housing 1704, and a retainer 1718 that overlaps the ledge 1710 exterior to the housing 1704. The retainer 1718 may be mechanically attached to the bracket 1716 by a set of screws 1720 or other mechanical fastener. The screws 1720 may be inserted into through-holes in the bracket 1716 and screwed into threaded holes in the retainer 1718, clamping the ledge 1710 between the bracket 1716 and the retainer 1718.

The conductive button cap 1712 may have an exterior surface 1722, a sidewall or set of sidewalls 1724 parallel to the sidewall 1708 of the cavity 1706, and an inward facing lip or set of lips 1726 (FIG. 19) that extends between the retainer 1718 and the ledge 1710 and toward a center axis of the conductive button cap 1712. A set of one or more coil springs 1728 or other spring-biased members may be positioned between an outer surface of the retainer 1718 and an underside of the conductive button cap 1712, and may bias the conductive button cap 1712 in an outward state of translation.

The button cap retention assembly 1714, and in particular the retainer 1718, may have a through-hole 1729 defined therein, with an axis of the through-hole 1729 extending perpendicular to the opening 1702 in the housing 1704. A shaft 1730 may be positioned within the through-hole 1729, and may translate toward and away from the housing 1704. The shaft 1730 may be mechanically connected to the conductive button cap 1712, or may be biased to contact the conductive button cap 1712. In some cases, the shaft 1730 may be mechanically and electrically connected to the conductive button cap 1712. In a state of rest, the shaft 1730 and conductive button cap 1712 may be biased in an outward state of translation (i.e., away from the opening 1702) by the coil springs 1728 and/or a spring-biased tactile switch 1732. In some cases, a shim 1734, such as a non-conductive shim, may be attached to an end of the shaft 1730 facing the tactile switch 1732. When a user presses the conductive button cap 1712 toward the housing 1704, the press may overcome the bias provided by the coil springs 1728 and/or tactile switch 1732, and pressure on the conductive button cap 1712 may be transferred to the shaft 1730, which translates toward the housing 1704 and presses on the tactile switch 1732 to change the state of the tactile switch 1732 (e.g., from ON to OFF or vice versa, from one functional state to another, etc.). The tactile switch 1732 may be aligned with an axis of the shaft 1730 and attached to the bracket 1716 using an adhesive 1736 (e.g., a conductive PSA).

In some embodiments, a gasket 1738 (e.g., an O-ring) may be positioned between the shaft 1730 and the through-hole. The shaft 1730 may have a circumferential groove 1740 (FIG. 17B) in which a portion of the gasket 1738 is seated so that the gasket 1738 moves in a predictable way in response to movement of the shaft 1730. In some examples, the gasket 1738 may be conductive.

The button assembly 1700 may further include a set of electrical insulators (i.e., one or more electrical insulators), which set of electrical insulators may electrically insulate the button cap retention assembly 1714 from the housing 1704, and electrically insulate the conductive button cap 1712 from the housing 1704. For example, the button assembly 1700 may include a first electrical insulator, such as a sleeve 1742 (or set of shims), positioned between the conductive button cap 1712 and the sidewall 1708 (or set of sidewalls) of the cavity 1706 in the housing 1704. In some cases, the sleeve 1742 may include a closed-shape sidewall and an inward facing lip 1744 (FIG. 18B). In other cases, the sleeve 1742 may not include the inward facing lip 1744 or have a sidewall that does not define a closed shape. In other cases, the first electrical insulator may be a planar perimeter gasket (e.g., an insulator including the lip 1744 but not the sidewall). A second electrical insulator may include an adhesive 1746 (e.g., an adhesive ring) applied to a surface of the retainer 1718 facing the housing 1704, or to the outer surface of the ledge 1710 within the cavity 1706. In some cases, the adhesive 1746 may include a PSA. A gasket or seal 1748, external to the housing 1704, may be bonded to the adhesive 1746. The adhesive 1746 and seal 1748 may be compressed when the screws 1720 are tightened to clamp the housing 1704 between the bracket 1716 and retainer 1718 of the button cap retention assembly 1714. A third electrical insulator may include a spacer 1750, internal to the housing 1704, positioned between the bracket 1716 and the housing 1704. The third electrical insulator, in conjunction with the first and/or second electrical insulator, may electrically insulate the conductive button cap retention assembly 1714 (e.g., the bracket 1716 and the retainer 1718) from the housing 1704. The first electrical insulator may electrically insulate the conductive button cap 1712 from the housing 1704. In some embodiments, additional or different electrical insulators may electrically insulate the conductive button cap 1712 or button cap retention assembly 1714 from the housing 1704.

In use, a signal may be applied to, or received from, the button cap retention assembly 1714 (e.g., to/from the bracket 1716) via a circuit (e.g., a flex circuit or other circuit element) that is electrically connected to the bracket 1716 (e.g., as described with reference to FIG. 17A). A signal may travel through the conductive button cap 1712, shaft 1730, conductive gasket 1738, retainer 1718, screws 1720, and bracket 1716 via a first electrical path. The signal may also travel through the conductive button cap 1712, coil springs 1728, retainer 1718, screws 1720, and bracket 1716 via a second electrical path, or through the conductive button cap 1712, retainer 1718, screws 1720, and bracket 1716 via a third electrical path. Although the third electrical path may be broken when the conductive button cap 1712 is pressed by a user, the conductive button cap 1712 may remain in electrical contact with the button cap retention assembly 1714 during all states of translation (e.g., via the first and second electrical paths).

Figure 18A:
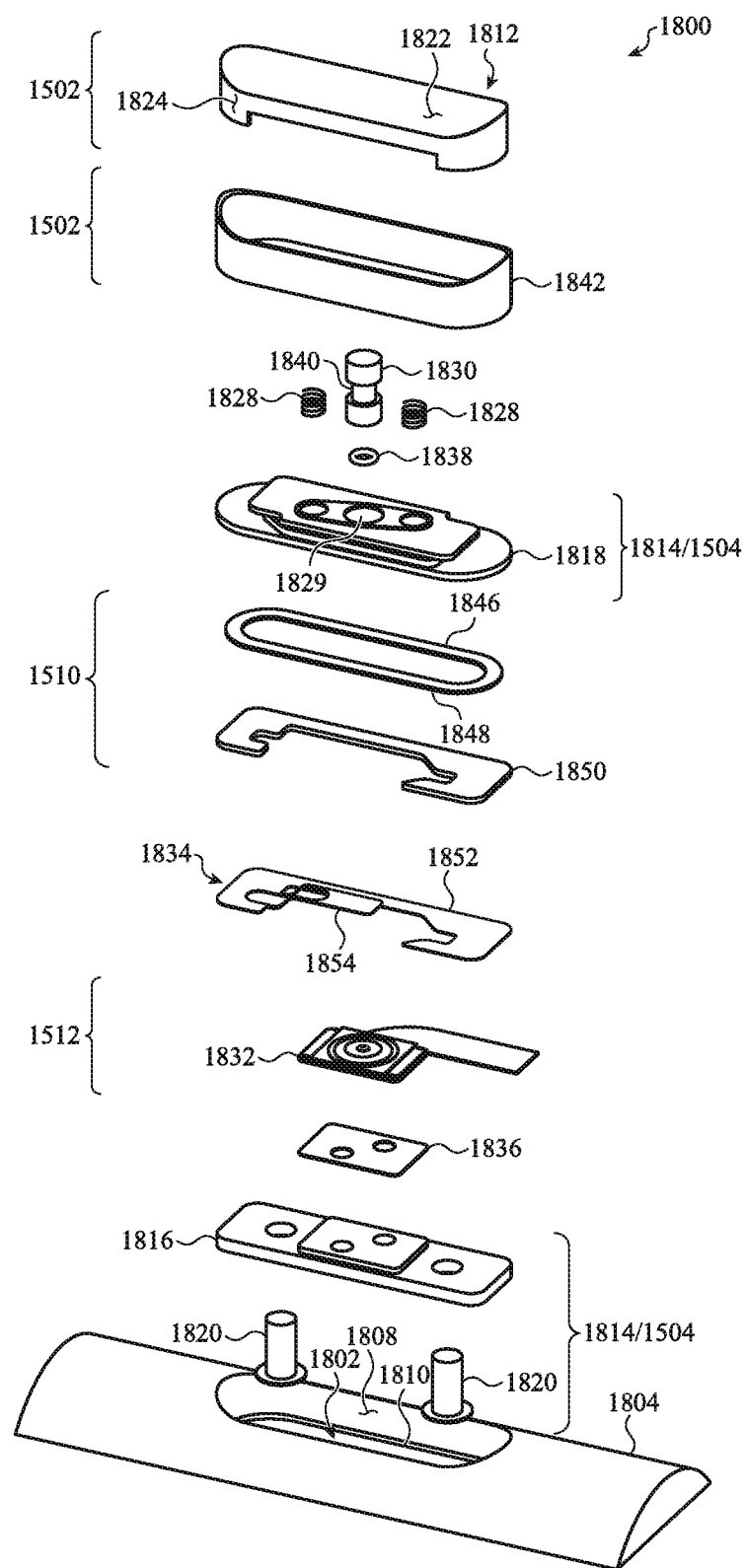
Figure 18B:
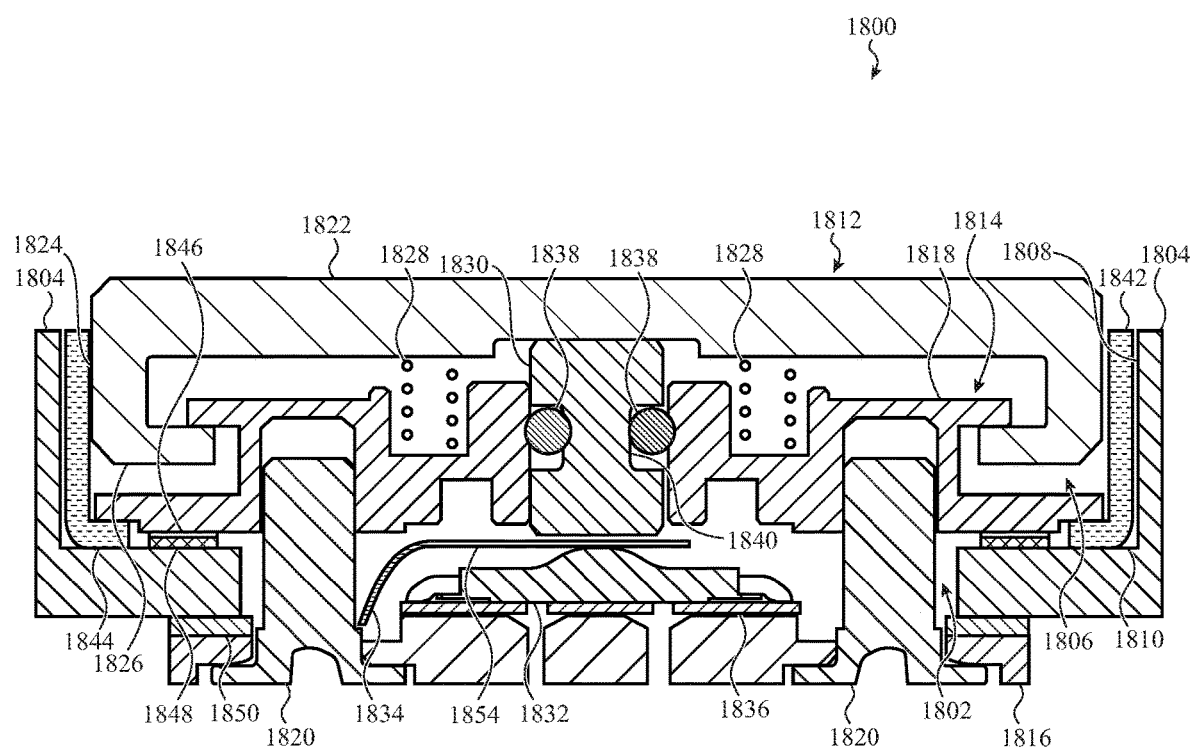

FIGS. 18A & 18B show another example of a button assembly 2000 that may be included in any of the electronic devices described with reference to FIG. 1A, 1B, 2A-2C, 3, 4A, or 4B. FIG. 18A shows an exploded view of the button assembly 1800, and FIG. 18B shows an assembled cross-section of the button assembly 1800, as viewed from the front or rear face of an electronic device such as the watch body 202 described with reference to FIGS. 2A-2C, 3, 4A, & 4B.

The button assembly 1800 is an example of the button assembly 1500 shown in FIG. 15, and includes components corresponding to the conductive button cap 1502, button cap retention assembly 1504, insulator 1510, and tactile switch 1512.

The button assembly 1800 may be at least partially within an opening 1802 in a housing 1804 (e.g., an opening in the housing described with reference to FIG. 2A, 2C, 3, 4A, or 4B), and may be attached to the housing or an internal structure such as a support. In some cases, and as shown, the housing 1804 may include a cavity 1806 (FIG. 18B) defined by at least one sidewall (e.g., a single sidewall 1808 or set of sidewalls) and a ledge 1810. The ledge 1810 may define the opening 1802, and the sidewall 1808 may surround the ledge 1810.

The button assembly 1800 may include a conductive button cap 1812 (or button cap having a conductive portion). The conductive button cap 1812 may be retained by a button cap retention assembly 1814 (or button retainer), and may be translatable toward and away from the housing 1804. The button cap retention assembly 1814 may extend through the opening 1802 and be connected or otherwise attached to the housing 1804. In some examples, the button cap retention assembly 1814 may include a bracket 1816 that overlaps the ledge 1810 interior to the housing 1804, and a retainer 1818 that overlaps the ledge 1810 exterior to the housing 1804. The retainer 1818 may be mechanically attached to the bracket 1816 by a set of screws 1820 or other mechanical fastener. The screws 1820 may be inserted into through-holes in the bracket 1816 and screwed into threaded holes in the retainer 1818, clamping the ledge 1810 between the bracket 1816 and the retainer 1818.

The conductive button cap 1812 may have an exterior surface 1822, a sidewall or set of sidewalls 1824 parallel to the sidewall 1808 of the cavity 1806, and an inward facing lip or set of lips 1826 (FIG. 18B) that extends between the retainer 1818 and the ledge 1810 and toward a center axis of the conductive button cap 1812. A set of one or more coil springs 1828 or other spring-biased members may be positioned between an outer surface of the retainer 1818 and an underside of the conductive button cap 1812, and may bias the conductive button cap 1812 in an outward state of translation.

The button cap retention assembly 1814, and in particular the retainer 1818, may have a through-hole 1829 defined therein, with an axis of the through-hole 1829 extending perpendicular to the opening 1802 in the housing 1804. A shaft 1830 may be positioned within the through-hole 1829, and may translate toward and away from the housing 1804. The shaft 1830 may be mechanically connected to the conductive button cap 1812, or may be biased to contact the conductive button cap 1812. In some cases, the shaft 1830 may be mechanically and electrically connected to the conductive button cap 1812. In a state of rest, the shaft 1830 and conductive button cap 1812 may be biased in an outward state of translation (i.e., away from the opening 1802) by the coil springs 1828 and/or a spring-biased tactile switch 1832. In some cases, a spring-biased conductor (e.g., a conductive shear plate 1834) may extend between the tactile switch 1832 and an end of the shaft 1830 facing the tactile switch 1832. When a user presses the conductive button cap 1812 toward the housing 1804, the press may overcome the bias provided by the coil springs 1828 and/or tactile switch 1832, and pressure on the conductive button cap 1812 may be transferred to the shaft 1830, which translates toward the housing 1804 and presses on the tactile switch 1832 to change the state of the tactile switch 1832 (e.g., from ON to OFF or vice versa, from one functional state to another, etc.). The tactile switch 1832 may be aligned with an axis of the shaft 1830 and attached to the bracket 1816 using an adhesive 1836 (e.g., a conductive PSA).

In some embodiments, a gasket 1838 (e.g., an O-ring) may be positioned between the shaft 1830 and the through-hole. The shaft 1830 may have a circumferential groove 1840 in which a portion of the gasket 1838 is seated so that the gasket 1838 moves in a predictable way in response to movement of the shaft 1830. In some examples, the gasket 1838 may be non-conductive.

The button assembly 1800 may further include a set of electrical insulators (i.e., one or more electrical insulators), which set of electrical insulators may electrically insulate the button cap retention assembly 1814 from the housing 1804, and electrically insulate the conductive button cap 1812 from the housing 1804. For example, the button assembly 1800 may include a first electrical insulator, such as a sleeve 1842 (or set of shims), positioned between the conductive button cap 1812 and the sidewall 1808 (or set of sidewalls) of the cavity 1806 in the housing 1804. In some cases, the sleeve 1842 may include a closed-shape sidewall and an inward facing lip 1844 (FIG. 18B). In other cases, the sleeve 1842 may not include the inward facing lip 1844 or have a sidewall that does not define a closed shape. In other cases, the first electrical insulator may be a planar perimeter gasket (e.g., an insulator including the lip 1844 but not the sidewall). A second electrical insulator may include an adhesive 1846 (e.g., an adhesive ring) applied to a surface of the retainer 1818 facing the housing 1804, or to the outer surface of the ledge 1810 within the cavity 1806. In some cases, the adhesive 1846 may include a PSA. A gasket or seal 1848, external to the housing 1804, may be bonded to the adhesive 1846. The adhesive 1846 and seal 1848 may be compressed when the screws 1820 are tightened to clamp the housing 1804 between the bracket 1816 and retainer 1818 of the button cap retention assembly 1814. A third electrical insulator may include a spacer 1850, internal to the housing 1804, positioned between the bracket 1816 and the housing 1804. The third electrical insulator, in conjunction with the first and/or second electrical insulator, may electrically insulate the conductive button cap retention assembly 1814 (e.g., the bracket 1816 and the retainer 1818) from the housing 1804. The first electrical insulator may electrically insulate the conductive button cap 1812 from the housing 1804. In some embodiments, additional or different electrical insulators may electrically insulate the conductive button cap 1812 or button cap retention assembly 1814 from the housing 1804.

The shear plate 1834 may be formed from a conductive sheet that is stamped, molded, or otherwise shaped to form an open (shown) or closed (not shown) shape conductive perimeter 1852 and an elevated tab 1854 (e.g., a tab having an end positioned in a different plane than the conductive perimeter 1852). The conductive perimeter 1852 may be positioned between the bracket 1816 and spacer 1850, such that the conductive perimeter 1852 and shear plate 1834 are electrically insulated from the housing 1804. The shear plate 1834 deforms in response to translation of the shaft 1830.

In use, a signal may be applied to, or received from, the button cap retention assembly 1814 (e.g., to/from the bracket 1816) via a circuit (e.g., a flex circuit or other circuit element) that is electrically connected to the bracket 1816 (e.g., as described with reference to FIG. 16B). A signal may travel through the conductive button cap 1812, shaft 1830, shear plate 1834, and bracket 1816 via a first electrical path. The signal may also travel through the conductive button cap 1812, coil springs 1828, retainer 1818, screws 1820, and bracket 1816 via a second electrical path, or through the conductive button cap 1812, retainer 1818, screws 1820, and bracket 1816 via a third electrical path. Although the third electrical path may be broken when the conductive button cap 1812 is pressed by a user, the conductive button cap 1812 may remain in electrical contact with the button cap retention assembly 1814 during all states of translation (e.g., via the first and second electrical paths).

Figure 19:
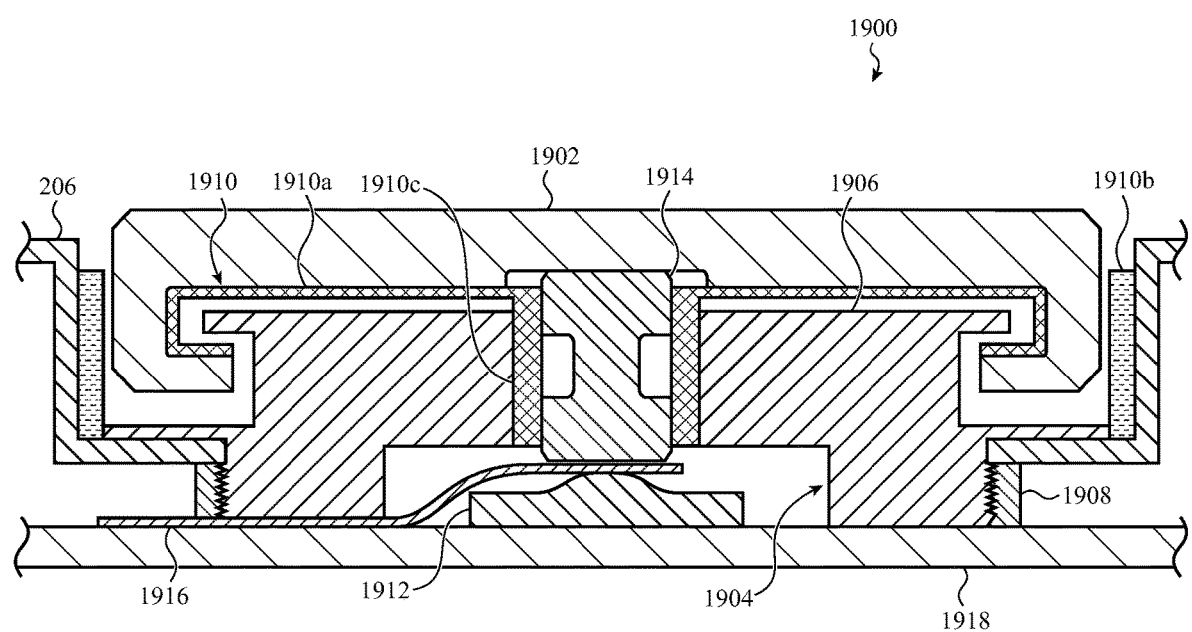

FIG. 19 shows an example elevation of a button assembly 1900. The button assembly 1900 may be an example of a button assembly included in any of the electronic devices described with reference to FIG. 1A, 1B, 2A-2C, 3, 4A, or 4B.

The button assembly 1900 may include a conductive button cap 1902. The conductive button cap 1902 may be retained within an opening in a housing by a button cap retention assembly 1904 (e.g., a button retainer). The button cap retention assembly 1904, or parts thereof, may be conductive. By way of example, the housing is shown to be the housing 206 of the watch body 202 described with reference to FIGS. 2A-2C, 3, 4A, & 4B. The button cap retention assembly 1904 may be attached to the housing 206 and extend through the opening in the housing 206. In some embodiments, the button cap retention assembly 1904 may include a first component 1906 that is inserted through the opening from one side of the housing 206, and a second component 1908 that fastens to the first component 1906 on the other side of the housing 206 (e.g., by threads, screws, solder, or an adhesive).

A set of one or more insulators 1910 (e.g., electrical insulators) may electrically insulate the conductive button cap 1902 from the button cap retention assembly 1904. The insulator 1910 may also electrically insulate the conductive button cap 1902 from the housing 206. Although the insulator 1910 is generally shown in FIG. 19 to include a non-conductive liner 1910a on an underside of the conductive button cap 1902, a non-conductive sleeve 1910b positioned between the conductive button cap 1902 and the housing 206, and a non-conductive sleeve 1910c positioned between the button cap retention assembly 1904 and a shaft 1914, the insulator 1910 may alternatively include more or fewer elements, which elements may be positioned in different locations within the button assembly 1900, as described with reference to FIGS. 20, 21, & 22.

The conductive button cap 1902 may translate toward and away from the housing 206, and may be insulated from the button cap retention assembly 1904 during all phases of translation. When the conductive button cap 1902 is pressed by a user and translates toward the housing 206, a tactile switch 1912 may be actuated (e.g., switched between two or more states). The shaft 1914 may extend between an interior surface of the conductive button cap 1902 and a depressible surface of the tactile switch 1912. The tactile switch 1912 and shaft 1914, or other elements not shown in FIG. 19 (e.g., springs), may bias the conductive button cap 1902 in an outwardly translated position.

The conductive button cap 1902 may function as an electrode, and an electrical signal may be routed between the conductive button cap 1902 and a circuit 1916, at least in part, via the shaft 1914. In some embodiments, the button cap retention assembly 1904, tactile switch 1912, and circuit 1916 may be attached to a common substrate 1918.

Because the signals received by or propagated from the conductive button cap 1902 may be low voltage or low amplitude signals, the materials, positions, electrical connections to, and electrical routing paths for an electrode formed on or by the conductive button cap 1902 can have a significant impact on the ability of the circuit 1916 to discern useful signals representing an ECG or other biological parameter of a person wearing an electronic device including the button assembly 1900. The materials, positions, electrical connections to, and electrical routing paths for the button assembly 1900 can also determine how well the button assembly 1900 receives voltages/signals from a person's skin (e.g., a SNR of a device-to-user interface through which the voltages/signals pass); how well voltages/signals are transferred between the conductive button cap 1902 and internal components of an electronic device (e.g., a voltage/signal propagation SNR); and how well the button assembly 1900 operates in the face of environmental factors, such as temperature, humidity, moisture, electromagnetic radiation, dust, and so on. In some cases, the insulator 1910 may be positioned to prevent moisture from electrically shorting the conductive button cap 1902 to the housing 206, or the housing 206 may be grounded to provide electrical shielding for some or all of the signals propagated through the button assembly 1900.

Figure 20:
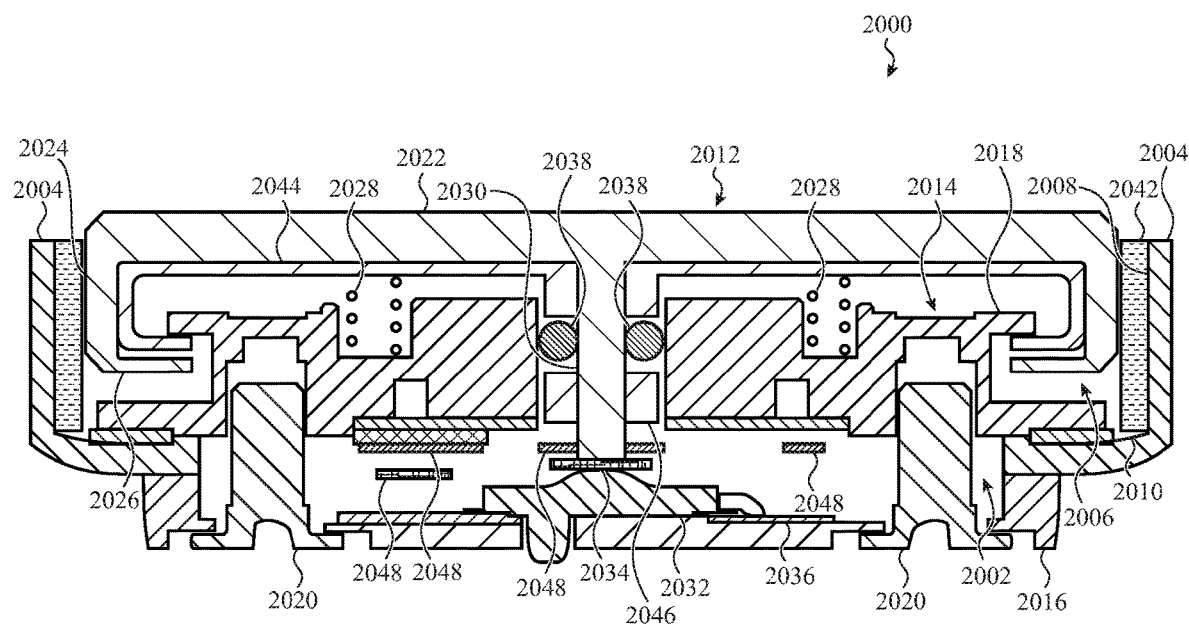
Figure 21:
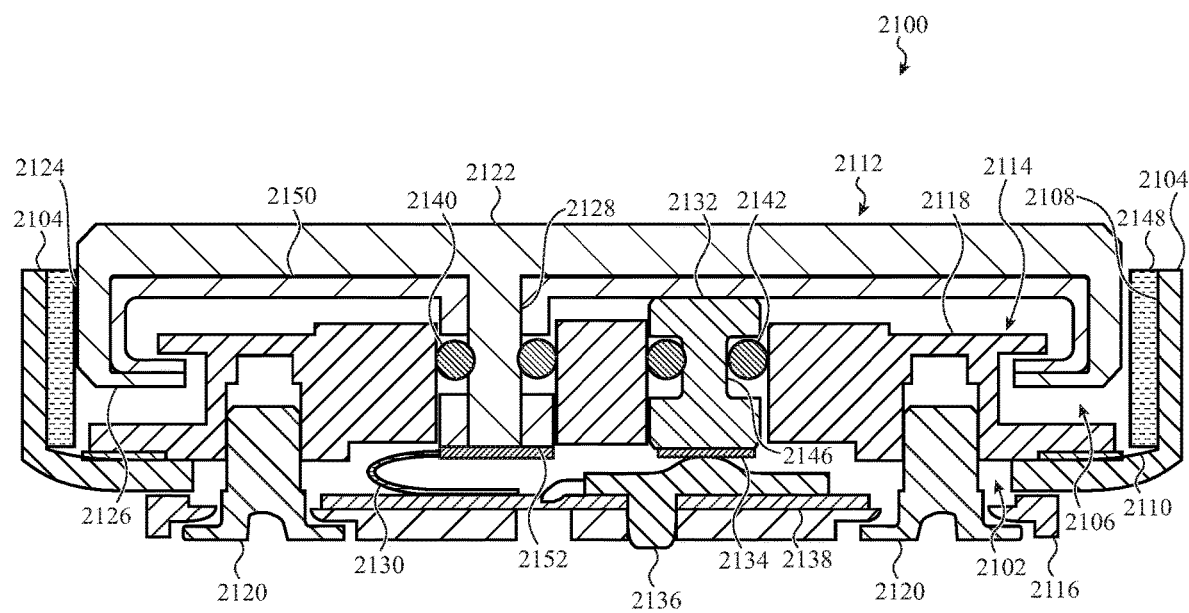
Figure 22:
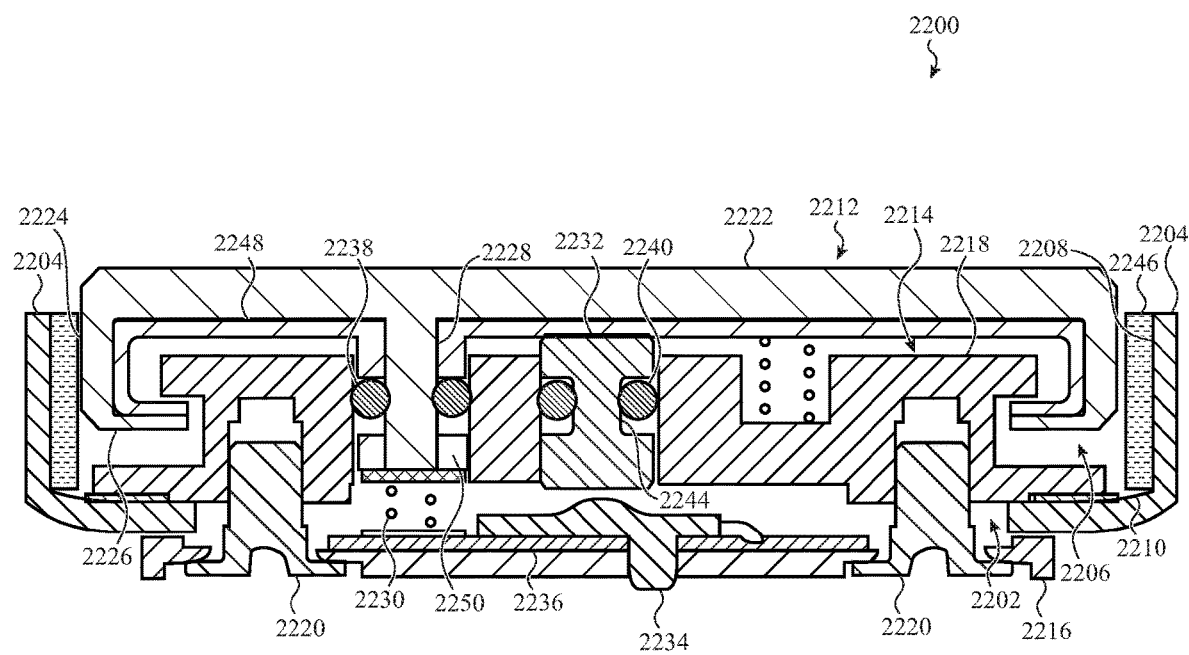

More detailed examples of the button assembly 1900 described with reference to FIG. 19 are shown in FIGS. 20, 21, & 22.

Referring now to FIG. 20, there is shown an assembled cross-section of another example of a button assembly 2000 that may be included in any of the electronic devices described with reference to FIG. 1A, 1B, 2A-2C, 3, 4A, or 4B. The button assembly 2000 may be at least partially within an opening 2002 in a housing 2004 (e.g., an opening in the housing described with reference to FIG. 2A, 2C, 3, 4A, or 4B), and may be attached to the housing or an internal structure such as a support. In some cases, and as shown, the housing 2004 may include a cavity 2006 defined by at least one sidewall (e.g., a single sidewall 2008 or set of sidewalls) and a ledge 2010. The ledge 2010 may define the opening 2002, and the sidewall 2008 may surround the ledge 2010.

The button assembly 2000 may include a conductive button cap 2012 (or button cap having a conductive portion). The conductive button cap 2012 may be retained by a button cap retention assembly 2014 (or button retainer), and may be translatable toward and away from the housing 2004. The button cap retention assembly 2014 may extend through the opening 2002 and be connected or otherwise attached to the housing 2004. In some examples, the button cap retention assembly 2014 may include a bracket 2016 that overlaps the ledge 2010 interior to the housing 2004, and a retainer 2018 that overlaps the ledge 2010 exterior to the housing 2004. The retainer 2018 may be mechanically attached to the bracket 2016 by a set of screws 2020 or other mechanical fastener. The screws 2020 may be inserted into through-holes in the bracket 2016 and screwed into threaded holes in the retainer 2018, clamping the ledge 2010 between the bracket 2016 and the retainer 2018.

The conductive button cap 2012 may have an exterior surface 2022, a sidewall or set of sidewalls 2024 parallel to the sidewall 2008 of the cavity 2006, and an inward facing lip or set of lips 2026 that extends between the retainer 2018 and the ledge 2010 and toward a center axis of the conductive button cap 2012. A set of one or more coil springs 2028 or other spring-biased members may be positioned between an outer surface of the retainer 2018 and an underside of the conductive button cap 2012, and may bias the conductive button cap 2012 in an outward state of translation.

The button cap retention assembly 2014, and in particular the retainer 2018, may have a through-hole defined therein, with an axis of the through-hole extending perpendicular to the opening 2002 in the housing 2004. A shaft 2030 may be positioned within the through-hole, and may translate toward and away from the housing 2004. The shaft 2030 may be mechanically and electrically connected to the conductive button cap 2012, or may be biased to contact the conductive button cap 2012. In a state of rest, the shaft 2030 and conductive button cap 2012 may be biased in an outward state of translation (i.e., away from the opening 2002) by the coil springs 2028 and/or a spring-biased tactile switch 2032. In some cases, a shim 2034, such as a non-conductive shim, may be attached to an end of the shaft 2030 facing the tactile switch 2032. When a user presses the conductive button cap 2012 toward the housing 2004, the press may overcome the bias provided by the coil springs 2028 and/or tactile switch 2032, and pressure on the conductive button cap 2012 may be transferred to the shaft 2030, which translates toward the housing 2004 and presses on the tactile switch 2032 to change the state of the tactile switch 2032 (e.g., from ON to OFF or vice versa, from one functional state to another, etc.). The tactile switch 2032 may be aligned with an axis of the shaft 2030 and attached to the bracket 2016 using an adhesive 2036 (e.g., a non-conductive PSA).

In some embodiments, a gasket 2038 (e.g., an O-ring) may be positioned between the shaft 2030 and the through-hole. In some cases, the gasket 2038 may be positioned between a first non-conductive liner 2044 and a second non-conductive liner 2046. In some examples, the gasket 2038 may be non-conductive.

The button assembly 2000 may further include a set of electrical insulators (i.e., one or more electrical insulators), which set of electrical insulators may electrically insulate the conductive button cap 2012 from the button cap retention assembly 2014 and housing 2004. For example, the button assembly 2000 may include a first electrical insulator, such as a sleeve 2042 (or set of shims), positioned between the conductive button cap 2012 and the sidewall 2008 (or set of sidewalls) of the cavity 2006 in the housing 2004. In some cases, the sleeve 2042 may include a closed-shape sidewall. In other cases, the sleeve 2042 may also include an inward facing lip, or may not have a sidewall that defines a closed shape. A second electrical insulator may include a non-conductive liner 2044 between an interior surface of the conductive button cap 2012 and the button cap retention assembly 2014. In some cases, the non-conductive liner 2044 may be press-fit or adhesively bonded to the interior surface of the conductive button cap 2012. Alternatively, the non-conductive liner 2044 may be press-fit or adhesively bonded to an exterior surface of the retainer 2018. In some embodiments, the non-conductive liner 2044 may extend into the through-hole, between the shaft 2030 and the button cap retention assembly 2014 (e.g., between the shaft 2030 and the retainer 2018). A third electrical insulator may include a second non-conductive liner 2046, positioned in the through-hole between the shaft 2030 and the retainer 2018, below the gasket 2038. The second electrical insulator, in some cases in conjunction with the third electrical insulator, may electrically insulate the conductive button cap 2012 from the button cap retention assembly 2014 (e.g., from the retainer 2018). The first electrical insulator may electrically insulate the conductive button cap 2012 from the housing 2004. In some embodiments, additional or different electrical insulators may electrically insulate the conductive button cap 2012 from the button cap retention assembly 2014 or housing 2004.

A conductive flexure 2048 may be coupled to, but insulated from, the bracket 2016, and positioned (e.g., angled) to contact the end of the shaft 2030 that faces the tactile switch 2032. The conductive flexure 2048 may be spring-biased to contact the end of the shaft 2030, and may be spring-biased to remain in contact with the end of the shaft 2030 during all states of translation of the shaft 2030.

In use, a signal may be applied to, or received from, the conductive button cap 2012 via a circuit (e.g., a flex circuit or other circuit element) that is electrically connected to the conductive flexure 2048. A signal may travel through the conductive button cap 2012, shaft 2030, and conductive flexure 2048.

FIG. 21 shows an assembled cross-section of another example of a button assembly 2100 that may be included in any of the electronic devices described with reference to FIG. 1A, 1B, 2A-2C, 3, 4A, or 4B. The button assembly 2100 may be at least partially within an opening 2102 in a housing 2104 (e.g., an opening in the housing described with reference to FIG. 2A, 2C, 3, 4A, or 4B), and may be attached to the housing or an internal structure such as a support. In some cases, and as shown, the housing 2104 may include a cavity 2106 defined by at least one sidewall (e.g., a single sidewall 2108 or set of sidewalls) and a ledge 2110. The ledge 2110 may define the opening 2102, and the sidewall 2108 may surround the ledge 2110.

The button assembly 2100 may include a conductive button cap 2112 (or button cap having a conduction portion). The conductive button cap 2112 may be retained by a button cap retention assembly 2114 (or button retainer), and may be translatable toward and away from the housing 2104. The button cap retention assembly 2114 may extend through the opening 2102 and be connected or otherwise attached to the housing 2104. In some examples, the button cap retention assembly 2114 may include a bracket 2116 that overlaps the ledge 2110 interior to the housing 2104, and a retainer 2118 that overlaps the ledge 2110 exterior to the housing 2104. The retainer 2118 may be mechanically attached to the bracket 2116 by a set of screws 2120 or other mechanical fastener. The screws 2120 may be inserted into through-holes in the bracket 2116 and screwed into threaded holes in the retainer 2118, clamping the ledge 2110 between the bracket 2116 and the retainer 2118.

The conductive button cap 2112 may have an exterior surface 2122, a sidewall or set of sidewalls 2124 parallel to the sidewall 2108 of the cavity 2106, and an inward facing lip or set of lips 2126 that extends between the retainer 2118 and the ledge 2110 and toward a center axis of the conductive button cap 2112.

The button cap retention assembly 2114, and in particular the retainer 2118, may have a through-hole defined therein, with an axis of the through-hole extending perpendicular to the opening 2102 in the housing 2104. A shaft 2128 may be positioned within the through-hole, and may translate toward and away from the housing 2104. The shaft 2128 may be mechanically and electrically connected to the conductive button cap 2112, or may be biased to contact the conductive button cap 2112. In a state of rest, the shaft 2128 and conductive button cap 2112 may be biased in an outward state of translation (i.e., away from the opening 2102) by a conductive flexure 2130 or other spring-biased member positioned between the bracket 2116 and an end of the shaft 2128 that faces the bracket 2116.

The button cap retention assembly 2114, and in particular the retainer 2118, may also have a second through-hole formed therein, with an axis of the second through-hole extending perpendicular to the opening 2102 in the housing 2104. A piston 2132 may be positioned within the through-hole, and may translate toward and away from the housing 2104. In some cases, a shim 2134, such as a non-conductive shim, may be attached to an end of the piston 2132 facing a spring-biased tactile switch 2136. When a user presses the conductive button cap 2112 toward the housing 2104, the press may overcome the bias provided by the conductive flexure 2130 and/or tactile switch 2136, and pressure on the conductive button cap 2112 may be transferred to the piston 2132, which translates toward the housing 2104 and presses on the tactile switch 2136 to change the state of the tactile switch 2136 (e.g., from ON to OFF or vice versa, from one functional state to another, etc.). The tactile switch 2136 may be aligned with an axis of the piston 2132 and attached to the bracket 2116 using an adhesive 2138 (e.g., a non-conductive PSA).

In some embodiments, a first gasket 2140 (e.g., an O-ring) may be positioned between the shaft 2128 and the first through-hole, and a second gasket 2142 (e.g., an O-ring) may be positioned between the piston 2132 and the second through-hole. In some cases, the first gasket 2140 may be positioned between a first non-conductive liner 2150 and a second non-conductive liner 2152. In some cases, the piston 2132 may have a circumferential groove 2146 in which a portion of the second gasket 2142 is seated so that the second gasket 2142 moves in a predictable way in response to movement of the piston 2132. In some examples, the first and second gaskets 2140, 2142 may be non-conductive.

The button assembly 2100 may further include a set of electrical insulators (i.e., one or more electrical insulators), which set of electrical insulators may electrically insulate the conductive button cap 2112 from the button cap retention assembly 2114 and housing 2104. For example, the button assembly 2100 may include a first electrical insulator, such as a sleeve 2148 (or set of shims), positioned between the conductive button cap 2112 and the sidewall 2108 (or set of sidewalls) of the cavity 2106 in the housing 2104. In some cases, the sleeve 2148 may include a closed-shape sidewall. In other cases, the sleeve 2148 may also include an inward facing lip, or may not have a sidewall that defines a closed shape. A second electrical insulator may include a non-conductive liner 2150 between an interior surface of the conductive button cap 2112 and the button cap retention assembly 2114. In some cases, the non-conductive liner 2150 may be press-fit or adhesively bonded to the interior surface of the conductive button cap 2112. Alternatively, the non-conductive liner 2150 may be press-fit or adhesively bonded to an exterior surface of the retainer 2118. In some embodiments, the non-conductive liner 2150 may extend into the through-hole, between the shaft 2128 and the button cap retention assembly 2114 (e.g., between the shaft 2128 and the retainer 2118). A third electrical insulator may include a second non-conductive liner 2152, positioned in the through-hole between the shaft 2128 and the retainer 2118, below the gasket 2140. The second electrical insulator, in some cases in conjunction with the third electrical insulator, may electrically insulate the conductive button cap 2112 from the button cap retention assembly 2114 (e.g., from the retainer 2118). The first electrical insulator may electrically insulate the conductive button cap 2112 from the housing 2104. In some embodiments, additional or different electrical insulators may electrically insulate the conductive button cap 2112 from the button cap retention assembly 2114 or housing 2104.

In use, a signal may be applied to, or received from, the conductive button cap 2112 via a circuit (e.g., a flex circuit or other circuit element) that is electrically connected to the conductive flexure 2130. A signal may travel through the conductive button cap 2112, shaft 2128, and conductive flexure 2130.

FIG. 22 shows an assembled cross-section of another example of a button assembly 2200 that may be included in any of the electronic devices described with reference to FIG. 1A, 1B, 2A-2C, 3, 4A, or 4B. The button assembly 2200 may be at least partially within an opening 2202 in a housing 2204 (e.g., an opening in the housing described with reference to FIG. 2A, 2C, 3, 4A, or 4B), and may be attached to the housing or an internal structure such as a support. In some cases, and as shown, the housing 2204 may include a cavity 2206 defined by at least one sidewall (e.g., a single sidewall 2208 or set of sidewalls) and a ledge 2210. The ledge 2210 may define the opening 2202, and the sidewall 2208 may surround the ledge 2210.

The button assembly 2200 may include a conductive button cap 2212 (or button cap having a conductive portion). The conductive button cap 2212 may be retained by a button cap retention assembly 2214 (or button retainer), and may be translatable toward and away from the housing 2204. The button cap retention assembly 2214 may extend through the opening 2202 and be connected or otherwise attached to the housing 2204. In some examples, the button cap retention assembly 2214 may include a bracket 2216 that overlaps the ledge 2210 interior to the housing 2204, and a retainer 2218 that overlaps the ledge 2210 exterior to the housing 2204. The retainer 2218 may be mechanically attached to the bracket 2216 by a set of screws 2220 or other mechanical fastener. The screws 2220 may be inserted into through-holes in the bracket 2216 and screwed into threaded holes in the retainer 2218, clamping the ledge 2210 between the bracket 2216 and the retainer 2218.

The conductive button cap 2212 may have an exterior surface 2222, a sidewall or set of sidewalls 2224 parallel to the sidewall 2208 of the cavity 2206, and an inward facing lip or set of lips 2226 that extends between the retainer 2218 and the ledge 2210 and toward a center axis of the conductive button cap 2212.

The button cap retention assembly 2214, and in particular the retainer 2218, may have a through-hole defined therein, with an axis of the through-hole extending perpendicular to the opening 2202 in the housing 2204. A shaft 2228 may be positioned within the through-hole, and may translate toward and away from the housing 2204. The shaft 2228 may be mechanically and electrically connected to the conductive button cap 2212, or may be biased to contact the conductive button cap 2212. In a state of rest, the shaft 2228 and conductive button cap 2212 may be biased in an outward state of translation (i.e., away from the opening 2202) by a conductive spring (e.g., a coil spring 2230) or other spring-biased member positioned between the bracket 2216 and an end of the shaft 2228 that faces the bracket 2216.

The button cap retention assembly 2214, and in particular the retainer 2218, may also have a second through-hole formed therein, with an axis of the second through-hole extending perpendicular to the opening 2202 in the housing 2204. A piston 2232 may be positioned within the through-hole, and may translate toward and away from the housing 2204. When a user presses the conductive button cap 2212 toward the housing 2204, the press may overcome the bias provided by the coil spring 2230 and/or tactile switch 2234, and pressure on the conductive button cap 2212 may be transferred to the piston 2232, which translates toward the housing 2204 and presses on the tactile switch 2234 to change the state of the tactile switch 2234 (e.g., from ON to OFF or vice versa, from one functional state to another, etc.). The tactile switch 2234 may be aligned with an axis of the piston 2232 and attached to the bracket 2216 using an adhesive 2236 (e.g., a non-conductive PSA).

In some embodiments, a first gasket 2238 (e.g., an O-ring) may be positioned between the shaft 2228 and the first through-hole, and a second gasket 2240 (e.g., an O-ring) may be positioned between the piston 2232 and the second through-hole. In some cases, the first gasket 2238 may be positioned between a first non-conductive liner 2248 and a second non-conductive liner 2250. In some cases, the piston 2232 may have a circumferential groove 2244 in which a portion of the second gasket 2240 is seated so that the second gasket 2240 moves in a predictable way in response to movement of the piston 2232. In some examples, the first and second gaskets 2238, 2240 may be non-conductive.

The button assembly 2200 may further include a set of electrical insulators (i.e., one or more electrical insulators), which set of electrical insulators may electrically insulate the conductive button cap 2212 from the button cap retention assembly 2214 and housing 2204. For example, the button assembly 2200 may include a first electrical insulator, such as a sleeve 2246 (or set of shims), positioned between the conductive button cap 2212 and the sidewall 2208 (or set of sidewalls) of the cavity 2206 in the housing 2204. In some cases, the sleeve 2246 may include a closed-shape sidewall. In other cases, the sleeve 2246 may also include an inward facing lip, or may not have a sidewall that defines a closed shape. A second electrical insulator may include a non-conductive liner 2248 between an interior surface of the conductive button cap 2212 and the button cap retention assembly 2214. In some cases, the non-conductive liner 2248 may be press-fit or adhesively bonded to the interior surface of the conductive button cap 2212. Alternatively, the non-conductive liner 2248 may be press-fit or adhesively bonded to an exterior surface of the retainer 2218. In some embodiments, the non-conductive liner 2248 may extend into the through-hole, between the shaft 2228 and the button cap retention assembly 2214 (e.g., between the shaft 2228 and the retainer 2218). A third electrical insulator may include a second non-conductive liner 2250, positioned in the through-hole between the shaft 2228 and the retainer 2218, below the gasket 2238. The second electrical insulator, in some cases in conjunction with the third electrical insulator, may electrically insulate the conductive button cap 2212 from the button cap retention assembly 2214 (e.g., from the retainer 2218). The first electrical insulator may electrically insulate the conductive button cap 2212 from the housing 2204. In some embodiments, additional or different electrical insulators may electrically insulate the conductive button cap 2212 from the button cap retention assembly 2214 or housing 2204.

In use, a signal may be applied to, or received from, the conductive button cap 2212 via a circuit (e.g., a flex circuit or other circuit element) that is electrically connected to the coil spring 2230. A signal may travel through the conductive button cap 2212, shaft 2228, and coil spring 2230.

Figure 23:
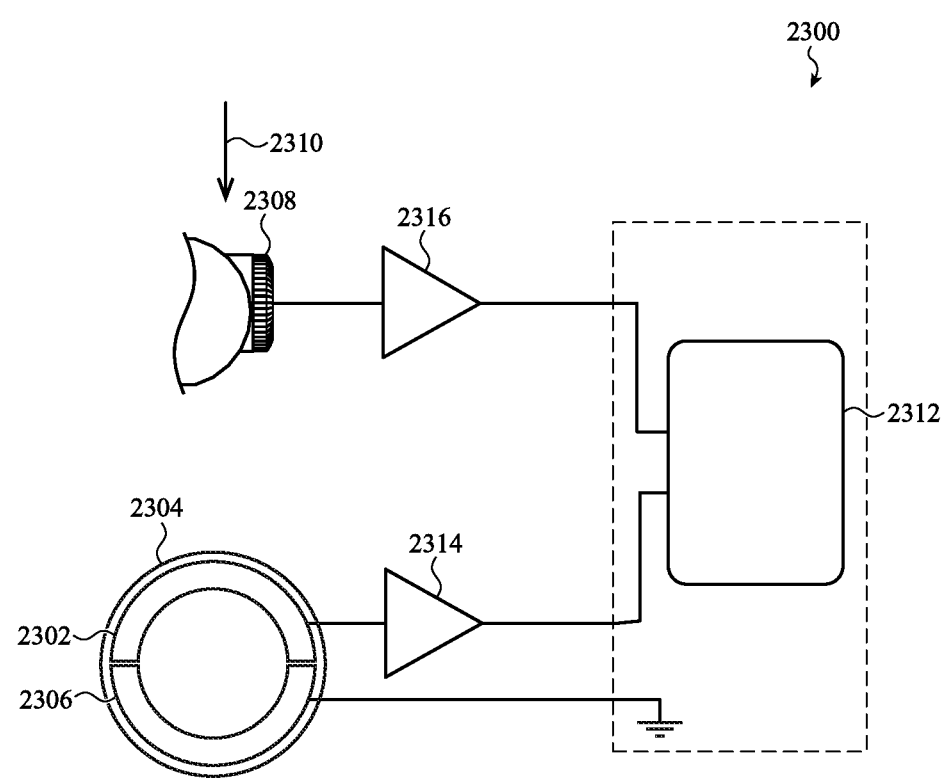
FIG. 23 shows a schematic of an electronic device that may be used for acquiring an ECG or other biological parameter from a user of the electronic device.

FIG. 23 shows a schematic 2300 of an electronic device, such as an electronic watch, that may be used for acquiring an ECG or other biological parameter from a user of the electronic device. In some cases, the electronic device may include a watch body. As shown, the electronic device may include a first electrode 2302 on a carrier 2304, an optional second electrode 2306 on the carrier 2304, and a third electrode 2308 on the surface of a user-rotatable crown 2310 (or alternatively, on the surface of a button). The third electrode 2308 may be operable to be contacted by a finger of a user while the first electrode 2302 (and optional second electrode 2306) are positioned against a user's skin (e.g., against the wrist of the user). A processor 2312, which in some cases may be provided in an integrated circuit (IC), an application-specific integrated circuit (ASIC), a field programmable gate array (FPGA), a system in package (SIP), a system on a chip (SOC), etc., may be operable to acquire an ECG from the user, or determine another biological parameter of, the user. The ECG or other biological parameter may be determined based on voltages at the first, optional second, and third electrodes 2302, 2306, 2308 while the user is in contact with the first, optional second, and third electrodes 2302, 2306, 2308.

In some cases, voltages may be sensed at just the first and third electrodes 2302, 2308. In other cases, the second electrode 2306 may be grounded to the electronic device, thereby coupling the user to the electronic device, and the voltage at the second electrode 2306 (i.e., the ground voltage) may be used to remove noise generated by the electronic device or other environmental sources from the signals measured at the first and third electrodes 2302, 2308. This may result in more accurate readings (or processing) of the first and third voltages.

As shown, a signal or voltages at the first electrode 2302 may be amplified by a first amplifier 2314, and a signal or voltages at the third electrode 2308 may be amplified by a second amplifier 2316.

Figure 24:
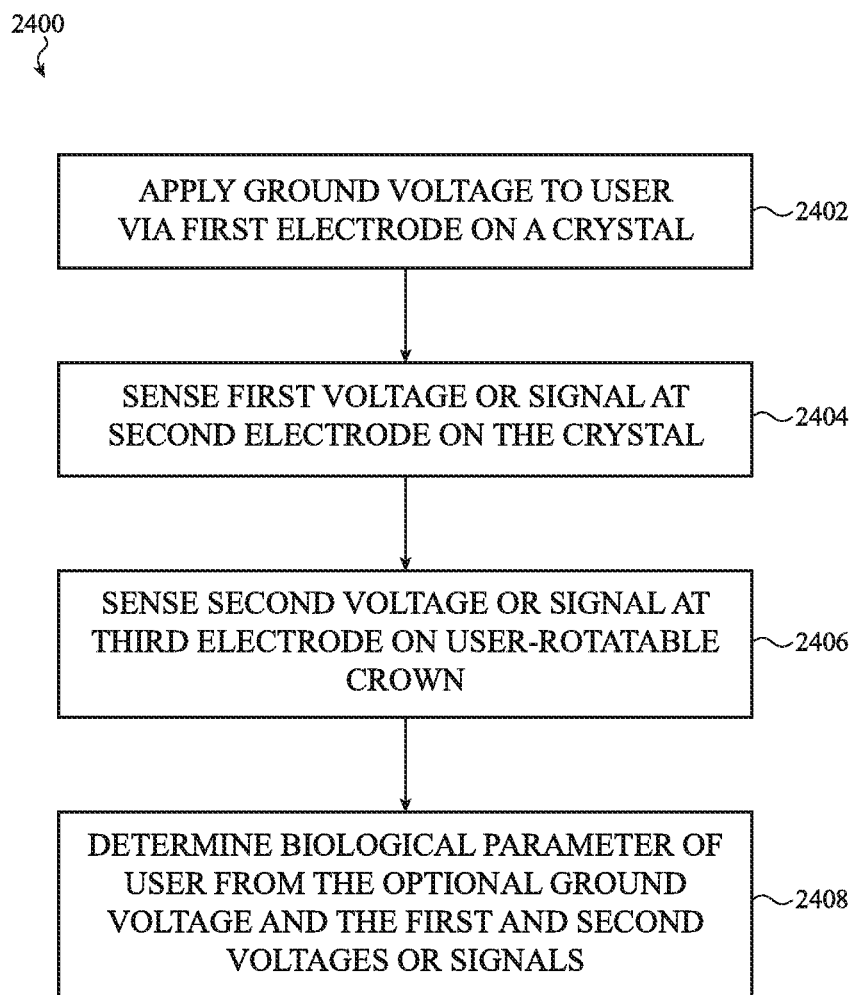
FIG. 24 shows an example method of determining a biological parameter of a user wearing a watch or other wearable electronic device.

FIG. 24 shows an example method 2400 of determining a biological parameter of a user wearing an electronic watch or other wearable electronic device, such as a watch or wearable electronic device described herein.

At block 2402, a ground voltage is optionally applied to a user via a first electrode on the electronic device. The first electrode may be on an exterior surface of a carrier that forms part of a housing of the electronic device. The operation(s) at 2402 may be performed, for example, by the processor described with reference to FIG. 24, using one of the electrodes described with reference to FIGS. 1B, 2A-2C, 3, 4A-4C, 5D, 5E, 6-8, 9A-9C, 10A-10D, & 23.

At block 2404, a first voltage or signal is sensed at a second electrode on the electronic device. The second electrode may also be on the exterior surface of the carrier. The operation(s) at 2404 may be performed, for example, by the processor described with reference to FIG. 24, using one of the electrodes described with reference to FIGS. 1B, 2A-2C, 3, 4A-4C, 5D, 5E, 6-8, 9A-9C, 10A-10D, 11, 12A, 12B, 13, 14, 15, 16A, 16B, 17A, 17B, 18A, 18B, 19, 20, 21, 22, & 23.

At block 2406, a second voltage or signal is sensed at a third electrode on the electronic device. The third electrode may be on a user-rotatable crown of the electronic device, or on a button of the electronic device, or on another surface of the housing of the electronic device. In some embodiments, the ground voltage is applied and the first voltage or signal is sensed on a wrist of one arm of the user, and the second voltage or signal is sensed on a fingertip of the user (with the fingertip belonging to a finger on a hand on the other arm of the user). The operation(s) at 2406 may be performed, for example, by the processor described with reference to FIG. 24, using one of the electrodes described with reference to FIGS. 1B, 2A-2C, 3, 4A-4C, 5D, 5E, 6-8, 9A-9C, 10A-10D, 11, 12A, 12B, 13, 14, 15, 16A, 16B, 17A, 17B, 18A, 18B, 19, 20, 21, 22, & 23.

At block 2408, the biological parameter of the user may be determined from the optional ground voltage, the first voltage or signal, and the second voltage or signal. The ground voltage may provide a reference for the first and second voltages or signals, or may otherwise be used to reject noise from the first and second voltages or signals. When the first and second voltages are obtained from different parts of the user's body, the biological parameter may be an electrocardiogram for the user. The operation(s) at 2408 may be performed, for example, by the processor described with reference to FIG. 25.

Figure 25:
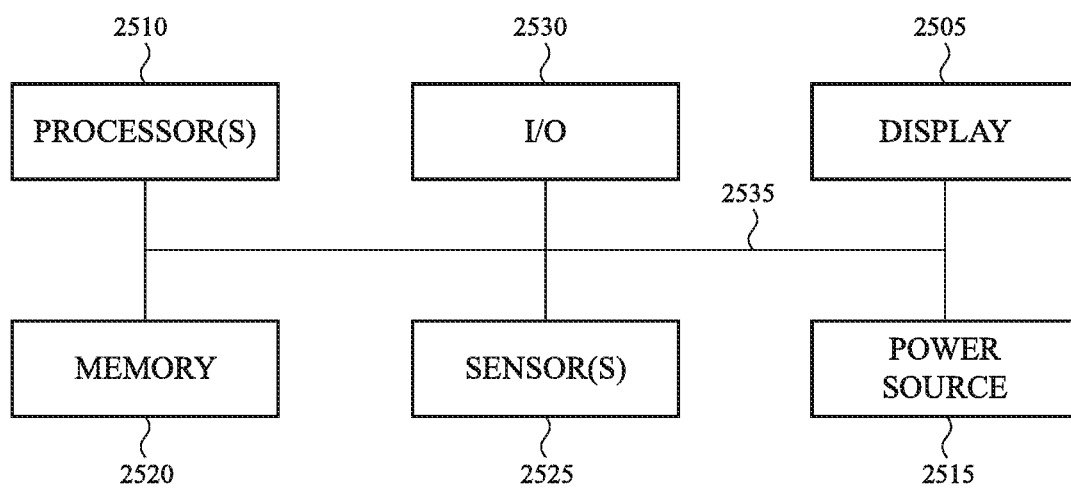
FIG. 25 shows a sample electrical block diagram of an electronic device such as a watch or other wearable electronic device.

FIG. 25 shows a sample electrical block diagram of an electronic device 2500, which electronic device may in some cases take the form of any of the electronic watches or other wearable electronic devices described with reference to FIGS. 1-23, or other portable or wearable electronic devices. The electronic device 2500 can include a display 2505 (e.g., a light-emitting display), a processor 2510, a power source 2515, a memory 2520 or storage device, a sensor 2525, and an input/output (I/O) mechanism 2530 (e.g., an input/output device, input/output port, or haptic input/output interface). The processor 2510 can control some or all of the operations of the electronic device 2500. The processor 2510 can communicate, either directly or indirectly, with some or all of the components of the electronic device 2500. For example, a system bus or other communication mechanism 2535 can provide communication between the processor 2510, the power source 2515, the memory 2520, the sensor 2525, and the input/output mechanism 2530.

The processor 2510 can be implemented as any electronic device capable of processing, receiving, or transmitting data or instructions. For example, the processor 2510 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitably configured computing element or elements.

It should be noted that the components of the electronic device 2500 can be controlled by multiple processors. For example, select components of the electronic device 2500 (e.g., a sensor 2525) may be controlled by a first processor and other components of the electronic device 2500 (e.g., the display 2505) may be controlled by a second processor, where the first and second processors may or may not be in communication with each other. In some cases, the processor 2510 may determine a biological parameter of a user of the electronic device, such as an ECG for the user.

The power source 2515 can be implemented with any device capable of providing energy to the electronic device 2500. For example, the power source 2515 may be one or more batteries or rechargeable batteries. Additionally or alternatively, the power source 2515 can be a power connector or power cord that connects the electronic device 2500 to another power source, such as a wall outlet.

The memory 2520 can store electronic data that can be used by the electronic device 2500. For example, the memory 2520 can store electrical data or content such as, for example, audio and video files, documents and applications, device settings and user preferences, timing signals, control signals, and data structures or databases. The memory 2520 can be configured as any type of memory. By way of example only, the memory 2520 can be implemented as random access memory, read-only memory, Flash memory, removable memory, other types of storage elements, or combinations of such devices.

The electronic device 2500 may also include one or more sensors 2525 positioned almost anywhere on the electronic device 2500. The sensor(s) 2525 can be configured to sense one or more type of parameters, such as but not limited to, pressure, light, touch, heat, movement, relative motion, biometric data (e.g., biological parameters), and so on. For example, the sensor(s) 2525 may include a heat sensor, a position sensor, a light or optical sensor, an accelerometer, a pressure transducer, a gyroscope, a magnetometer, a health monitoring sensor, and so on. Additionally, the one or more sensors 2525 can utilize any suitable sensing technology, including, but not limited to, capacitive, ultrasonic, resistive, optical, ultrasound, piezoelectric, and thermal sensing technology. In some examples, the sensors 2525 may include one or more of the electrodes described herein (e.g., one or more electrodes on an exterior surface of a carrier that forms part of a housing for the electronic device 2500 and/or an electrode on a crown, button, or other housing member of the electronic device).

The I/O mechanism 2530 can transmit and/or receive data from a user or another electronic device. An I/O device can include a display, a touch sensing input surface, one or more buttons (e.g., a graphical user interface "home" button), one or more cameras, one or more microphones or speakers, one or more ports such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

As discussed above, graphics displayed on the electronic devices herein may be manipulated through inputs provided to the crown. FIGS. 26A-28B generally depict examples of changing a graphical output displayed on an electronic device through inputs provided by force and/or rotational inputs to a crown assembly of the device. This manipulation (e.g., selection, acknowledgement, motion, dismissal, magnification, and so on) of a graphic may result in changes in operation of the electronic device and/or graphical output displayed by the electronic device. Although specific examples are provided and discussed, many operations may be performed by rotating and/or applying force to a crown such as the examples described above. Accordingly, the following discussion is by way of example and not limitation.

Figure 26A:
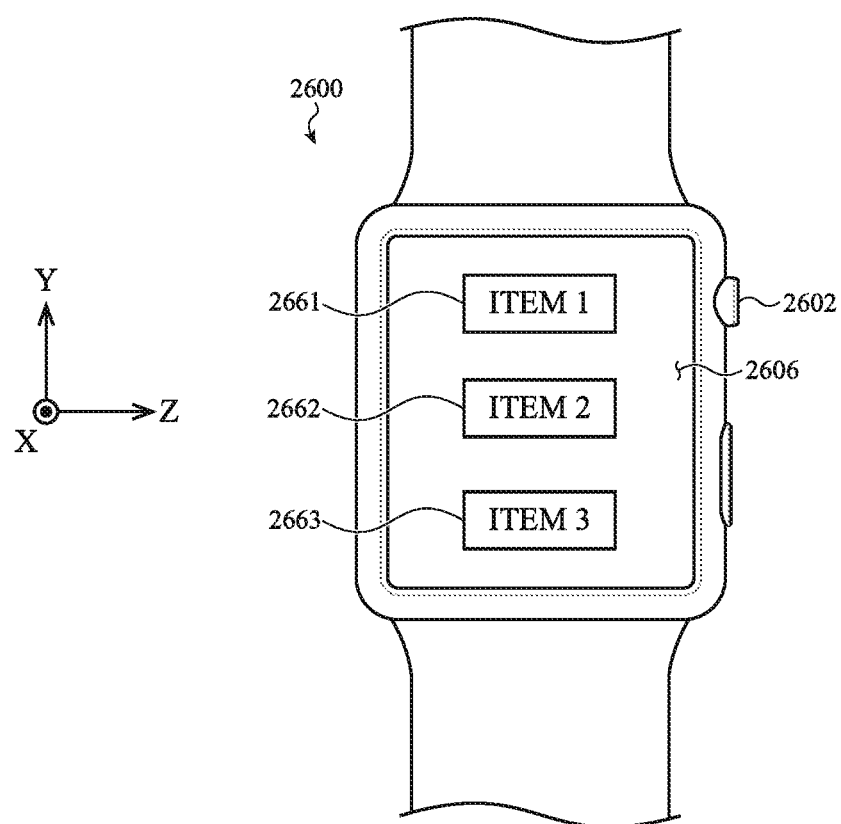
FIG. 26A illustrates a sample electronic watch displaying a list.

FIG. 26A depicts an example electronic device 2600 (shown here as an electronic watch) having a crown 2602. The crown 2602 may be similar to the examples described above, and may receive force inputs along a first lateral direction, a second lateral direction, or an axial direction of the crown. The crown 2602 may also receive rotational inputs. A display 2606 provides a graphical output (e.g., shows information and/or other graphics). In some embodiments, the display 2606 may be configured as a touch-sensitive display capable of receiving touch and/or force input. In the current example, the display 2606 depicts a list of various items 2661, 2662, 2663, all of which are example graphics.

Figure 26B:
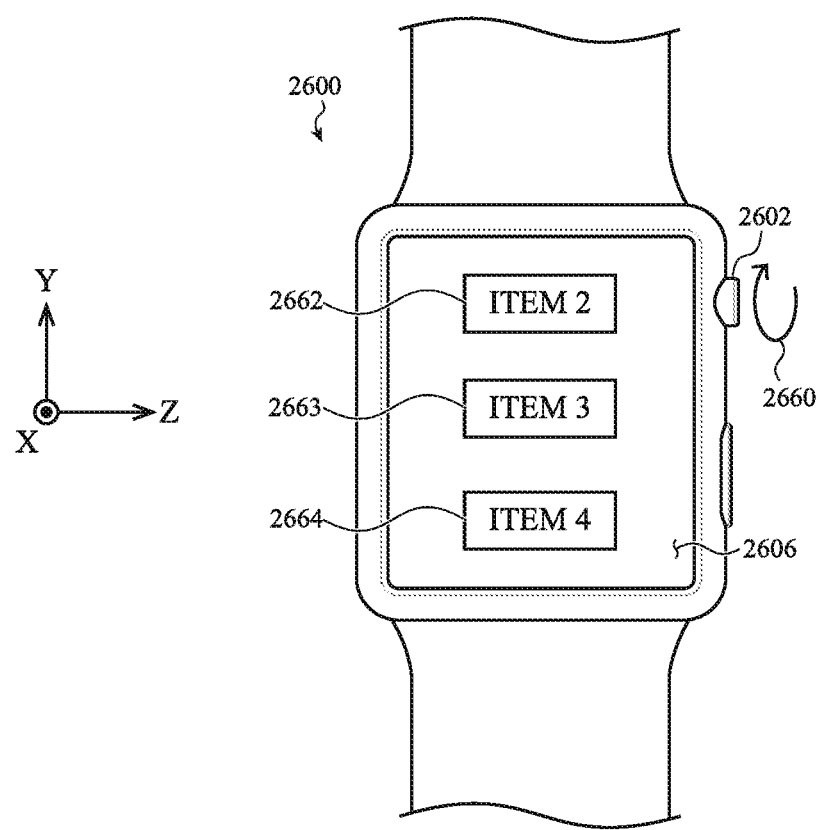
FIG. 26B illustrates the sample electronic watch of FIG. 26A, with an updated list in response to a crown input.

FIG. 26B illustrates how the graphical output shown on the display 2606 changes in a first manner as the crown 2602 rotates, partially or completely (as indicated by the arrow 2660). Rotating the crown 2602 causes the list to scroll or otherwise move on the screen, such that the first item 2661 is no longer displayed, the second and third items 2662, 2663 each move upwards on the display, and a fourth item 2664 is now shown at the bottom of the display. This is one example of a scrolling operation that can be executed by rotating the crown 2602. Such scrolling operations may provide a simple and efficient way to depict multiple items relatively quickly and in sequential order. A speed of the scrolling operation may be controlled by the amount of rotational force applied to the crown 2602 and/or the speed at which the crown 2602 is rotated. Faster or more forceful rotation may yield faster scrolling, while slower or less forceful rotation yields slower scrolling. The crown 2602 may receive an axial force (e.g., a force inward toward the display 2606 or watch body) to select an item from the list, in certain embodiments.

Figure 27A:
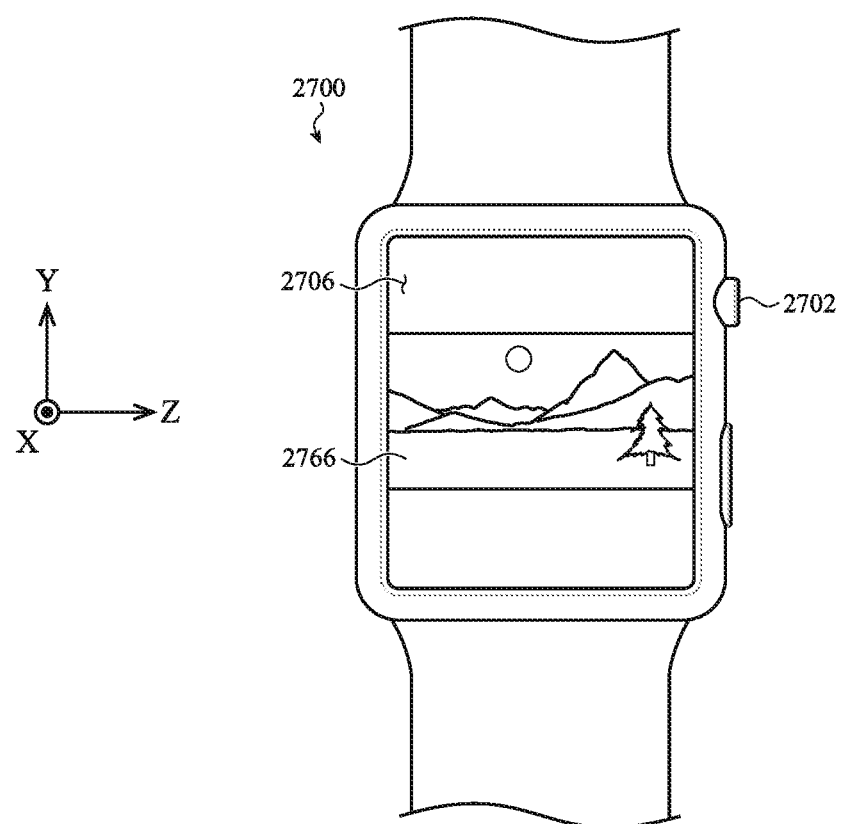
FIG. 27A illustrates a sample electronic watch displaying a graphic.
Figure 27B:
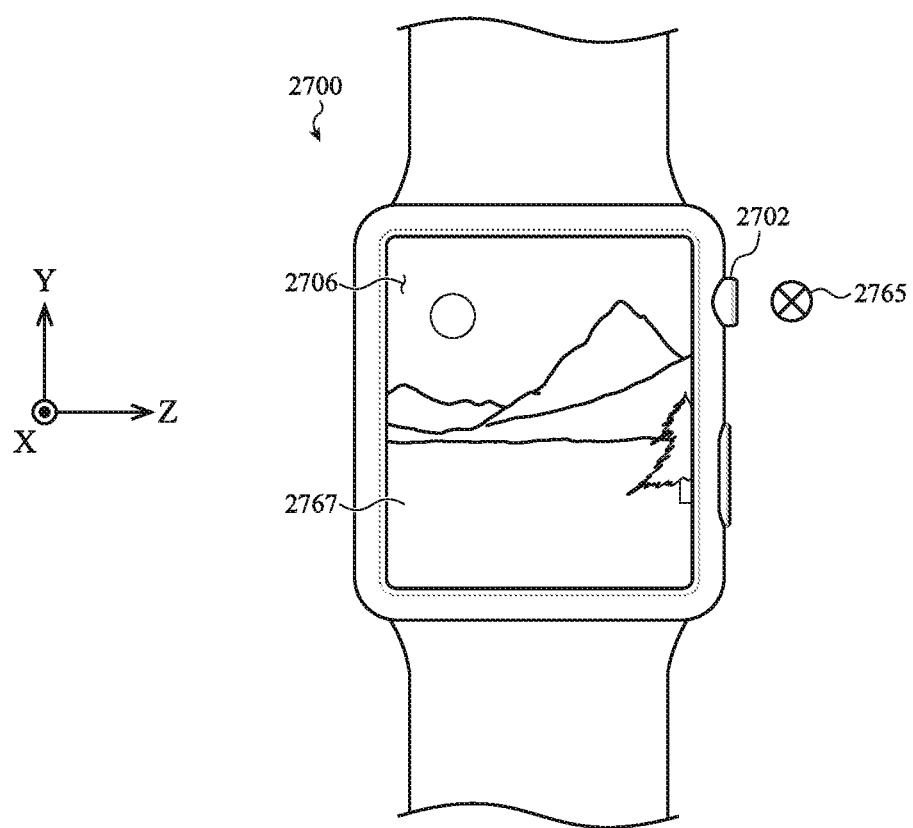
FIG. 27B illustrates the sample electronic watch of FIG. 27A with the graphic updated in response to a crown input.

FIGS. 27A and 27B illustrate an example zoom operation. The display 2706 depicts a picture 2766 at a first magnification, shown in FIG. 27A; the picture 2766 is yet another example of a graphic. A user may apply a translating force (e.g., a force along the z-axis) or a lateral force (e.g., a force along the x-axis) to the crown 2702 of the electronic device 2700 (illustrated by arrow 2765), and in response the display may change a graphic in a second manner, such as zooming into the picture 2766 so that a portion 2767 of the picture is shown at an increased magnification. This is shown in FIG. 27B. The direction of zoom (in vs. out) and speed of zoom, or location of zoom, may be controlled through force applied to the crown 2702, and particularly through the direction of applied force and/or magnitude of applied force. Applying force to the crown 2702 in a first direction may zoom in, while applying force to the crown 2702 in an opposite direction may zoom out. Alternately, rotating or applying force to the crown 2702 in a first direction may change the portion of the picture subject to the zoom effect. In some embodiments, applying an axial or translating force (e.g., a force along the z-axis) to the crown 2702 may toggle between different zoom modes or inputs (e.g., direction of zoom vs. portion of picture subject to zoom), or otherwise change the displayed graphic in a second manner. In yet other embodiments, applying force to the crown 2702 along another direction, such as along the y-axis, may return the picture 2766 to the default magnification shown in FIG. 27A.

Figure 28A:
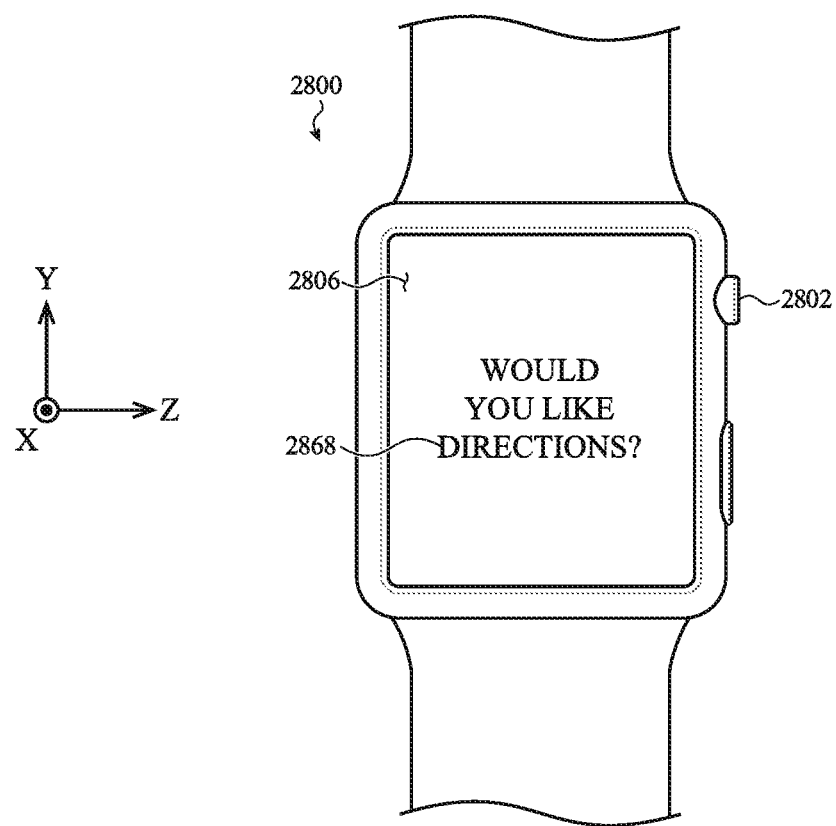
FIG. 28A illustrates a sample electronic watch displaying a first graphic.
Figure 28B:
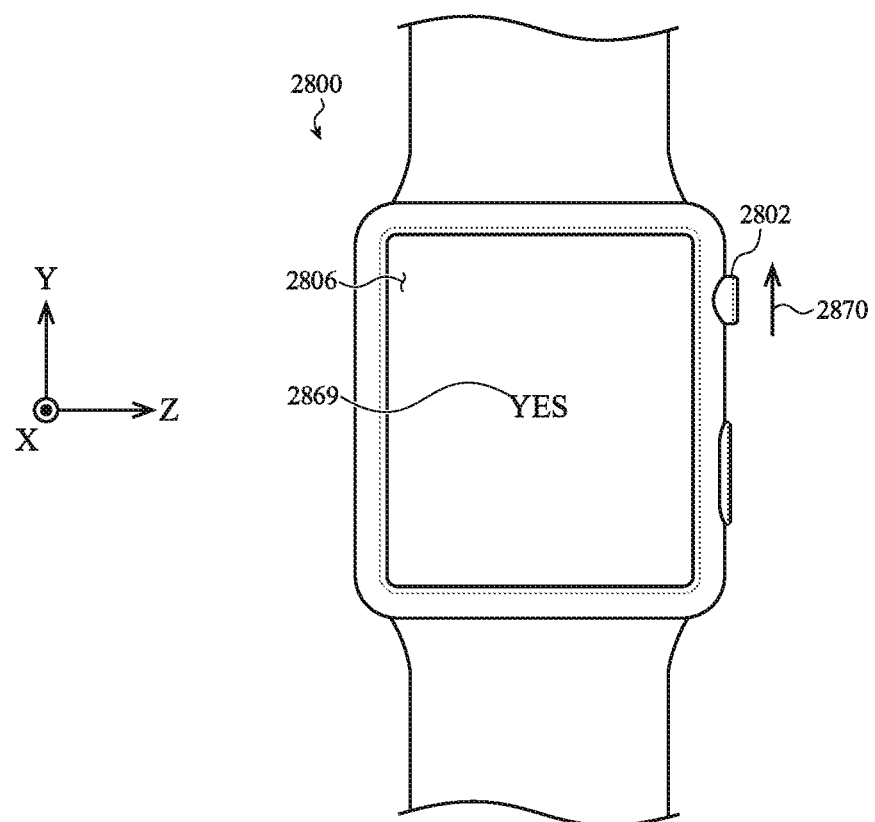
FIG. 28B illustrates the sample electronic watch of FIG. 28A displaying a second graphic in response to a crown input.

FIGS. 28A and 28B illustrate possible use of the crown 2802 to change an operational state of the electronic device 2800 or otherwise toggle between inputs. Turning first to FIG. 28A, the display 2806 depicts a question 2868, namely, "Would you like directions?" As shown in FIG. 28B, a lateral force may be applied to the crown 2802 (illustrated by arrow 2870) to answer the question. Applying force to the crown 2802 provides an input interpreted by the electronic device 2800 as "yes," and so "YES" is displayed as a graphic 2869 on the display 2806. Applying force to the crown 2802 in an opposite direction may provide a "no" input. Both the question 2868 and graphic 2869 are examples of graphics.

In the embodiment shown in FIGS. 28A and 28B, the force applied to the crown 2802 is used to directly provide the input, rather than select from options in a list (as discussed above with respect to FIGS. 26A and 26B).

As mentioned previously, force or rotational input to a crown of an electronic device may control many functions beyond those listed here. The crown may receive distinct force or rotational inputs to adjust a volume of an electronic device, a brightness of a display, or other operational parameters of the device. A force or rotational input applied to the crown may rotate to turn a display on or off, or turn the device on or off. A force or rotational input to the crown may launch or terminate an application on the electronic device. Further, combinations of inputs to the crown may likewise initiate or control any of the foregoing functions, as well.

In some cases, the graphical output of a display may be responsive to inputs applied to a touch-sensitive display (e.g., displays 2606, 2706, 2806, and the like) in addition to inputs applied to a crown. The touch-sensitive display may include or be associated with one or more touch and/or force sensors that extend along an output region of a display and which may use any suitable sensing elements and/or sensing techniques to detect touch and/or force inputs applied to the touch-sensitive display. The same or similar graphical output manipulations that are produced in response to inputs applied to the crown may also be produced in response to inputs applied to the touch-sensitive display. For example, a swipe gesture applied to the touch-sensitive display may cause the graphical output to move in a direction corresponding to the swipe gesture. As another example, a tap gesture applied to the touch-sensitive display may cause an item to be selected or activated. In this way, a user may have multiple different ways to interact with and control an electronic watch, and in particular the graphical output of an electronic watch. Further, while the crown may provide overlapping functionality with the touch-sensitive display, using the crown allows for the graphical output of the display to be visible (without being blocked by the finger that is providing the touch input).

As another example, and of the inputs described in FIGS. 26A-28B may be used to select, initiate, or display an ECG, or otherwise begin the operation of determining an ECG or launching an ECG application.

As described above, one aspect of the present technology is the gathering and use of data available from various sources, including the gathering and use of biological parameters of a user, to monitor or improve the user's health or fitness. The present disclosure contemplates that in some instances, this gathered data may include personal information data that uniquely identifies a specific person, or can be used to contact, locate, or identify a specific person. Such personal information data can include demographic data, location-based data, telephone numbers, email addresses, twitter IDs, home addresses, data or records relating to a user's health or level of fitness (e.g., vital sign measurements, medication information, exercise information), date of birth, or any other identifying or personal information.

The present disclosure recognizes that the use of such personal information data, in the present technology, can be used to the benefit of users. For example, the personal information data can be used to aid a user in monitoring or improving their health or fitness (e.g., biological parameters or health and fitness data may be used to provide insights into a user's general wellness, or may be used as positive feedback to individuals using technology to pursue wellness goals).

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of biological parameters or conditions identified therefrom, the present technology can be configured to allow users to select to "opt in" or "opt out" of participation in the collection of personal information data during registration for services or anytime thereafter. In another example, users can select not to provide health or fitness-associated data to the providers of applications or services, or can prevent the transmission of such data from the device on which it is collected or outside a collection of devices that are personal to a user from which the data is obtained. In yet another example, a user can select to limit the length of time health or fitness data, or biological parameters from which such data is derived, is maintained. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing at least some personal information data. That is, the various embodiments of the present technology are not rendered inoperable due to the lack of a portion of such personal information data. For example, biological parameters can be ascertained or stored without associating the biological parameters with information identifying a particular user from which they are obtained, or with a bare minimum amount of personal information, such as non-personal information already available to service providers or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:
1. An electronic watch, comprising:
a housing;
a crown comprising:
  a crown body; and
  a shaft connected to the crown body and passing through the housing;
a transparent carrier connected to the housing and defining a first portion of a back exterior surface of the electronic watch;
a transparent cover connected to the housing and defining at least a portion of a front exterior surface of the electronic watch;
a touch-sensitive display at least partially within the housing and viewable through the transparent cover;
a first electrode comprising a conductive coating positioned on the transparent carrier, the conductive coating defining a second portion of the back exterior surface of the electronic watch and configured to contact a body of a user when the electronic watch is being worn;
a second electrode on the crown body; and
a processor within the housing and operationally connected to the first electrode and the second electrode; wherein:
the first electrode is configured to measure a first voltage;
the second electrode is configured to measure a second voltage;
the processor is configured to determine an electrocardiogram using the first voltage and the second voltage; and
the touch-sensitive display is configured to display the electrocardiogram.

2. The electronic watch of claim 1, wherein:
the touch-sensitive display is further configured to display a graphic other than the electrocardiogram; and
the touch-sensitive display is further configured to change from displaying the graphic to displaying the electrocardiogram.

3. The electronic watch of claim 2, wherein the touch-sensitive display is further configured to change from displaying the graphic to displaying the electrocardiogram in response to a crown input.

4. The electronic watch of claim 1, wherein:
the crown is configured to rotate about an axis of rotation and translate along the axis of rotation; and
the axis of rotation extends along a center of the shaft.

5. The electronic watch of claim 1, wherein the crown further comprises:
an electrically insulating split around the crown body; and
a trim around the electrically insulating split; wherein:
  the electrically insulating split is configured to electrically insulate the trim from the crown body; and
  the crown body comprises the second electrode.

6. The electronic watch of claim 1, wherein the shaft and the crown body are integrally formed with one another.

7. The electronic watch of claim 1, further comprising an insulating coating on at least one of the crown body, the shaft, or the housing.

8. An electronic watch, comprising:
a housing;
a carrier attached to a rear of the housing and formed from an optically transparent material and attached to the housing, the carrier defining:
  an inner surface; and
  an outer surface;
a conductive coating positioned on the outer surface of the carrier and defining a first electrode on the carrier;
a crown extending through the housing and configured to translate and rotate, comprising a second electrode; and
a processor operable to determine a biological parameter of a user based on voltages measured at the first electrode and the second electrode; wherein:
the voltages are measured while the user is in contact with the first electrode and the second electrode.

9. The electronic watch of claim 8, further comprising:
a collar receiving the crown;
a first collar coating on the collar and configured to reduce friction between the collar and the crown; and
a second collar coating on the first collar coating and configured to obscure the first collar coating.

10. The electronic watch of claim 8, wherein:
the crown comprises:
a shaft extending through an opening in the housing; and
a crown body integrally formed with the shaft, exterior to the housing, and configured to be rotated by the user;
the conductive coating extends along a portion of the inner surface of the carrier, around an edge of the carrier, and along a peripheral portion of the outer surface of the carrier;
the second electrode is a surface of the crown body; and
the crown body and the shaft are in electrical communication with the processor.

11. The electronic watch of claim 8, further comprising:
a transparent cover attached to the housing; and
a display viewable through the transparent cover; wherein
rotating the crown changes a graphic on the display in a first manner;
translating the crown changes the graphic in a second manner; and
the biological parameter is an electrocardiogram.

12. The electronic watch of claim 8, wherein one of rotating or translating the crown initiates determining the biological parameter.

13. The electronic watch of claim 8, further comprising a touch-sensitive display at least partially within the housing; and wherein:
touching the touch-sensitive display initiates determining the biological parameter.

14. The electronic watch of claim 13, wherein:
the biological parameter is a first biological parameter; and
the electronic watch further comprises an optical sensor subsystem configured to sense a second biological parameter through the carrier.

15. The electronic watch of claim 14, wherein:
the first biological parameter is an electrocardiogram; and
the second biological parameter is a heart rate.

16. The electronic watch of claim 8, further comprising a touch-sensitive display; wherein:
the biological parameter is an electrocardiogram; and
the electrocardiogram is shown on the touch-sensitive display.

17. A method for determining and displaying an electrocardiogram by an electronic watch, comprising:
measuring a first voltage at a first electrode on a crown of the electronic watch;
measuring a second voltage at a second electrode on a transparent carrier of the electronic watch, the second electrode defined by a conductive coating disposed on an outer surface of the transparent carrier, the conductive coating defining at least a portion of a back exterior surface of the electronic watch;
determining, by a processor of the electronic watch, the electrocardiogram using the first voltage and the second voltage; and
displaying the electrocardiogram on a display of the electronic watch.

18. The method of claim 17, further comprising:
sensing a touch on the crown of the electronic watch; wherein:
initiating measuring the first voltage and measuring the second voltage occurs in response to sensing the touch.

19. The method of claim 17, further comprising:
sensing a touch on the display of the electronic watch; wherein:
initiating measuring the first voltage and measuring the second voltage occurs in response to sensing the touch.

20. The method of claim 17, further comprising:
measuring a third voltage at a third electrode on the transparent carrier of the electronic watch; and
the operation of determining, by the processor of the electronic watch, the electrocardiogram using the first voltage and the second voltage comprises determining, by the processor of the electronic watch, the electrocardiogram using the first voltage, the second voltage, and the third voltage.

* * * * *